(12) United States Patent
Maue et al.

(10) Patent No.: US 9,706,775 B2
(45) Date of Patent: Jul. 18, 2017

(54) HALOGEN-SUBSTITUTED COMPOUNDS

(71) Applicant: BAYER ANIMAL HEALTH GMBH, Leverkusen (DE)

(72) Inventors: Michael Maue, Langenfeld (DE); Anne Decor, Langenfeld (DE); Thomas Bretschneider, Lohmar (DE); Julia Johanna Hahn, Düsseldorf (DE); Werner Hallenbach, Monheim (DE); Reiner Fischer, Monheim (DE); Hans-Georg Schwarz, Dorsten (DE); Ulrich Görgens, Ratingen (DE); Kerstin Ilg, Köln (DE); Klaus Raming, Leverkusen (DE); Johannes Köbberling, Neuss (DE); Walter Hübsch, Wuppertal (DE); Andreas Turberg, Haan (DE)

(73) Assignee: BAYER ANIMAL HEALTH GMBH, Leverkusen (DE)

( * ) Notice: Subject to any disclaimer, the term of this patent is extended or adjusted under 35 U.S.C. 154(b) by 0 days.

(21) Appl. No.: 14/772,471

(22) PCT Filed: Feb. 27, 2014

(86) PCT No.: PCT/EP2014/053838
§ 371 (c)(1),
(2) Date: Sep. 3, 2015

(87) PCT Pub. No.: WO2014/135439
PCT Pub. Date: Sep. 12, 2014

(65) Prior Publication Data
US 2016/0007604 A1    Jan. 14, 2016

(30) Foreign Application Priority Data
Mar. 4, 2013 (EP) ..................... 13157618

(51) Int. Cl.
C07D 403/04    (2006.01)
C07D 231/12    (2006.01)
A01N 43/56     (2006.01)
A01N 43/647    (2006.01)
A01N 43/653    (2006.01)
C07D 401/14    (2006.01)
C07D 403/14    (2006.01)

(52) U.S. Cl.
CPC ........... *A01N 43/56* (2013.01); *A01N 43/647* (2013.01); *A01N 43/653* (2013.01); *C07D 231/12* (2013.01); *C07D 401/14* (2013.01); *C07D 403/04* (2013.01); *C07D 403/14* (2013.01)

(58) Field of Classification Search
None
See application file for complete search history.

(56) References Cited

FOREIGN PATENT DOCUMENTS

WO    WO 2012/107434    *    8/2012    ........... C07D 401/14

* cited by examiner

*Primary Examiner* — Alicia L Otton
(74) *Attorney, Agent, or Firm* — McBee Moore Woodward Vank LLC; Susan McBee; Chester Moore

(57) ABSTRACT

The invention relates inter alia to halogen-substituted compounds of the general formula (II)

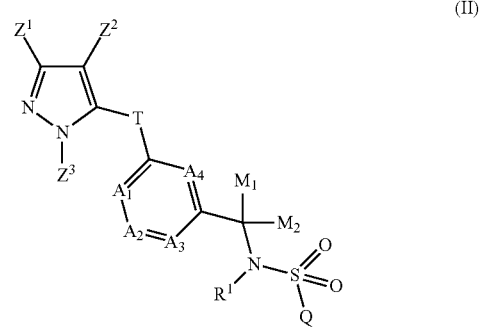

(II)

in which the radicals $A_1$-$A_4$, T, n, W, Q, $R^1$ and $Z^1$-$Z^3$ have the meanings given in the description. Also described are processes for preparing the compounds of the formula (II). The compounds according to the invention are particularly suitable for controlling insects, arachnids and nematodes in agriculture and ectoparasites in veterinary medicine.

16 Claims, No Drawings

HALOGEN-SUBSTITUTED COMPOUNDS

The present application relates to novel halogen-substituted compounds, to processes for their preparation and to their use for controlling animal pests, in particular arthropods and especially insects, arachnids and nematodes.

It is known that certain halogen-substituted compounds have herbicidal action (cf. J. Org. Chem. 1997, 62(17), 5908-5919, J. Heterocycl. Chem. 1998, 35(6), 1493-1499, WO 2004/035545, WO 2004/106324, US 2006/069132, WO 2008/029084).

Furthermore, it is known that certain halogen-substituted compounds are insecticidally active (EP1911751, WO2012-069366, WO2012-080376 & WO2012-107434).

In addition, it is known that certain halogen-substituted compounds have FAAH-inhibitory activities (WO 2009/151991).

Modern crop protection compositions have to meet many demands, for example in relation to efficacy, persistence and spectrum of their action and possible use. Questions of toxicity, the combinability with other active compounds or formulation auxiliaries play a role, as well as the question of the expense that the synthesis of an active compound requires. Furthermore, resistances may occur. For all these reasons, the search for novel crop protection agents can never be considered as having been concluded, and there is a constant need for novel compounds having properties which, compared to the known compounds, are improved at least in respect of individual aspects.

It was an object of the present invention to provide compounds which widen the spectrum of the pesticides under various aspects and/or improve their activity.

Surprisingly, it has now been found that certain halogen-substituted compounds and their N-oxides and salts have biological properties and are particularly suitable for controlling animal pests, and can therefore be employed particularly well in the agrochemical field and in the animal health sector.

The halogen-substituted compounds according to the invention are defined by the general formulae (I) and (II)

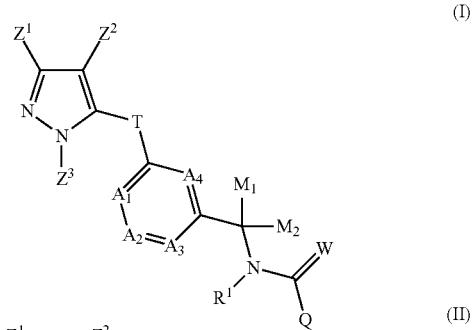

(I)

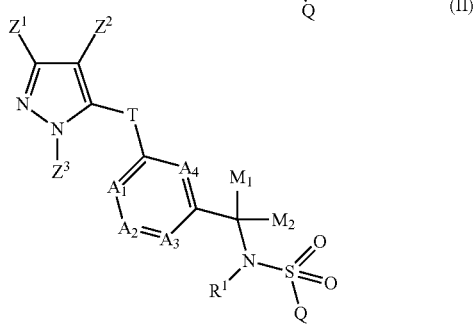

(II)

in which
R$^1$ represents hydrogen, optionally substituted C$_1$-C$_6$-alkyl, C$_3$-C$_6$-alkenyl, C$_3$-C$_6$-alkynyl, C$_3$-C$_7$-cycloalkyl, C$_1$-C$_6$-alkylcarbonyl, C$_1$-C$_6$-alkoxycarbonyl, aryl-(C$_1$-C$_3$)-alkyl, heteroaryl-(C$_1$-C$_3$)-alkyl,
M$^1$ and M$^2$ each independently of one another represent hydrogen, cyano or represent optionally mono- or polysubstituted C$_1$-C$_6$-alkyl, C$_2$-C$_6$-alkenyl, C$_2$-C$_6$-alkynyl, C$_3$-C$_6$-cycloalkyl, C$_1$-C$_6$-alkoxycarbonyl, or
M$^1$ and M$^2$ with the carbon atom to which they are attached form an optionally substituted 3-, 4-, 5- or 6-membered ring which optionally contains 0, 1 or 2 nitrogen atoms and/or 0, 1 or 2 oxygen atoms and/or 0, 1 or 2 sulphur atoms,
the chemical groupings
A$_1$ represents CR$^2$ or nitrogen,
A$_2$ represents CR$^3$ or nitrogen,
A$_3$ represents CR$^4$ or nitrogen and
A$_4$ represents CR$^5$ or nitrogen,
but where not more than three of the chemical groupings A$_1$ to A$_4$ simultaneously represent nitrogen;
R$^2$, R$^3$, R$^4$ and R$^5$ independently of one another represent hydrogen, halogen, cyano, nitro, optionally substituted C$_1$-C$_6$-alkyl, C$_3$-C$_6$-cycloalkyl, C$_1$-C$_6$-alkoxy, N—C$_1$-C$_6$-alkoxy-imino-C$_1$-C$_3$-alkyl, C$_1$-C$_6$-alkylsulphanyl, C$_1$-C$_6$-alkylsulphinyl, C$_1$-C$_6$-alkylsulphonyl, N—C$_1$-C$_6$-alkylamino or N,N-di-C$_1$-C$_6$-alkylamino;
if none of the groupings A$_2$ and A$_3$ represents nitrogen, R$^3$ and R$^4$ together with the carbon atom to which they are attached may form a 5- or 6-membered ring which contains 0, 1 or 2 nitrogen atoms and/or 0 or 1 oxygen atom and/or 0 or 1 sulphur atom, or
if none of the groupings A$_1$ and A$_2$ represents nitrogen, R$^2$ and R$^3$ together with the carbon atom to which they are attached may form a 6-membered ring which contains 0, 1 or 2 nitrogen atoms;
W represents oxygen or sulphur;
Q represents hydrogen, hydroxy, amino or one of the optionally substituted groupings alkyl, alkoxy, alkenyl, alkynyl, cycloalkyl, heterocycloalkyl, cycloalkylalkyl, arylalkyl, heteroarylalkyl or represents a grouping N-alkylamino, N-alkylcarbonylamino, N,N-dialkylamino; or
Q represents an unsaturated 6-membered carbocycle which is optionally mono- or polysubstituted by V or an unsaturated 5- or 6-membered heterocyclic ring which is optionally mono- or polysubstituted by V, where
V independently of one another represent halogen, cyano, nitro, optionally substituted alkyl, alkenyl, alkynyl, cycloalkyl, alkoxy, N-alkoxyiminoalkyl, alkylsulphanyl, alkylsulphinyl, alkylsulphonyl, N,N-dialkylamino,
T represents one of the 5-membered heteroaromatics T1-T8 listed below, where the bond to the pyrazole head group is marked with an asterisk,

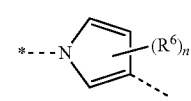

T1

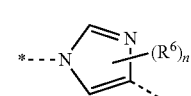

T2

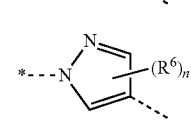

T3

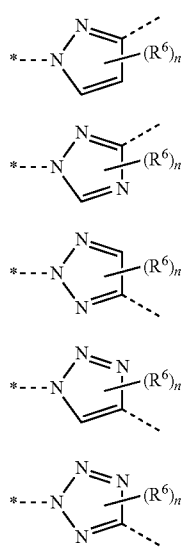

T4

T5

T6

T7

T8 where

R$^6$ independently of one another represent halogen, cyano, nitro, amino or optionally substituted C$_1$-C$_6$-alkyl, C$_1$-C$_6$-alkoxy, C$_1$-C$_6$-alkylcarbonyl, C$_1$-C$_6$-alkylsulphanyl, C$_1$-C$_6$-alkylsulphinyl, C$_1$-C$_6$-alkylsulphonyl, and n represents the values 0-2;

Z$^1$ represents optionally substituted alkyl and cycloalkyl, and

Z$^2$ represents hydrogen, halogen, cyano, nitro, amino or optionally substituted alkyl, alkylcarbonyl, alkylsulphanyl, alkylsulphinyl, alkylsulphonyl, and Z$^3$ represents hydrogen or optionally substituted alkyl, cycloalkyl, alkenyl, alkynyl, aryl or hetaryl.

Furthermore, the radicals R$^1$, M$^1$, M$^2$ Q, V and R$^6$ have the following alternative meanings:

R$^1$ represents hydrogen, optionally substituted C$_1$-C$_6$-alkyl, C$_2$-C$_6$-alkenyl, C$_2$-C$_6$-alkynyl, C$_3$-C$_7$-cycloalkyl, C$_1$-C$_6$-alkylcarbonyl, C$_1$-C$_6$-alkoxycarbonyl, aryl-(C$_1$-C$_3$)-alkyl, heteroaryl-(C$_1$-C$_3$)-alkyl, M$^1$ and M$^2$ each independently of one another represent hydrogen, cyano or represent optionally mono- or polysubstituted C$_1$-C$_6$-alkyl, C$_2$-C$_6$-alkenyl, C$_2$-C$_6$-alkynyl, C$_3$-C$_6$-cycloalkyl, C$_2$-C$_7$-alkoxycarbonyl, or Q represents an unsaturated 6-membered carbocycle which is optionally mono- or polysubstituted by V or an unsaturated 5- or 6-membered heterocyclic ring which is optionally mono- or polysubstituted by V, where V independently of one another represent halogen, cyano, nitro, optionally substituted alkyl, alkenyl, alkynyl, cycloalkyl, alkoxy, N-alkoxyiminoalkyl, alkylsulphanyl, alkylsulphinyl, alkylsulphonyl, N,N-dialkylamino, R$^6$ independently of one another represent halogen, cyano, nitro, amino or optionally substituted C$_1$-C$_6$-alkyl, C$_1$-C$_6$-alkoxy, C$_1$-C$_6$-alkylcarbonyl, C$_1$-C$_6$-alkylsulphanyl, C$_1$-C$_6$-alkylsulphinyl, C$_1$-C$_6$-alkylsulphonyl.

General preference for the purpose of this application is always given to the compounds of the general formula (II), independently of the degree of preference of the respective radical definitions.

Preference is given to compounds of the formulae (I) and (II)

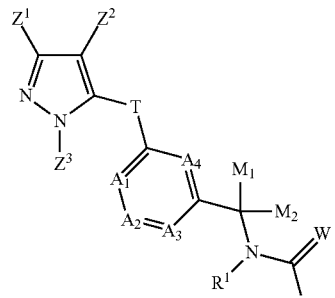

(I)

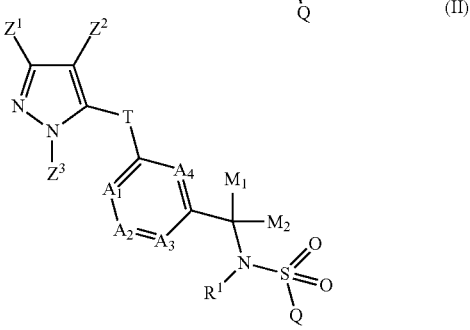

(II)

in which

R$^1$ represents hydrogen, optionally substituted C$_1$-C$_6$-alkyl, C$_3$-C$_6$-alkenyl, C$_3$-C$_6$-alkynyl, C$_3$-C$_7$-cycloalkyl, C$_1$-C$_6$-alkylcarbonyl, C$_1$-C$_6$-alkoxycarbonyl, aryl-(C$_1$-C$_3$)-alkyl, heteroaryl-(C$_1$-C$_3$)-alkyl, M$^1$ and M$^2$ each independently of one another represent hydrogen, cyano or represent optionally mono- or polysubstituted C$_1$-C$_6$-alkyl, C$_2$-C$_6$-alkenyl, C$_2$-C$_6$-alkynyl, C$_3$-C$_6$-cycloalkyl, C$_1$-C$_6$-alkoxycarbonyl, or M$^1$ and M$^2$ with the carbon atom to which they are attached form an optionally substituted 3-, 4-, 5- or 6-membered ring which optionally contains 0, 1 or 2 nitrogen atoms and/or 0, 1 or 2 oxygen atoms and/or 0, 1 or 2 sulphur atoms, the chemical groupings A$_1$ represents CR$^2$ or nitrogen, A$_2$ represents CR$^3$ or nitrogen, A$_3$ represents CR$^4$ or nitrogen and A$_4$ represents CR$^5$ or nitrogen, but where not more than three of the chemical groupings A$_1$ to A$_4$ simultaneously represent nitrogen;

R$^2$, R$^3$, R$^4$ and R$^5$ independently of one another represent hydrogen, halogen, cyano, nitro, optionally substituted C$_1$-C$_6$-alkyl, C$_3$-C$_6$-cycloalkyl, C$_1$-C$_6$-alkoxy, N—C$_1$-C$_6$-alkoxyimino-C$_1$-C$_3$-alkyl, C$_1$-C$_6$-alkylsulphanyl, C$_1$-C$_6$-alkylsulphinyl, C$_1$-C$_6$-alkylsulphonyl, N—C$_1$-C$_6$-alkylamino or N,N-di-C$_1$-C$_6$-alkylamino;

if none of the groupings A$_2$ and A$_3$ represents nitrogen, R$^3$ and R$^4$ together with the carbon atom to which they are attached may form a 5- or 6-membered ring which contains 0, 1 or 2 nitrogen atoms and/or 0 or 1 oxygen atom and/or 0 or 1 sulphur atom, or if none of the groupings A$_1$ and A$_2$ represents nitrogen, R$^2$ and R$^3$ together with the carbon atom to which they are attached may form a 6-membered ring which contains 0, 1 or 2 nitrogen atoms;

W represents oxygen or sulphur;

Q represents hydrogen, formyl, hydroxy, amino or one of the optionally substituted groupings C$_1$-C$_6$-alkyl, C$_2$-C$_6$-alkenyl, $C_2$-$C_6$-alkynyl, $C_3$-$C_6$-cycloalkyl, $C_2$-$C_7$-heterocycloalkyl, $C_1$-$C_4$-alkoxy, $C_3$-$C_6$-cycloalkyl-$C_1$-$C_6$-alkyl, aryl-($C_1$-$C_3$)-alkyl, heteroaryl-($C_1$-$C_3$)-alkyl or represents a grouping N—$C_1$-$C_4$-alkylamino, N—$C_1$-$C_4$-alkylcarbonylamino, N,N-di-$C_1$-$C_4$-alkylamino; or Q represents an unsaturated 6-membered carbocycle which is optionally mono- or polysubstituted by V or an unsaturated 5- or 6-membered heterocyclic ring which is optionally mono- or polysubstituted by V, where V independently of one another represent halogen, cyano, nitro, optionally substituted $C_1$-$C_6$-alkyl, $C_2$-$C_4$-alkenyl, $C_2$-$C_4$-alkynyl, $C_3$-$C_6$-cycloalkyl, $C_1$-$C_6$-alkoxy, N—$C_1$-$C_6$-alkoxy-imino-$C_1$-$C_3$-alkyl, $C_1$-$C_6$-alkylsulphanyl, $C_1$-$C_6$-alkylsulphinyl, $C_1$-$C_6$-alkylsulphonyl, N,N-di-($C_1$-$C_6$-alkyl)amino;

T represents one of the 5-membered heteroaromatics T1-T8 listed below, where the bond to the pyrazole head group is marked with an asterisk,

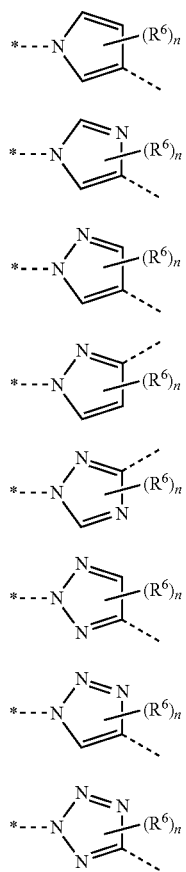

where $R^6$ independently of one another represent halogen, cyano, nitro, amino or optionally halogen-substituted $C_1$-$C_6$-alkyl, $C_1$-$C_6$-alkoxy, $C_1$-$C_6$-alkylcarbonyl, $C_1$-$C_6$-alkylsulphanyl, $C_1$-$C_6$-alkylsulphinyl, $C_1$-$C_6$-alkylsulphonyl, and n represents the values 0-1;

$Z^1$ represents optionally substituted $C_1$-$C_6$-haloalkyl, $C_3$-$C_6$-halocycloalkyl, and $Z^2$ represents hydrogen, halogen, cyano, nitro, amino or optionally substituted $C_1$-$C_6$-alkyl, $C_1$-$C_6$-alkylcarbonyl, $C_1$-$C_6$-alkylsulphanyl, $C_1$-$C_6$-alkylsulphinyl, $C_1$-$C_6$-alkylsulphonyl, and $Z^3$ represents hydrogen or optionally substituted $C_1$-$C_6$-alkyl, $C_3$-$C_6$-cycloalkyl, $C_3$-$C_6$-alkenyl, $C_3$-$C_6$-alkynyl, aryl or hetaryl.

Preference is furthermore also given to compounds of the formulae (I) and (II) in which the radicals below are alternatively defined as follows:

$R^1$ represents hydrogen, optionally substituted $C_1$-$C_6$-alkyl, $C_2$-$C_6$-alkenyl, $C_2$-$C_6$-alkynyl, $C_3$-$C_7$-cycloalkyl, $C_1$-$C_6$-alkylcarbonyl, $C_1$-$C_6$-alkoxycarbonyl, aryl-($C_1$-$C_3$)-alkyl, heteroaryl-($C_1$-$C_3$)-alkyl, $M^1$ and $M^2$ each independently of one another represent hydrogen, cyano or represent optionally mono- or polysubstituted $C_1$-$C_6$-alkyl, $C_2$-$C_6$-alkenyl, $C_2$-$C_6$-alkynyl, $C_3$-$C_6$-cycloalkyl, $C_2$-$C_7$-alkoxycarbonyl, or $R^2$, $R^3$, $R^4$ and $R^5$ independently of one another represent hydrogen, halogen, cyano, nitro, optionally substituted $C_1$-$C_6$-alkyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulphanyl, $C_1$-$C_6$-alkylsulphinyl, $C_1$-$C_6$-alkylsulphonyl, N—$C_1$-$C_6$-alkylamino or N,N-di-$C_1$-$C_6$-alkylamino;

Q represents hydrogen, formyl, hydroxy, amino or one of the optionally substituted groupings $C_1$-$C_6$-alkyl, $C_2$-$C_6$-alkenyl, $C_2$-$C_6$-alkynyl, $C_3$-$C_6$-cycloalkyl, $C_1$-$C_5$-heterocycloalkyl, $C_1$-$C_4$-alkoxy, $C_1$-$C_6$-alkyl-$C_3$-$C_6$-cycloalkyl, aryl-($C_1$-$C_3$)-alkyl, heteroaryl-($C_1$-$C_3$)-alkyl or represents a grouping N—$C_1$-$C_4$-alkylamino, N—$C_1$-$C_4$-alkylcarbonylamino, N,N-di-$C_1$-$C_4$-alkylamino; or Q represents an unsaturated 6-membered carbocycle which is optionally mono- or polysubstituted by V or an unsaturated 5- or 6-membered heterocyclic ring which is optionally mono- or polysubstituted by V, where V independently of one another represent halogen, cyano, nitro, optionally substituted $C_1$-$C_6$-alkyl, $C_1$-$C_4$-alkenyl, $C_1$-$C_4$-alkynyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulphanyl, $C_1$-$C_6$-alkylsulphinyl, $C_1$-$C_6$-alkylsulphonyl, N,N-di-($C_1$-$C_6$-alkyl)amino;

$Z^1$ represents optionally substituted $C_1$-$C_6$-haloalkyl, $C_3$-$C_6$-cycloalkyl, $C_3$-$C_6$-halocycloalkyl, and $Z^3$ represents hydrogen or optionally substituted alkyl, cycloalkyl, alkenyl, alkynyl, aryl or hetaryl.

Particular preference is given to compounds of the formulae (I) and (II)

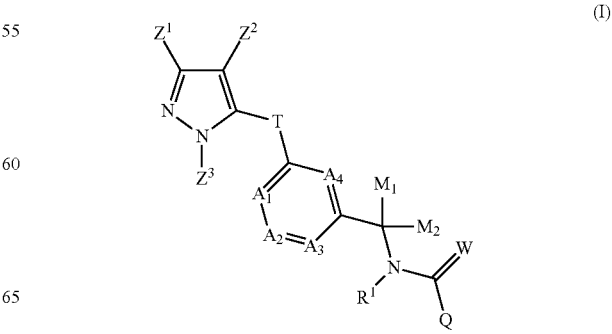

(I)

(II)

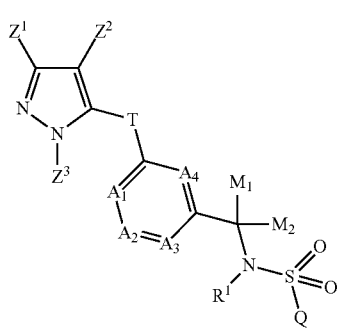

in which
R¹ represents hydrogen or represents $C_1$-$C_6$-alkyl, $C_3$-$C_6$-alkenyl, $C_3$-$C_6$-alkynyl, $C_3$-$C_7$-cycloalkyl, $C_1$-$C_6$-alkylcarbonyl, $C_1$-$C_6$-alkoxycarbonyl, aryl-($C_1$-$C_3$)-alkyl, heteroaryl-($C_1$-$C_3$)-alkyl which are optionally mono- to heptasubstituted independently of one another by fluorine, chlorine, cyano, $C_1$-$C_6$-alkoxy and $C_1$-$C_6$-alkoxycarbonyl, M¹ represents hydrogen, M² represents hydrogen, cyano or represents $C_1$-$C_6$-alkyl, $C_2$-$C_6$-alkenyl, $C_3$-$C_6$-cycloalkyl, $C_1$-$C_3$-alkoxycarbonyl which are optionally mono- to pentasubstituted independently of one another by fluorine, chlorine, cyano or $C_1$-$C_3$-alkoxy, M¹ and M² with the carbon atom to which they are attached form an optionally substituted 3-membered ring, the chemical groupings
$A_1$ represents $CR^2$ or nitrogen,
$A_2$ represents $CR^3$ or nitrogen,
$A_3$ represents $CR^4$ or nitrogen and
$A_4$ represents $CR^5$ or nitrogen,
but where not more than three of the chemical groupings $A_1$ to $A_4$ simultaneously represent nitrogen;

$R^2$, $R^3$, $R^4$ and $R^5$ independently of one another represent hydrogen, fluorine, chlorine, bromine, iodine, cyano, nitro or represent $C_1$-$C_6$-alkyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulphanyl, $C_1$-$C_6$-alkylsulphinyl, $C_1$-$C_6$-alkylsulphonyl, N—$C_1$-$C_6$-alkylamino or N,N-di-$C_1$-$C_6$-alkylamino which are optionally mono- to pentasubstituted independently of one another by fluorine, chlorine, cyano, hydroxycarbonyl, $C_1$-$C_6$-alkoxycarbonyl, $C_1$-$C_6$-alkylcarbonyl or phenyl;

W represents oxygen or sulphur;

Q represents hydrogen, amino or one of the groupings $C_1$-$C_6$-alkyl, $C_2$-$C_6$-alkenyl, $C_2$-$C_6$-alkynyl, $C_3$-$C_6$-cycloalkyl, $C_2$-$C_5$-heterocycloalkyl, $C_1$-$C_4$-alkoxy, $C_3$-$C_6$-cycloalkyl-$C_1$-$C_6$-alkyl, aryl-($C_1$-$C_3$)-alkyl, heteroaryl-($C_1$-$C_3$)-alkyl, N—$C_1$-$C_4$-alkylamino, N—$C_1$-$C_4$-alkylcarbonylamino or N,N-di-$C_1$-$C_4$-alkylamino which are optionally independently of one another mono- to pentasubstituted by hydroxy, nitro, amino, fluorine, chlorine, $C_1$-$C_6$-alkyl, $C_1$-$C_6$-alkoxy, cyano, hydroxycarbonyl, $C_1$-$C_4$-alkoxycarbonyl, $C_1$-$C_4$-alkylcarbamoyl, $C_3$-$C_7$-cycloalkylcarbamoyl, phenyl; or Q represents aryl substituted by 0-4 substituents V or a 5- or 6-membered heteroaromatic substituted by 0-4 substituents V, where V independently of one another represent halogen, cyano, nitro, optionally substituted $C_1$-$C_6$-alkyl, $C_2$-$C_4$-alkenyl, $C_2$-$C_4$-alkynyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulphanyl, $C_1$-$C_6$-alkylsulphinyl, $C_1$-$C_6$-alkylsulphonyl, N,N-di-($C_1$-$C_6$-alkyl)amino;

T represents one of the 5-membered heteroaromatics T1-T8 listed below, where the bond to the pyrazole head group is marked with an asterisk,

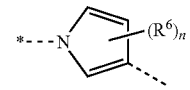
T1

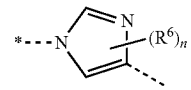
T2

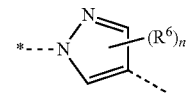
T3

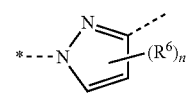
T4

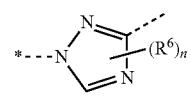
T5

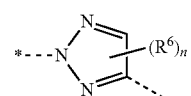
T6

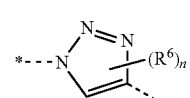
T7

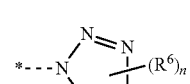
T8 where
$R^6$ independently of one another represent fluorine, chlorine, bromine, iodine, cyano, nitro, amino or represents $C_1$-$C_6$-alkyl, $C_1$-$C_6$-alkoxy, $C_1$-$C_6$-alkylcarbonyl, $C_1$-$C_6$-alkylsulphanyl, $C_1$-$C_6$-alkylsulphinyl, $C_1$-$C_6$-alkylsulphonyl which are optionally independently of one another mono- to pentasubstituted by fluorine and/or chlorine, and n represents the values 0-1;

$Z^1$ represents optionally substituted $C_1$-$C_6$-haloalkyl, $C_3$-$C_6$-halocycloalkyl, and $Z^2$ represents hydrogen, fluorine, chlorine, bromine, iodine, cyano, nitro, amino or represents $C_1$-$C_6$-alkyl, $C_1$-$C_6$-alkylcarbonyl, $C_1$-$C_6$-alkylsulphanyl, $C_1$-$C_6$-alkylsulphinyl, $C_1$-$C_6$-alkylsulphonyl which are optionally independently of one another mono- to pentasubstituted by fluorine and/or chlorine, and $Z^3$ represents hydrogen or optionally substituted $C_1$-$C_6$-alkyl, $C_3$-$C_6$-cycloalkyl, $C_3$-$C_4$-alkenyl, $C_3$-$C_4$-alkynyl, aryl or hetaryl.

Particular preference is furthermore also given to compounds of the formulae (I) and (II) in which the radicals below are alternatively defined as follows:

$R^6$ independently of one another represent halogen, cyano, nitro, amino or optionally independently of one another mono- to pentahalogen-substituted $C_1$-$C_6$-alkyl, $C_1$-$C_6$-alkoxy, $C_1$-$C_6$-alkylcarbonyl, $C_1$-$C_6$-alkylsulphanyl, $C_1$-$C_6$-alkylsulphinyl, $C_1$-$C_6$-alkylsulphonyl, and $Z^1$ represents optionally substituted $C_1$-$C_6$-alkyl, $C_3$-$C_6$-cycloalkyl, and $Z^2$ represents hydrogen, halogen, cyano, nitro, amino or represents $C_1$-$C_6$-alkyl, $C_1$-$C_6$-alkylcarbonyl, $C_1$-$C_6$-alkylsulphanyl, $C_1$-$C_6$-alkylsulphinyl, $C_1$-$C_6$-alkylsulphonyl which are optionally independently of one another mono- to pentasubstituted by fluorine and/or chlorine, and $Z^3$ represents hydrogen or optionally substituted $C_1$-$C_6$-alkyl, $C_3$-$C_6$-cycloalkyl, $C_1$-$C_4$-alkenyl, $C_1$-$C_4$-alkynyl, aryl or hetaryl.

Very particular preference is given to compounds of the formulae (I) and (II)

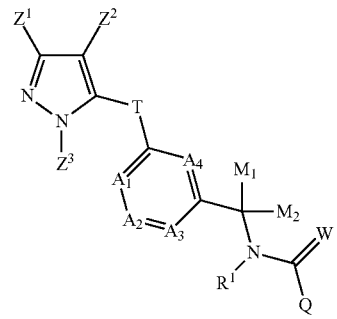

(I)

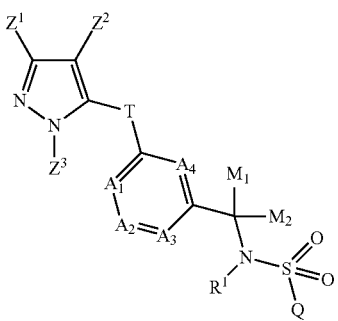

(II)

in which $R^1$ represents hydrogen or represents $C_1$-$C_4$-alkyl, $C_3$-$C_4$-alkenyl, $C_3$-$C_4$-alkynyl, $C_3$-$C_6$-cycloalkyl, $C_1$-$C_4$-alkylcarbonyl, $C_1$-$C_4$-alkoxycarbonyl, aryl-($C_1$-$C_2$)-alkyl, heteroaryl-($C_1$-$C_2$)-alkyl which are optionally mono- to pentasubstituted independently of one another by fluorine, chlorine, cyano, $C_1$-$C_4$-alkoxy and $C_1$-$C_4$-alkoxycarbonyl, $M^1$ represents hydrogen, $M^2$ represents hydrogen or represents $C_1$-$C_3$-alkyl, $C_2$-$C_6$-alkenyl, $C_3$-$C_6$-cycloalkyl, $C_1$-$C_3$-alkoxycarbonyl which are optionally mono- to pentasubstituted independently of one another by halogen, cyano, alkoxy and alkoxycarbonyl, $M^1$ and $M^2$ with the carbon atom to which they are attached form an optionally substituted 3-membered ring, the chemical groupings $A_1$ represents $CR^2$ or nitrogen, $A_2$ represents $CR^3$ or nitrogen, $A_3$ represents $CR^4$ or nitrogen and $A_4$ represents $CR^5$ or nitrogen, but where not more than three of the chemical groupings $A_1$ to $A_4$ simultaneously represent nitrogen;

$R^2$, $R^3$, $R^4$ and $R^5$ independently of one another represent hydrogen, fluorine, chlorine, bromine, cyano, nitro, or represent $C_1$-$C_4$-alkyl, $C_3$-$C_6$-cycloalkyl, $C_1$-$C_4$-alkoxy, N—$C_1$-$C_4$-alkoxyimino-$C_1$-$C_2$-alkyl, $C_1$-$C_4$-alkylsulphanyl, $C_1$-$C_4$-alkylsulphinyl, $C_1$-$C_4$-alkylsulphonyl, N—$C_1$-$C_4$-alkylamino or N,N-di-$C_1$-$C_4$-alkylamino which are optionally independently of one another mono- to pentasubstituted by hydroxy, nitro, amino, fluorine, chlorine, $C_1$-$C_4$-alkoxy, cyano, hydroxycarbonyl;

W represents oxygen or sulphur;

Q represents hydrogen, amino or represents one of the groupings $C_1$-$C_4$-alkyl, $C_2$-$C_6$-alkenyl, $C_2$-$C_6$-alkynyl, $C_3$-$C_6$-cycloalkyl, $C_2$-$C_5$-heterocycloalkyl, $C_1$-$C_4$-alkoxy, $C_3$-$C_6$-cycloalkyl-$C_1$-$C_6$-alkyl, aryl-($C_1$-$C_3$)-alkyl, heteroaryl-($C_1$-$C_3$)-alkyl, N—$C_1$-$C_4$-alkylamino, N—$C_1$-$C_4$-alkylcarbonylamino or N,N-di-$C_1$-$C_4$-alkylamino which are optionally independently of one another mono- to pentasubstituted by hydroxy, nitro, amino, halogen, $C_1$-$C_4$-alkyl, $C_1$-$C_4$-alkoxy, cyano, hydroxycarbonyl, $C_1$-$C_4$-alkoxycarbonyl, $C_1$-$C_4$-alkylcarbamoyl, $C_3$-$C_6$-cycloalkylcarbamoyl, phenyl; or Q represents aryl substituted by 0, 1, 2, 3 or 4 substituents V or a 5- or 6-membered heteroaromatic substituted by 0, 1, 2, 3 or 4 substituents V, where V independently of one another represent fluorine, chlorine, bromine, iodine, cyano, nitro or represent $C_1$-$C_6$-alkyl, $C_2$-$C_4$-alkenyl, $C_2$-$C_4$-alkynyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulphanyl, $C_1$-$C_6$-alkylsulphinyl, $C_1$-$C_6$-alkylsulphonyl, N,N-di-($C_1$-$C_6$-alkyl)amino which are optionally independently of one another mono- to pentasubstituted by hydroxy, nitro, amino, fluorine, chlorine, bromine, iodine, $C_1$-$C_4$-alkyl, $C_1$-$C_4$-alkoxy, cyano, hydroxycarbonyl;

T represents one of the 5-membered heteroaromatics T1-T8 listed below, where the bond to the pyrazole head group is marked with an asterisk,

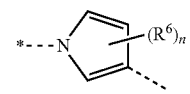

T1

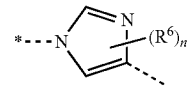

T2

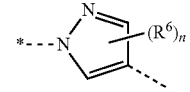

T3

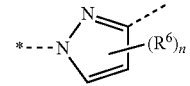

T4

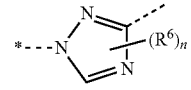

T5

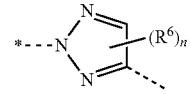

T6

-continued

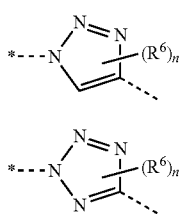

where
R⁶ independently of one another represent fluorine, chlorine, cyano, nitro, amino or represents $C_1$-$C_6$-alkyl, $C_1$-$C_6$-alkoxy, $C_1$-$C_6$-alkylcarbonyl, $C_1$-$C_6$-alkylsulphanyl, $C_1$-$C_6$-alkylsulphinyl, $C_1$-$C_6$-alkylsulphonyl which are optionally mono- to pentasubstituted by fluorine and/or chlorine, and n represents the values 0-1;

$Z^1$ represents $C_1$-$C_4$-haloalkyl, $C_3$-$C_6$-halocycloalkyl optionally mono- to disubstituted by $C_1$-$C_4$-alkoxy, cyano, hydroxycarbonyl, $C_1$-$C_4$-alkoxycarbonyl, $C_1$-$C_4$-alkylcarbamoyl, $C_3$-$C_6$-cycloalkylcarbamoyl, phenyl, and $Z^2$ represents hydrogen, fluorine, chlorine, bromine, iodine, cyano, nitro, amino or represents $C_1$-$C_4$-alkyl, $C_1$-$C_4$-alkylcarbonyl, $C_1$-$C_4$-alkylsulphanyl, $C_1$-$C_4$-alkylsulphinyl, $C_1$-$C_4$-alkylsulphonyl which are optionally independently of one another mono- to trisubstituted by hydroxy, nitro, amino, fluorine, chlorine, $C_1$-$C_4$-alkoxy, cyano, hydroxycarbonyl, $C_1$-$C_4$-alkoxycarbonyl, $C_1$-$C_4$-alkylcarbamoyl, $C_3$-$C_6$-cycloalkylcarbamoyl, phenyl, and $Z^3$ represents hydrogen or represents $C_1$-$C_4$-alkyl, $C_3$-$C_6$-cycloalkyl, $C_3$-$C_4$-alkenyl, $C_3$-$C_4$-alkynyl, phenyl and hetaryl which are optionally independently of one another mono- to trisubstituted by hydroxy, nitro, amino, $C_1$-$C_4$-alkoxy, cyano, fluorine, chlorine, hydroxycarbonyl, $C_1$-$C_4$-alkoxycarbonyl, $C_1$-$C_4$-alkylcarbamoyl, $C_3$-$C_6$-cycloalkylcarbamoyl, phenyl.

Especially preferred are compounds of the formulae (I) and (II)

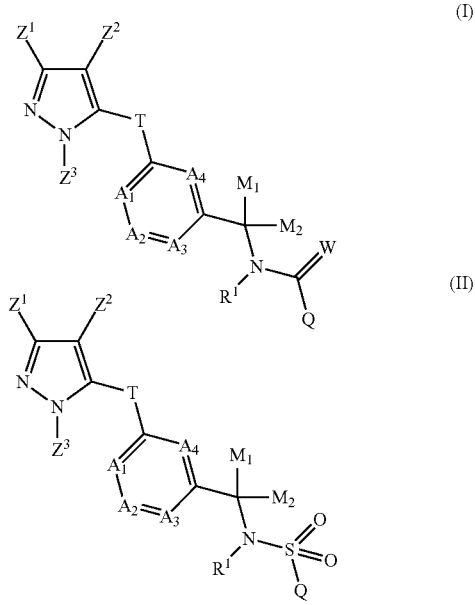

in which
$R^1$ represents hydrogen, methyl, ethyl, n-propyl, isopropyl, n-butyl, isobutyl, s-butyl, t-butyl, methoxymethyl, ethoxymethyl, propoxymethyl, methylcarbonyl, ethylcarbonyl, n-propylcarbonyl, isopropylcarbonyl, n-butylcarbonyl, isobutylcarbonyl, s-butylcarbonyl, t-butylcarbonyl, methoxycarbonyl, ethoxycarbonyl, n-propoxycarbonyl, isopropoxycarbonyl, n-butoxycarbonyl, isobutoxycarbonyl, s-butoxycarbonyl, t-butoxycarbonyl, cyanomethyl, 2-cyanoethyl, benzyl, 4-methoxybenzyl, pyrid-2-ylmethyl, pyrid-3-ylmethyl, pyrid-4-ylmethyl, 6-chloropyrid-3-ylmethyl;

$M^1$ represents hydrogen,
$M^2$ represents hydrogen, methyl, ethyl, difluoromethyl, trichloromethyl, dichlorofluoromethyl, trifluoromethyl, cyclopropyl, cyclobutyl, methoxycarbonyl, ethoxycarbonyl, $M^1$ and $M^2$ with the carbon atom to which they are attached form a 3-membered carbocycle, the chemical groupings
$A_1$ represents $CR^2$ or nitrogen,
$A_2$ represents $CR^3$ or nitrogen,
$A_3$ represents $CR^4$ or nitrogen and
$A_4$ represents $CR^5$ or nitrogen, but where not more than three of the chemical groupings $A_1$ to $A_4$ simultaneously represent nitrogen;

$R^2$ and $R^5$ independently of one another represent hydrogen, methyl, fluorine or chlorine and $R^3$ and $R^4$ independently of one another represent hydrogen, fluorine, chlorine, bromine, iodine, cyano, nitro, methyl, ethyl, fluoromethyl, difluoromethyl, chlorodifluoromethyl, trifluoromethyl, 2,2,2-trifluoroethyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, trifluoromethylsulphanyl, methylsulphonyl, methylsulphinyl, trifluoromethylsulphonyl, trifluoromethylsulphinyl;

W represents oxygen or sulphur;

Q represents hydrogen, methyl, ethyl, n-propyl, isopropyl, t-butyl, 1-methylpropyl, n-butyl, 2-methylpropyl, 2-methylbutyl, hydroxymethyl, 2-hydroxyethyl, 2-hydroxypropyl, cyanomethyl, 2-cyanoethyl, trifluoromethyl, 1-fluoroethyl, 2-fluoroethyl, 2,2-difluoroethyl, 2,2,2-trifluoroethyl, 1-trifluoromethylethyl, 2,2-difluoropropyl, 3,3,3-trifluoropropyl, 2,2-dimethyl-3-fluoropropyl, cyclopropyl, 1-cyanocyclopropyl, cyclopropylmethyl, cyclobutyl, cyclopentyl, cyclohexyl, 1-cyclopropylethyl, bis(cyclopropyl)methyl, 2,2-dimethylcyclopropylmethyl, 2-phenylcyclopropyl, 2,2-dichlorocyclopropyl, trans-2-chlorocyclopropyl, cis-2-chlorocyclopropyl, 2,2-difluorocyclopropyl, trans-2-fluorocyclopropyl, cis-2-fluorocyclopropyl, trans-4-hydroxycyclohexyl, 4-trifluoromethylcyclohexyl, ethenyl, 1-methylethenyl, prop-1-enyl, 2-methylprop-1-enyl, 3-methylbut-1-enyl, 3,3,3-trifluoroprop-1-enyl, 1-ethylethenyl, 1-methylprop-1-enyl, prop-2-ynyl, 3-fluoroprop-2-enyl, oxetan-3-yl, thietan-3-yl, 1-oxidothietan-3-yl, 1,1-dioxidothietan-3-yl, tetrahydrofuran-3-yl, 1,1-dioxidotetrahydrothiophen-3-yl, isoxazol-3-ylmethyl, 1,2,4-triazol-3-ylmethyl, 3-methyloxetan-3-ylmethyl, benzyl, 2,6-difluorophenylmethyl, 3-fluorophenylmethyl, 2-fluorophenylmethyl, 2,5-difluorophenylmethyl, 1-phenylethyl, 4-chlorophenylethyl, 2-trifluoromethylphenylethyl, 1-pyridin-2-ylethyl, pyridin-2-ylmethyl, 5-fluoropyridin-2-ylmethyl, (6-chloropyridin-3-yl)methyl, pyrimidin-2-ylmethyl, thiophen-2-yl-methyl, 2-ethoxyethyl, 2-methoxyethyl, 1-(methylsulphanyl)ethyl, 2-(methylsulphanyl)ethyl, 1-methyl-2-(ethylsulphanyl)ethyl, 2-methyl-1-(methylsulphanyl)propan-2-yl, methoxycarbonyl, ethoxycarbonyl, methoxycarbonylmethyl, NH$_2$, N-ethylamino, N-allylamino, N,N-dimethylamino, N,N-diethylamino, methoxy, ethoxy, propoxy, isopropoxy, tert-butoxy; or Q represents phenyl, naphthyl, pyridazine, pyrazine, pyrimidine, triazine, pyridine, pyrazole, thiazole, isothiazole, oxazole, isoxazole, triazole, imidazole, furan, thiophene, pyrrole, oxadiazole, thiadiazole substituted by 0, 1, 2 or 3 substituents V, where V independently of one another represent fluorine, chlorine, bromine, iodine, cyano, nitro, methyl, ethyl, difluoromethyl, trichloromethyl, chlorodifluoromethyl, dichlorofluoromethyl, trifluoromethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, heptafluoro-n-propyl, heptafluoroisopropyl, nonafluoro-n-butyl, cyclopropyl, cyclobutyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, methylsulphonyl, methylsulphinyl, trifluoromethylsulphonyl, trifluoromethylsulphinyl, trifluoromethylsulphanyl, N,N-dimethylamino;

T represents one of the 5-membered heteroaromatics T1-T8 listed below, where the bond to the pyrazole head group is marked with an asterisk,

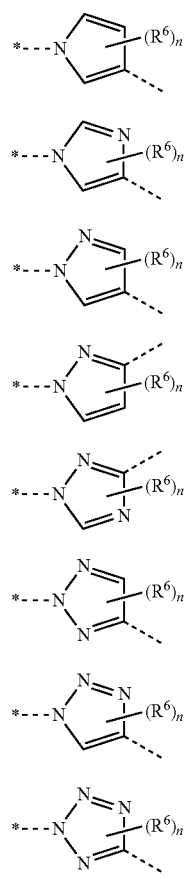

where

R$^6$ independently of one another represent fluorine, chlorine, cyano, nitro, amino, methyl, ethyl, propyl, 1-methylethyl, tert-butyl, trifluoromethyl, difluoromethyl, methoxy, ethoxy, trifluoromethoxy, 2,2-difluoroethoxy, 2,2,2-trifluoroethoxy, methylcarbonyl, ethylcarbonyl, trifluoromethylcarbonyl, methylsulphanyl, methylsulphinyl, methylsulphonyl, trifluoromethylsulphonyl, trifluoromethylsulphanyl, trifluoromethylsulphinyl, and n represents the values 0-1;

Z$^1$ represents difluoromethyl, trichloromethyl, chlorodifluoromethyl, dichlorofluoromethyl, trifluoromethyl, bromodichloromethyl, 1-fluoroethyl, 1-fluoro-1-methylethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, heptafluoro-n-propyl, heptafluoroisopropyl, nonafluoro-n-butyl, cyclopropyl, 1-chlorocyclopropyl, 1-fluorocyclopropyl, 1-bromocyclopropyl, 1-cyanocyclopropyl, 1-trifluoromethylcyclopropyl, cyclobutyl or 2,2-difluoro-1-methylcyclopropyl, and Z$^2$ represents hydrogen, fluorine, chlorine, bromine, iodine, cyano, nitro, amino, methyl, ethyl, 1,1-t-butyl, difluoromethyl, trichloromethyl, chlorodifluoromethyl, dichlorofluoromethyl, trifluoromethyl, bromodichloromethyl, 1-fluoroethyl, 1-fluoro-1-methylethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, heptafluoro-n-propyl, heptafluoroisopropyl, nonafluoro-n-butyl, methylsulphanyl, methylsulphinyl, methylsulphonyl, ethylthio, ethylsulphinyl, ethylsulphonyl, trifluoromethylsulphanyl, trifluoromethylsulphinyl, trifluoromethylsulphonyl, chlorodifluoromethylsulphanyl, chlorodifluoromethylsulphinyl, chlorodifluoromethylsulphonyl, dichlorofluoromethylsulphanyl, dichlorofluoromethylsulphinyl, dichlorofluoromethylsulphonyl and Z$^3$ represents hydrogen, methyl, ethyl, n-propyl, isopropyl, n-butyl, isobutyl, s-butyl, t-butyl, 1-propenyl, 1-propynyl, 1-butyryl, difluoromethyl, trichloromethyl, chlorodifluoromethyl, dichlorofluoromethyl, trifluoromethyl, 1-fluoroethyl, 1-fluoro-1-methylethyl, 2-fluoroethyl, 2,2-difluoroethyl, 2,2,2-trifluoroethyl, phenyl, 2-chlorophenyl, 3-chlorophenyl, 4-chlorophenyl, 2,4-dichlorophenyl, 2,5-dichlorophenyl, 3,4-dichlorophenyl, 2,6-dichlorophenyl, 2,6-dichloro-4-trifluoromethylphenyl, 3-chloro-5-trifluoromethylpyridin-2-yl.

Special preference is furthermore also given to compounds of the formulae (I) and (II) in which the radicals below are alternatively defined as follows:

R$^1$ represents hydrogen, methyl, ethyl, n-propyl, isopropyl, n-butyl, isobutyl, s-butyl, t-butyl, methoxymethyl, ethoxymethyl, propoxymethyl, methylcarbonyl, ethylcarbonyl, n-propylcarbonyl, isopropylcarbonyl, s-butylcarbonyl, t-butylcarbonyl, methoxycarbonyl, ethoxycarbonyl, n-propoxycarbonyl, isopropoxycarbonyl, s-butoxycarbonyl, t-butoxycarbonyl, cyanomethyl, 2-cyanoethyl, benzyl, 4-methoxybenzyl, pyrid-2-ylmethyl, pyrid-3-ylmethyl, pyrid-4-ylmethyl, 6-chloropyrid-3-ylmethyl;

M$^2$ represents hydrogen, C$_1$-C$_3$-alkyl, C$_2$-C$_3$-alkenyl, C$_3$-C$_6$-cycloalkyl, C$_1$-C$_3$-alkoxycarbonyl, cyano or cyano-C$_1$-C$_2$-alkyl, Q represents hydrogen, methyl, ethyl, n-propyl, 1-methylethyl, 1,1-dimethylethyl, 1-methylpropyl, n-butyl, 2-methylpropyl, 2-methylbutyl, hydroxymethyl, 2-hydroxypropyl, cyanomethyl, 2-cyanoethyl, 2-fluoroethyl, 2,2-difluoroethyl, 2,2,2-trifluoroethyl, 1-trifluoromethylethyl, 2,2-difluoropropyl, 3,3,3-trifluoropropyl, 2,2-dimethyl-3-fluoropropyl, cyclopropyl, 1-cyanocyclopropyl, 1-methoxycarbonylcyclopropyl, 1-(N-methylcarbamoyl)cyclopropyl, 1-(N-cyclopropylcarbamoyl)cyclopropyl, cyclopropylmethyl, cyclobutyl, cyclopentyl, cyclohexyl, 1-cyclopropylethyl, bis(cyclopropyl)methyl, 2,2-dimethylcyclopropylmethyl, 2-phenylcyclopropyl, 2,2-dichlorocyclopropyl, trans-2-chlorocyclopropyl, cis-2-chlorocyclopropyl, 2,2-difluorocyclopropyl, trans-2-fluorocyclopropyl, cis-2-fluorocyclopropyl, trans-4-hydroxycyclohexyl, 4-trifluoromethylcyclohexyl, prop-2-enyl, 2-methylprop-2-enyl, prop-2-ynyl, 1,1-dimethylbut-2-ynyl, 3-chloroprop-2-enyl, 3,3-dichloroprop-2-enyl, 3,3-dichloro-1,1-dimethylprop-2-enyl, phenyl, 2-chlorophenyl, 3-chlorophenyl, 4-chlorophenyl, oxetan-3-yl, thietan-3-yl, 1-oxidothietan-3-yl, 1,1-dioxidothietan-3-yl, isoxazol-3-ylmethyl, 1,2,4-triazol-3-ylmethyl, 3-methyloxetan-3-ylmethyl, benzyl, 2,6-difluorophenylmethyl, 3-fluorophenylmethyl, 2-fluorophenylmethyl, 2,5-difluorophenylmethyl, 1-phenylethyl, 4-chlorophenylethyl, 2-trifluormethylphenylethyl, 1-pyridin-2-ylethyl, pyridin-2-ylmethyl, 5-fluoropyridin-2-ylmethyl, (6-chloropyridin-3-yl)methyl, pyrimidin-2-ylmethyl, methoxy, 2-ethoxyethyl, 2-(methylsulphanyl)ethyl, 1-methyl-2-(ethylsulphanyl)ethyl, 2-methyl-1-(methylsulphanyl)propan-2-yl, methoxycarbonyl, methoxycarbonylmethyl, NH$_2$, N-ethylamino, N-allylamino, N,N-dimethylamino, N,N-diethylamino; or Q represents phenyl, naphthyl, pyridazine, pyrazine, pyrimidine, triazine, pyridine, pyrazole, thiazole, isothiazole, oxazole, isoxazole, triazole, imidazole, furan, thiophene, pyrrole, oxadiazole, thiadiazole substituted by 0-4 substituents V, where V independently of one another represent fluorine, chlorine, bromine, iodine, cyano, nitro, methyl, ethyl, difluoromethyl, trichloromethyl, chlorodifluoromethyl, dichlorofluoromethyl, trifluoromethyl, chloromethyl, bromomethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-tert-butyl, heptafluoro-n-propyl, heptafluoroisopropyl, nonafluoro-n-butyl, cyclopropyl, cyclobutyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, methylsulphonyl, methylsulphinyl, trifluoromethylsulphonyl, trifluoromethylsulphinyl, trifluoromethylsulphanyl, N,N-dimethylamino;

R$^6$ independently of one another represent halogen, cyano, nitro, amino, methyl, ethyl, 1-methylethyl, tert-butyl, trifluoromethyl, difluoromethyl, methoxy, ethoxy, trifluoromethoxy, 2,2-difluoroethoxy, 2,2,2-trifluoroethoxy, methylcarbonyl, ethylcarbonyl, trifluoromethylcarbonyl, methylsulphanyl, methylsulphinyl, methylsulphonyl, trifluoromethylsulphonyl, trifluoromethylsulphanyl, trifluoromethylsulphinyl, and n represents the values 0-1;

Z$^1$ represents methyl, ethyl, 1,1-dimethylethyl, difluoromethyl, trichloromethyl, chlorodifluoromethyl, dichlorofluoromethyl, trifluoromethyl, bromodichloromethyl, chloromethyl, bromomethyl, 1-fluoroethyl, 1-fluoro-1-methylethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-tert-butyl, heptafluoro-n-propyl, heptafluoroisopropyl, nonafluoro-n-butyl, cyclopropyl, 1-chlorocyclopropyl, 1-fluorocyclopropyl, 1-bromocyclopropyl, 1-cyanocyclopropyl, 1-trifluoromethylcyclopropyl, cyclobutyl and 2,2-difluoro-1-methylcyclopropyl, and Z$^2$ represents hydrogen, halogen, cyano, nitro, amino, methyl, ethyl, 1,1-dimethylethyl, difluoromethyl, trichloromethyl, chlorodifluoromethyl, dichlorofluoromethyl, trifluoromethyl, bromodichloromethyl, chloromethyl, bromomethyl, 1-fluoroethyl, 1-fluoro-1-methylethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-t-butyl, heptafluoro-n-propyl, heptafluoroisopropyl, nonafluoro-n-butyl, methylsulphanyl, methylsulphinyl, methylsulphonyl, ethylthio, ethylsulphinyl, ethylsulphonyl, trifluoromethylsulphanyl, trifluoromethylsulphinyl, trifluoromethylsulphonyl, chlorodifluoromethylsulphanyl, chlorodifluoromethylsulphinyl, chlorodifluoromethylsulphonyl, dichlorofluoromethylsulphanyl, dichlorofluoromethylsulphinyl, dichlorofluoromethylsulphonyl and Z$^3$ represents hydrogen, methyl, ethyl, n-propyl, isopropyl, n-butyl, isobutyl, s-butyl, t-butyl, ethenyl, 1-propenyl, 2-propenyl, 1-propynyl, 1-butynyl, difluoromethyl, trichloromethyl, chlorodifluoromethyl, dichlorofluoromethyl, trifluoromethyl, chloromethyl, bromomethyl, 1-fluoroethyl, 1-fluoro-1-methylethyl, 2-fluoroethyl, 2,2-difluoroethyl, 2,2,2-trifluoroethyl, phenyl, 2-chlorophenyl, 3-chlorophenyl, 4-chlorophenyl, 2,5-dichlorophenyl, 3,4-dichlorophenyl, 2,6-dichlorophenyl, 2,6-dichloro-4-trifluoromethylphenyl, 3-chloro-5-trifluoromethylpyridin-2-yl.

Very especially preferred compounds for the purpose of the invention are those of the general formulae (I) and (II) in which Z$^1$ represents trifluoromethyl, 1-chlorocyclopropyl, 1-fluorocyclopropyl or pentafluoroethyl, Z$^2$ represents trifluoromethyl, nitro, methylsulphanyl, methylsulphinyl, methylsulphonyl, fluorine, chlorine, bromine, cyano or iodine, Z$^3$ represents methyl, ethyl, n-propyl or hydrogen, R$^1$ represents hydrogen, methyl, ethyl, n-propyl, isopropyl, n-butyl, isobutyl, s-butyl, t-butyl, methoxymethyl, ethoxymethyl, propoxymethyl, methylcarbonyl, ethylcarbonyl, n-propylcarbonyl, isopropylcarbonyl, n-butylcarbonyl, isobutylcarbonyl, s-butylcarbonyl, t-butylcarbonyl, methoxycarbonyl, ethoxycarbonyl, n-propoxycarbonyl, isopropoxycarbonyl, n-butoxycarbonyl, isobutoxycarbonyl, s-butoxycarbonyl, t-butoxycarbonyl, cyanomethyl, 2-cyanoethyl, benzyl, 4-methoxybenzyl, pyrid-2-ylmethyl, pyrid-3-ylmethyl, pyrid-4-ylmethyl, 6-chloropyrid-3-ylmethyl, M$^1$ represents hydrogen;

M$^2$ represents hydrogen or methyl;

M$^1$ and M$^2$ with the carbon atom to which they are attached form a 3-membered carbocycle, A$^1$ and A$^4$ represent CH, A$^2$ represents CH or N, A$_3$ represents CR$^4$ and R$^4$ represents methyl, ethyl, fluorine, chlorine, bromine or iodine, T represents one of the 5-membered heteroaromatics T1-T8 listed below, where the bond to the pyrazole head group is marked with an asterisk,

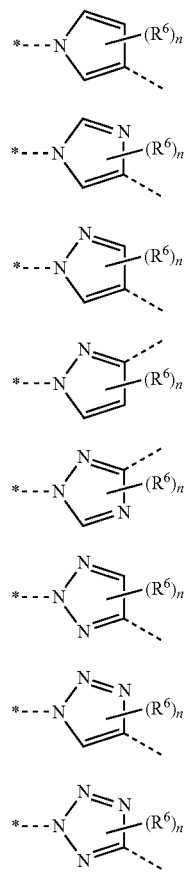

where
R⁶ represents hydrogen, methyl, ethyl, 2-methylethyl, 2,2-dimethylethyl, fluorine, chlorine, bromine, iodine, nitro, trifluoromethyl, amino,
W represents oxygen and
Q represents hydrogen, methyl, ethyl, n-propyl, 1-methylethyl, 1,1-dimethylethyl, n-butyl, 1-methylpropyl, 2-methylpropyl, 2-methylbutyl, hydroxymethyl, 2-hydroxypropyl, cyanomethyl, 2-cyanoethyl, 2-fluoroethyl, 2,2-difluoroethyl, 2,2,2-trifluoroethyl, 1-trifluoromethylethyl, 2,2-difluoropropyl, 3,3,3-trifluoropropyl, 2,2-dimethyl-3-fluoropropyl, cyclopropyl, cyclopropylmethyl, cyclobutyl, cyclopentyl, cyclohexyl, 1-cyclopropylethyl, bis(cyclopropyl)methyl, 2,2-dimethylcyclopropylmethyl, 2-phenylcyclopropyl, 2,2-dichlorocyclopropyl, trans-2-chlorocyclopropyl, cis-2-chlorocyclopropyl, 2,2-difluorocyclopropyl, trans-2-fluorocyclopropyl, cis-2-fluorocyclopropyl, trans-4-hydroxycyclohexyl, 4-trifluoromethylcyclohexyl, ethenyl, 1-methylethenyl, prop-1-enyl, 2-methylprop-1-enyl, 3-methylbut-1-enyl, 3,3,3-trifluoroprop-1-enyl, 1-ethylethenyl, 1-methylprop-1-enyl, prop-2-ynyl, 3-fluoroprop-2-enyl, oxetan-3-yl, thietan-3-yl, 1-oxidothietan-3-yl, 1,1-dioxidothietan-3-yl, isoxazol-3-ylmethyl, 1,2,4-triazol-3-ylmethyl, 3-methyloxetan-3-ylmethyl, benzyl, 2,6-difluorophenylmethyl, 3-fluorophenylmethyl, 2-fluorophenylmethyl, 2,5-difluorophenylmethyl, 1-phenylethyl, 4-chlorophenylethyl, 2-trifluormethylphenylethyl, 1-pyridin-2-ylethyl, pyridin-2-ylmethyl, (6-chloropyridin-3-yl)methyl, 5-fluoropyridin-2-ylmethyl, pyrimidin-2-ylmethyl, methoxy, 2-ethoxyethyl, 2-(methylsulphanyl)ethyl, 1-methyl-2-(ethylsulphanyl)ethyl, 2-methyl-1-(methylsulphanyl)propan-2-yl, methoxycarbonyl, methoxycarbonylmethyl, NH₂, N-ethylamino, N-allylamino, N,N-dimethylamino, N,N-diethylamino, methoxy, ethoxy, propoxy, isopropoxy, tert-butoxy; or
Q represents phenyl, naphthyl, pyridazine, pyrazine, pyrimidine, triazine, pyridine, pyrazole, thiazole, isothiazole, oxazole, isoxazole, triazole, imidazole, furan, thiophene, pyrrole, oxadiazole, thiadiazole substituted by 0, 1, 2 or 3 substituents V, where
V independently of one another represent fluorine, chlorine, bromine, iodine, cyano, nitro, methyl, ethyl, difluoromethyl, trichloromethyl, chlorodifluoromethyl, dichlorofluoromethyl, trifluoromethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, heptafluoro-n-propyl, heptafluoroisopropyl, nonafluoro-n-butyl, cyclopropyl, cyclobutyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, methylsulphonyl, methylsulphinyl, trifluoromethylsulphonyl, trifluoromethylsulphinyl, trifluoromethylsulphanyl, N,N-dimethylamino.

Very especially preferred compounds are furthermore also those in which the radicals below are alternatively defined as follows:
R¹ represents hydrogen, methyl, ethyl, n-propyl, isopropyl, n-butyl, isobutyl, s-butyl, t-butyl, methoxymethyl, ethoxymethyl, propoxymethyl, methylcarbonyl, ethylcarbonyl, n-propylcarbonyl, isopropylcarbonyl, s-butylcarbonyl, t-butylcarbonyl, methoxycarbonyl, ethoxycarbonyl, n-propoxycarbonyl, isopropoxycarbonyl, s-butoxycarbonyl, t-butoxycarbonyl, cyanomethyl, 2-cyanoethyl, benzyl, 4-methoxybenzyl, pyrid-2-ylmethyl, pyrid-3-ylmethyl, pyrid-4-ylmethyl, 6-chloropyrid-3-ylmethyl,
A¹, A² and A⁴ represent CH,
R⁴ represents fluorine, chlorine, bromine or iodine,
Q represents hydrogen, methyl, ethyl, n-propyl, 1-methylethyl, 1,1-dimethylethyl, n-butyl, 1-methylpropyl, 2-methylpropyl, 2-methylbutyl, hydroxymethyl, 2-hydroxypropyl, cyanomethyl, 2-cyanoethyl, 2-fluoroethyl, 2,2-difluoroethyl, 2,2,2-trifluoroethyl, 1-trifluoromethylethyl, 2,2-difluoropropyl, 3,3,3-trifluoropropyl, 2,2-dimethyl-3-fluoropropyl, cyclopropyl, 1-cyanocyclopropyl, 1-methoxycarbonylcyclopropyl, 1-(N-methylcarbamoyl)cyclopropyl, 1-(N-cyclopropylcarbamoyl)cyclopropyl, cyclopropylmethyl, cyclobutyl, cyclopentyl, cyclohexyl, 1-cyclopropylethyl, bis(cyclopropyl)methyl, 2,2-dimethylcyclopropylmethyl, 2-phenylcyclopropyl, 2,2-dichlorocyclopropyl, trans-2-chlorocyclopropyl, cis-2-chlorocyclopropyl, 2,2-difluorocyclopropyl, trans-2-fluorocyclopropyl, cis-2-fluorocyclopropyl, trans-4-hydroxycyclohexyl, 4-trifluoromethylcyclohexyl, prop-2-enyl, 2-methylprop-2-enyl, prop-2-ynyl, 1,1-dimethylbut-2-ynyl, 3-chloroprop-2-enyl, 3,3-dichloroprop-2-enyl, 3,3-dichloro-1,1-dimethylprop-2-enyl, phenyl, 2-chlorophenyl, 3-chlorophenyl, 4-chlorophenyl, oxetan-3-yl, thietan-3-yl, 1-oxidothietan-3-yl, 1,1-dioxidothietan-3-yl, isoxazol-3-ylmethyl, 1,2,4-triazol-3-ylmethyl, 3-methyloxetan-3-ylmethyl, benzyl, 2,6-difluorophenylmethyl, 3-fluorophenylmethyl, 2-fluorophenylmethyl, 2,5-difluorophenylmethyl, 1-phenylethyl, 4-chlorophenylethyl, 2-trifluormethylphenylethyl, 1-pyridin-2-ylethyl, pyridin-2-ylmethyl, (6-chloropyridin-3-yl)methyl, 5-fluoropyridin-2-ylmethyl, pyrimidin-2-ylmethyl, methoxy, 2-ethoxyethyl, 2-(methylsulphanyl)ethyl, 1-methyl-2-(ethylsulphanyl)ethyl, 2-methyl-1-(methylsulphanyl)propan-2-yl, methoxycarbonyl, methoxycarbonylmethyl, NH$_2$, N-ethylamino, N-allylamino, N,N-dimethylamino, N,N-diethylamino; or Q represents phenyl, naphthyl, pyridazine, pyrazine, pyrimidine, triazine, pyridine, pyrazole, thiazole, isothiazole, oxazole, isoxazole, triazole, imidazole, furan, thiophene, pyrrole, oxadiazole, thiadiazole substituted by 0-4 substituents V, where V independently of one another represent fluorine, chlorine, bromine, iodine, cyano, nitro, methyl, ethyl, difluoromethyl, trichloromethyl, chlorodifluoromethyl, dichlorofluoromethyl, trifluoromethyl, chloromethyl, bromomethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-tert-butyl, heptafluoro-n-propyl, heptafluoroisopropyl, nonafluoro-n-butyl, cyclopropyl, cyclobutyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, methylsulphonyl, methylsulphinyl, trifluoromethylsulphonyl, trifluoromethylsulphinyl, trifluoromethylsulphanyl, N,N-dimethylamino;

Especially emphasized compounds for the purpose of the invention are those of the general formulae (Ia), (Ib), (Ic), (Id), (Ie), (If), (Ig), (Ih) in which the radicals A$_1$-A$_4$, n, W, Q, R$^1$, R$^6$, M$^1$, M$^2$ and Z$^1$-Z$^3$ have the meanings given above.

(Ia)
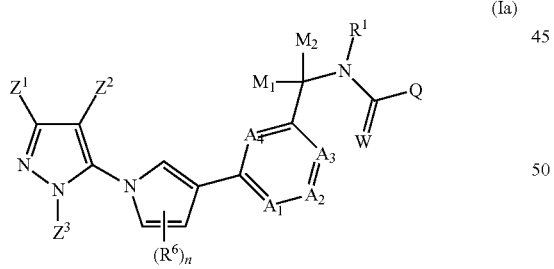

(Ib)
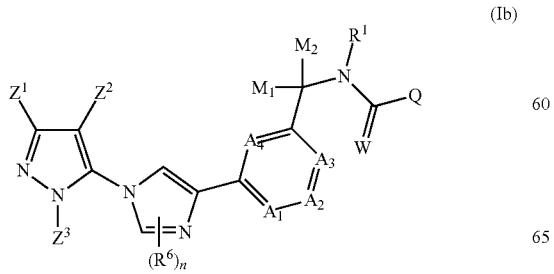

(Ic)
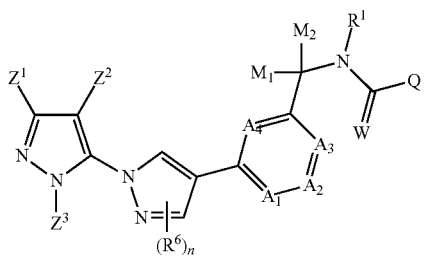

(Id)
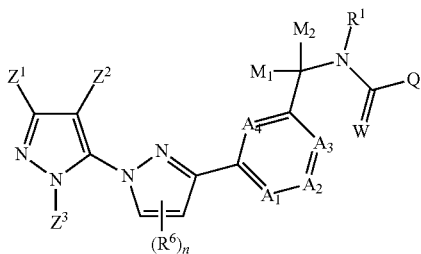

(Ie)
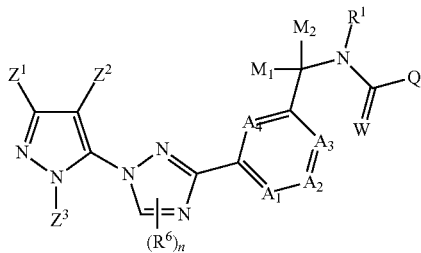

(If)
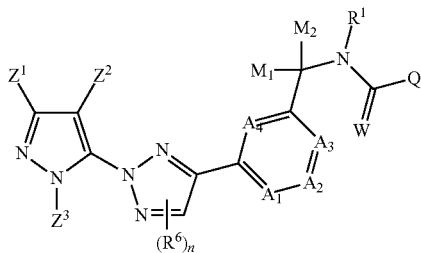

(Ig)
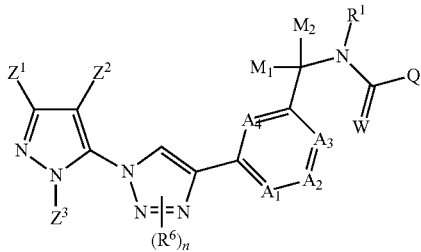

(Ih)
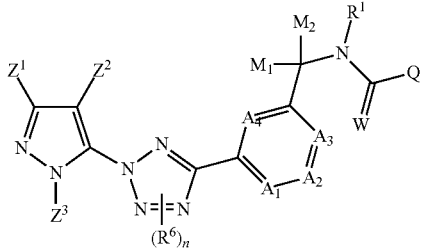

Especially emphasized compounds for the purpose of the invention are furthermore those of the general formulae (IIa), (IIb), (IIc), (IId), (IIe), (IIf), (IIg), (IIh) in which the radicals $A_1$-$A_4$, n, W, Q, $R^1$, $R^6$, $M^1$, $M^2$ and $Z^1$-$Z^3$ have the meanings given above.

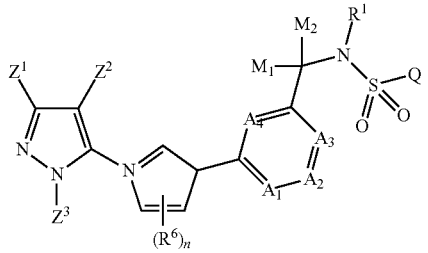
(IIa)

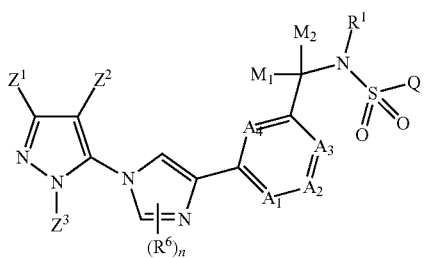
(IIb)

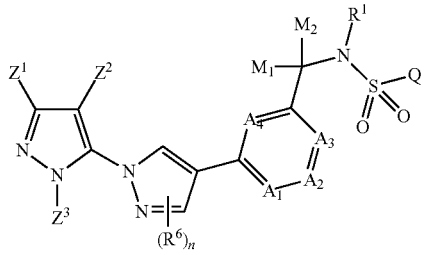
(IIc)

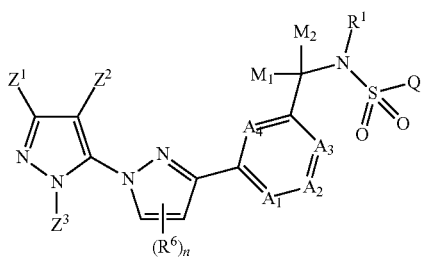
(IId)

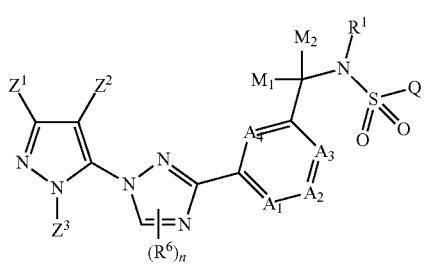
(IIe)

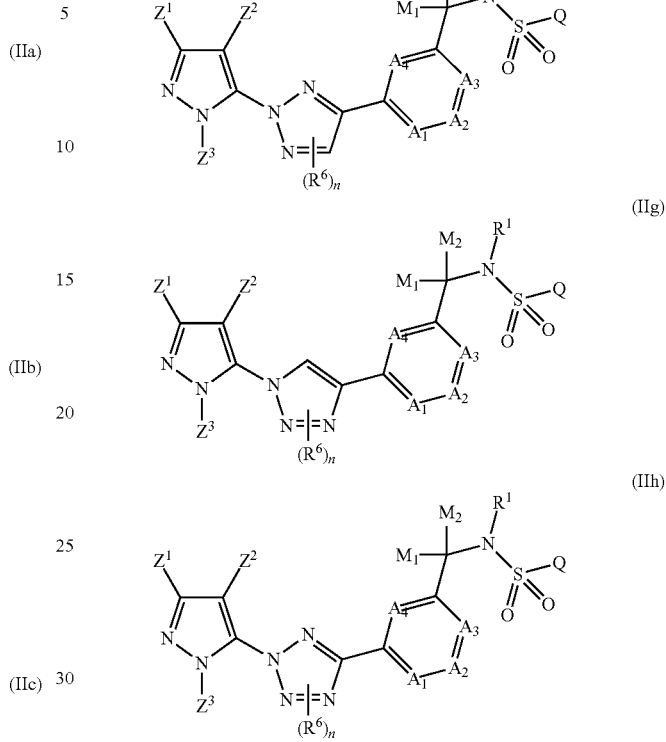
(IIf)
(IIg)
(IIh)

According to the invention, "alkyl"—on its own or as part of a chemical group—represents straight-chain or branched hydrocarbons preferably having 1 to 6 carbon atoms such as, for example, methyl, ethyl, n-propyl, isopropyl, n-butyl, isobutyl, s-butyl, t-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, 2-methylpentyl, 3-methylpentyl, 4-methylpentyl, 1,2-dimethylpropyl, 1,3-dimethylbutyl, 1,4-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl and 2-ethylbutyl. Preference is furthermore given to alkyl groups having 1 to 4 carbon atoms such as, inter alia, methyl, ethyl, n-propyl, isopropyl, n-butyl, isobutyl, s-butyl or t-butyl. The alkyl groups according to the invention may be substituted by one or more identical or different radicals.

According to the invention, "alkenyl"—on its own or as part of a chemical group—represents straight-chain or branched hydrocarbons preferably having 2 to 6 carbon atoms and at least one double bond such as, for example, vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3- dimethyl-2-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl. Preference is furthermore given to alkenyl groups having 2 to 4 carbon atoms such as, inter alia, 2-propenyl, 2-butenyl or 1-methyl-2-propenyl. The alkenyl groups according to the invention may be substituted by one or more identical or different radicals.

According to the invention, "alkynyl"—on its own or as part of a chemical group—represents straight-chain or branched hydrocarbons preferably having 2 to 6 carbon atoms and at least one triple bond such as, for example, 2-propynyl, 2-butyryl, 3-butyryl, 1-methyl-2-propynyl, 2-pentynyl, 3-pentynyl, 4-pentynyl, 1-methyl-3-butyryl, 2-methyl-3-butyryl, 1-methyl-2-butyryl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-3-butynyl, 1,2-dimethyl-3-butynyl, 2,2-dimethyl-3-butynyl, 1-ethyl-3-butynyl, 2-ethyl-3-butynyl, 1-ethyl-1-methyl-2-propynyl and 2,5-hexadiynyl. Preference is furthermore given to alkynyl groups having 2 to 4 carbon atoms such as, inter alia, ethynyl, 2-propynyl or 2-butynyl-2-propenyl. The alkynyl groups according to the invention may be substituted by one or more identical or different radicals.

According to the invention, "cycloalkyl"—on its own or as part of a chemical group—represents mono-, bi- or tricyclic hydrocarbons preferably having 3 to 10 carbons such as, for example, cyclopropyl, cyclobutyl, cyclopentyl, cyclohexyl, cycloheptyl, cyclooctyl, bicyclo[2.2.1]heptyl, bicyclo[2.2.2]octyl or adamantyl. Preference is furthermore given to cycloalkyl groups having 3, 4, 5, 6 or 7 carbon atoms such as, inter alia, cyclopropyl or cyclobutyl. The cycloalkyl groups according to the invention may be substituted by one or more identical or different radicals.

According to the invention, "alkylcycloalkyl" represents mono-, bi- or tricyclic alkylcycloalkyl preferably having 4 to 10 or 4 to 7 carbon atoms such as, for example, ethylcyclopropyl, isopropylcyclobutyl, 3-methylcyclopentyl and 4-methylcyclohexyl. Preference is furthermore given to alkylcycloalkyl groups having 4, 5 or 7 carbon atoms such as, inter alia, ethylcyclopropyl or 4-methylcyclohexyl. The alkylcycloalkyl groups according to the invention may be substituted by one or more identical or different radicals.

According to the invention, "cycloalkylalkyl" represents mono-, bi- or tricyclic cycloalkylalkyl preferably having 4 to 10 or 4 to 7 carbon atoms such as, for example, cyclopropylmethyl, cyclobutylmethyl, cyclopentylmethyl, cyclohexylmethyl and cyclopentylethyl. Preference is furthermore given to cycloalkylalkyl groups having 4, 5 or 7 carbon atoms such as, inter alia, cyclopropylmethyl or cyclobutylmethyl. The cycloalkylalkyl groups according to the invention may be substituted by one or more identical or different radicals.

According to the invention, "halogen" represents fluorine, chlorine, bromine or iodine, in particular fluorine, chlorine or bromine.

The halogen-substituted chemical groups according to the invention such as, for example, haloalkyl, halocycloalkyl, haloalkoxy, haloalkylsulphanyl, haloalkylsulphinyl or haloalkylsulphonyl are mono- or polysubstituted by halogen up to the maximum possible number of substituents. In the case of polysubstitution by halogen, the halogen atoms can be identical or different, and can all be attached to one or to a plurality of carbon atoms. Here, halogen represents in particular fluorine, chlorine, bromine or iodine, preferably fluorine, chlorine or bromine and particularly preferably fluorine.

According to the invention, "halocycloalkyl" represents mono-, bi- or tricyclic halocycloalkyl having preferably 3 to 10 carbon atoms such as, inter alia, 1-fluorocyclopropyl, 2-fluorocyclopropyl or 1-fluorocyclobutyl. Preference is furthermore given to halocycloalkyl having 3, 5 or 7 carbon atoms. The halocycloalkyl groups according to the invention may be substituted by one or more identical or different radicals.

According to the invention, "haloalkyl", "haloalkenyl" or "haloalkynyl" represents halogen-substituted alkyl, alkenyl or alkynyl groups having preferably 1 to 9 identical or different halogen atoms such as, for example, monohaloalkyl such as $CH_2CH_2Cl$, $CH_2CH_2F$, $CHClCH_3$, $CHFCH_3$, $CH_2Cl$, $CH_2F$; perhaloalkyl such as $CCl_3$ or $CF_3$ or $CF_2CF_3$; polyhaloalkyl such as $CHF_2$, $CH_2F$, $CH_2CHFCl$, $CHCl_2$, $CF_2CF_2H$, $CH_2CF_3$. This applies correspondingly to haloalkenyl and other halogen-substituted radicals. Haloalkoxy is, for example, $OCF_3$, $OCHF_2$, $OCH_2F$, $OCF_2CF_3$, $OCH_2CF_3$ and $OCH_2CH_2Cl$.

Further examples for haloalkyl groups are trichloromethyl, chlorodifluoromethyl, dichlorofluoromethyl, chloromethyl, bromomethyl, 1-fluoroethyl, 2fluoroethyl, 2,2-difluoroethyl, 2,2,2-trifluoroethyl, 2,2,2-trichloroethyl, 2-chloro-2,2-difluoroethyl, pentafluoroethyl and pentafluoro-t-butyl. Preference is given to haloalkyl groups having 1 to 4 carbon atoms and 1 to 9, preferably 1 to 5, identical or different halogen atoms selected from fluorine, chlorine and bromine. Particular preference is given to haloalkyl groups having 1 or 2 carbon atoms and 1 to 5 identical or different halogen atoms selected from fluorine and chlorine such as, inter alia, difluoromethyl, trifluoromethyl or 2,2-difluoroethyl.

According to the invention, "hydroxyalkyl" represents a straight-chain or branched alcohol preferably having 1 to 6 carbon atoms such as, for example, methanol, ethanol, n-propanol, isopropanol, n-butanol, isobutanol, s-butanol and t-butanol. Preference is furthermore given to hydroxyalkyl groups having 1 to 4 carbon atoms. The hydroxyalkyl groups according to the invention may be substituted by one or more identical or different radicals.

According to the invention, "alkoxy" represents a straight-chain or branched O-alkyl preferably having 1 to 6 carbon atoms such as, for example, methoxy, ethoxy, n-propoxy, isopropoxy, n-butoxy, isobutoxy, s-butoxy and t-butoxy. Preference is furthermore given to alkoxy groups having 1 to 4 carbon atoms. The alkoxy groups according to the invention may be substituted by one or more identical or different radicals.

According to the invention, "haloalkoxy" represents halogen-substituted straight-chain or branched O-alkyl preferably having 1 to 6 carbon atoms such as, inter alia, difluoromethoxy, trifluoromethoxy, 2,2-difluoroethoxy, 1,1,2,2-tetrafluoroethoxy, 2,2,2-trifluoroethoxy and 2-chloro-1,1,2-trifluoroethoxy. Preference is furthermore given to haloalkoxy groups having 1 to 4 carbon atoms. The haloalkoxy groups according to the invention may be substituted by one or more identical or different radicals.

According to the invention, "alkylsulphanyl" represents straight-chain or branched S-alkyl preferably having 1 to 6 carbon atoms such as, for example, methylthio, ethylthio, n-propylthio, isopropylthio, n-butylthio, isobutylthio, s-butylthio and t-butylthio. Preference is furthermore given to alkylsulphanyl groups having 1 to 4 carbon atoms. The alkylsulphanyl groups according to the invention may be substituted by one or more identical or different radicals.

Examples of haloalkylsulphanylalkyl groups, i.e. halogen-substituted alkylsulphanyl groups, are inter alia difluoromethylthio, trifluoromethylthio, trichloromethylthio, chlorodifluoromethylthio, 1-fluoroethylthio, 2-fluoroethylthio, 2,2-difluoroethylthio, 1,1,2,2-tetrafluoroethylthio, 2,2,2-trifluoroethylthio or 2-chloro-1,1,2-trifluoroethylthio.

According to the invention, "alkylsulphinyl" represents straight-chain or branched alkylsulphinyl preferably having 1 to 6 carbon atoms such as, for example, methylsulphinyl, ethylsulphinyl, n-propylsulphinyl, isopropylsulphinyl, n-butylsulphinyl, isobutylsulphinyl, s-butylsulphinyl and t-butylsulphinyl. Preference is furthermore given to alkylsulphinyl groups having 1 to 4 carbon atoms. The alkylsulphinyl groups according to the invention may be substituted by one or more identical or different radicals.

Examples of haloalkylsulphinyl groups, i.e. halogen-substituted alkylsulphinyl groups, are inter alia difluoromethylsulphinyl, trifluoromethylsulphinyl, trichloromethylsulphinyl, chlorodifluoromethylsulphinyl, 1-fluoroethylsulphinyl, 2-fluoroethylsulphinyl, 2,2-difluoroethylsulphinyl, 1,1,2,2-tetrafluoroethylsulphinyl, 2,2,2-trifluoroethylsulphinyl and 2-chloro-1,1,2-trifluoroethylsulphinyl.

According to the invention, "alkylsulphonyl" represents straight-chain or branched alkylsulphonyl preferably having 1 to 6 carbon atoms such as, for example, methylsulphonyl, ethylsulphonyl, n-propylsulphonyl, isopropylsulphonyl, n-butylsulphonyl, isobutylsulphonyl, s-butylsulphonyl and t-butylsulphonyl. Preference is furthermore given to alkylsulphonyl groups having 1 to 4 carbon atoms. The alkylsulphonyl groups according to the invention may be substituted by one or more identical or different radicals.

Examples of haloalkylsulphonyl groups, i.e. halogen-substituted alkylsulphonyl groups, are inter alia difluoromethylsulphonyl, trifluoromethylsulphonyl, trichloromethylsulphonyl, chlorodifluoromethylsulphonyl, 1-fluoroethylsulphonyl, 2-fluoroethylsulphonyl, 2,2-difluoroethylsulphonyl, 1,1,2,2-tetrafluoroethylsulphonyl, 2,2,2-trifluoroethylsulphonyl and 2-chloro-1,1,2-trifluoroethylsulphonyl.

According to the invention, "alkylcarbonyl" represents straight-chain or branched alkyl-C(=O) preferably having 2 to 7 carbon atoms such as methylcarbonyl, ethylcarbonyl, n-propylcarbonyl, isopropylcarbonyl, s-butylcarbonyl and t-butylcarbonyl. Preference is furthermore given to alkylcarbonyl groups having 1 to 4 carbon atoms. The alkylcarbonyl groups according to the invention may be substituted by one or more identical or different radicals.

According to the invention, "cycloalkylcarbonyl" represents straight-chain or branched cycloalkylcarbonyl preferably having 3 to 10 carbon atoms in the cycloalkyl moiety such as, for example, cyclopropylcarbonyl, cyclobutylcarbonyl, cyclopentylcarbonyl, cyclohexylcarbonyl, cycloheptylcarbonyl, cyclooctylcarbonyl, bicyclo[2.2.1]heptyl, bicyclo[2.2.2]octylcarbonyl and adamantylcarbonyl. Preference is furthermore given to cycloalkylcarbonyl having 3, 5 or 7 carbon atoms in the cycloalkyl moiety. The cycloalkylcarbonyl groups according to the invention may be substituted by one or more identical or different radicals.

According to the invention, "alkoxycarbonyl"—alone or as a constituent of a chemical group—represents straight-chain or branched alkoxycarbonyl, preferably having 1 to 6 carbon atoms or having 1 to 4 carbon atoms in the alkoxy moiety such as, for example, methoxycarbonyl, ethoxycarbonyl, n-propoxycarbonyl, isopropoxycarbonyl, s-butoxycarbonyl and t-butoxycarbonyl. The alkoxycarbonyl groups according to the invention may be substituted by one or more identical or different radicals.

According to the invention, "alkylaminocarbonyl" represents straight-chain or branched alkylaminocarbonyl having preferably 1 to 6 carbon atoms or 1 to 4 carbon atoms in the alkyl moiety, such as, for example, methylaminocarbonyl, ethylaminocarbonyl, n-propylaminocarbonyl, isopropylaminocarbonyl, s-butylaminocarbonyl and t-butylaminocarbonyl. The alkylaminocarbonyl groups according to the invention may be substituted by one or more identical or different radicals.

According to the invention, "N,N-dialkylaminocarbonyl" represents straight-chain or branched N,N-dialkylaminocarbonyl having preferably 1 to 6 carbon atoms or 1 to 4 carbon atoms in the alkyl moiety, such as, for example, N,N-dimethylaminocarbonyl, N,N-diethylaminocarbonyl, N,N-di(n-propylamino)carbonyl, N,N-di(isopropylamino)carbonyl and N,N-di-(s-butylamino)carbonyl. The N,N-dialkylaminocarbonyl groups according to the invention may be substituted by one or more identical or different radicals.

According to the invention, "aryl" represents a mono-, bi- or polycyclic aromatic system having preferably 6 to 14, in particular 6 to 10 ring carbon atoms such as, for example, phenyl, naphthyl, anthryl, phenanthrenyl, preferably phenyl. Furthermore, aryl also represents polycyclic systems such as tetrahydronaphthyl, indenyl, indanyl, fluorenyl, biphenyl, where the bonding site is on the aromatic system. The aryl groups according to the invention may be substituted by one or more identical or different radicals.

Examples for substituted aryl groups are the arylalkyl groups which may likewise be substituted by one or more identical or different radicals in the alkyl and/or aryl moiety. Examples for such arylalkyl groups are inter alia benzyl and 1-phenylethyl.

According to the invention, "heterocycle", "heterocyclic ring" or "heterocyclic ring system" represents a carbocyclic ring system having at least one ring in which at least one carbon atom is replaced by a heteroatom, preferably by a heteroatom from the group consisting of N, O, S, P, B, Si, Se, and which is saturated, unsaturated or heteroaromatic and may be unsubstituted or substituted by a substituent Z, where the point of attachment is located at a ring atom. Unless defined differently, the heterocyclic ring contains preferably 3 to 9 ring atoms, especially 3 to 6 ring atoms, and one or more, preferably 1 to 4, in particular 1, 2 or 3, heteroatoms in the heterocyclic ring, preferably from the group consisting of N, O, and S, although no two oxygen atoms should be directly adjacent. The heterocyclic rings usually contain not more than 4 nitrogen atoms and/or not more than 2 oxygen atoms and/or not more than 2 sulphur atoms. If the heterocyclyl radical or the heterocyclic ring is optionally substituted, it can be fused to other carbocyclic or heterocyclic rings. In the case of optionally substituted heterocyclyl, the invention also embraces polycyclic systems such as, for example, 8-azabicyclo[3.2.1]octanyl or 1-azabicyclo[2.2.1]heptyl. In the case of optionally substituted heterocyclyl, the invention also embraces spirocyclic systems such as, for example, 1-oxa-5-azaspiro[2.3]hexyl.

Heterocyclyl groups according to the invention are, for example, piperidinyl, piperazinyl, morpholinyl, thiomorpholinyl, dihydropyranyl, tetrahydropyranyl, dioxanyl, pyrrolinyl, pyrrolidinyl, imidazolinyl, imidazolidinyl, thiazolidinyl, oxazolidinyl, dioxolanyl, dioxolyl, pyrazolidinyl, tetrahydrofuranyl, dihydrofuranyl, oxetanyl, oxiranyl, azetidinyl, aziridinyl, oxazetidinyl, oxaziridinyl, oxazepanyl, oxazinanyl, azepanyl, oxopyrrolidinyl, dioxopyrrolidinyl, oxomorpholinyl, oxopiperazinyl and oxepanyl.

Heteroarylene, i.e. heteroaromatic systems, has a particular meaning. According to the invention, the term heteroaryl represents heteroaromatic compounds, i.e. completely unsaturated aromatic heterocyclic compounds which fall under the above definition of heterocycles. Preference is given to 5- to 7-membered rings having 1 to 3, preferably 1 or 2, identical or different heteroatoms from the group above. Heteroaryl groups according to the invention are, for example, furyl, thienyl, pyrazolyl, imidazolyl, 1,2,3- and 1,2,4-triazolyl, isoxazolyl, thiazolyl, isothiazolyl, 1,2,3-, 1,3,4-, 1,2,4- and 1,2,5-oxadiazolyl, azepinyl, pyrrolyl, pyridyl, pyridazinyl, pyrimidinyl, pyrazinyl, 1,3,5-, 1,2,4- and 1,2,3-triazinyl, 1,2,4-, 1,3,2-, 1,3,6- and 1,2,6-oxazinyl, oxepinyl, thiepinyl, 1,2,4-triazolonyl and 1,2,4-diazepinyl. The heteroaryl groups according to the invention may also be substituted by one or more identical or different radicals.

Substituted groups such as a substituted alkyl, alkenyl, alkynyl, cycloalkyl, aryl, phenyl, benzyl, heterocyclyl and heteroaryl radical are, for example, a substituted radical derived from the unsubstituted base structure, where the substituents are, for example, one or more, preferably 1, 2 or 3, radicals from the group of halogen, alkoxy, alkylsulphanyl, hydroxyl, amino, nitro, carboxyl or a group equivalent to the carboxyl group, cyano, isocyano, azido, alkoxycarbonyl, alkylcarbonyl, formyl, carbamoyl, mono- and N,N-dialkylaminocarbonyl, substituted amino such as acylamino, mono- and N,N-dialkylamino, trialkylsilyl and optionally substituted cycloalkyl, optionally substituted aryl, optionally substituted heterocyclyl, where each of the latter cyclic groups may also be bonded via heteroatoms or divalent functional groups such as in the alkyl radicals mentioned, and alkylsulphinyl, including both enantiomers of the alkylsulphonyl group, alkylsulphonyl, alkylphosphinyl, alkylphosphonyl and, in the case of cyclic radicals (="cyclic skeleton"), also alkyl, haloalkyl, alkylsulphanylalkyl, alkoxyalkyl, optionally substituted mono- and N,N-dialkylaminoalkyl and hydroxyalkyl.

The term "substituted groups", such as substituted alkyl etc., includes, as substituents, in addition to the saturated hydrocarbonaceous radicals mentioned, corresponding unsaturated aliphatic and aromatic radicals such as optionally substituted alkenyl, alkynyl, alkenyloxy, alkynyloxy, alkenylthio, alkynylthio, alkenyloxycarbonyl, alkynyloxycarbonyl, alkenylcarbonyl, alkynylcarbonyl, mono- and N,N-dialkenylaminocarbonyl, mono- and dialkynylaminocarbonyl, mono- and N,N-dialkenylamino, mono- and N,N-dialkynylamino, trialkenylsilyl, trialkynylsilyl, optionally substituted cycloalkenyl, optionally substituted cycloalkynyl, phenyl, phenoxy etc. In the case of substituted cyclic radicals with aliphatic components in the ring, cyclic systems with those substituents bonded to the ring by a double bond are also included, for example those having an alkylidene group such as methylidene or ethylidene, or an oxo group, imino group or substituted imino group.

When two or more radicals form one or more rings, these may be carbocyclic, heterocyclic, saturated, partly saturated, unsaturated, for example also aromatic and further substituted.

The substituents mentioned by way of example ("first substituent level") may, if they contain hydrocarbon-containing moieties, optionally be further substituted therein ("second substituent level"), for example by one of the substituents as defined for the first substituent level. Corresponding further substituent levels are possible. The term "substituted radical" preferably embraces just one or two substituent levels.

Preferred substituents for the substituent levels are, for example, amino, hydroxy, halogen, nitro, cyano, isocyano, mercapto, isothiocyanato, carboxyl, carboxamide, $SF_5$, aminosulphonyl, alkyl, cycloalkyl, alkenyl, cycloalkenyl, alkynyl, N-monoalkylamino, N,N-dialkylamino, N-alkanoylamino, alkoxy, alkenyloxy, alkynyloxy, cycloalkoxy, cycloalkenyloxy, alkoxycarbonyl, alkenyloxycarbonyl, alkynyloxycarbonyl, aryloxycarbonyl, alkanoyl, alkenylcarbonyl, alkynylcarbonyl, arylcarbonyl, alkylsulphanyl, cycloalkylsulphanyl, alkenylthio, cycloalkenylthio, alkynylthio, alkylsulphenyl and alkylsulphinyl, where both enantiomers of the alkylsulphinyl group are included, alkylsulphonyl, N-monoalkylaminosulphonyl, N,N-dialkylaminosulphonyl, alkylphosphinyl, alkylphosphonyl, where in the case of alkylphosphinyl and alkylphosphonyl both enantiomers are included, N-alkylaminocarbonyl, N,N-dialkylaminocarbonyl, N-alkanoylaminocarbonyl, N-alkanoyl-N-alkylaminocarbonyl, aryl, aryloxy, benzyl, benzyloxy, benzylthio, arylthio, arylamino, benzylamino, heterocyclyl and trialkylsilyl.

Substituents composed of a plurality of substituent levels are preferably alkoxyalkyl, alkylsulphanylalkyl, alkylsulphanylalkoxy, alkoxyalkoxy, phenethyl, benzyloxy, haloalkyl, halocycloalkyl, haloalkoxy, haloalkylsulphanyl, haloalkylsulphinyl, haloalkylsulphonyl, haloalkanoyl, haloalkylcarbonyl, haloalkoxycarbonyl, haloalkoxyalkoxy, haloalkoxyalkylsulphanyl, haloalkoxyalkanoyl, haloalkoxyalkyl.

In the case of radicals having carbon atoms, preference is given to those having 1 to 6 carbon atoms, preferably 1 to 4 carbon atoms, especially 1 or 2 carbon atoms. Preference is generally given to substituents from the group of halogen, e.g. fluorine and chlorine, $(C_1-C_4)$-alkyl, preferably methyl or ethyl, $(C_1-C_4)$-haloalkyl, preferably trifluoromethyl, $(C_1-C_4)$-alkoxy, preferably methoxy or ethoxy, $(C_1-C_4)$-haloalkoxy, nitro and cyano. Particular preference is given here to the substituents methyl, methoxy, fluorine and chlorine.

Substituted amino such as mono- or disubstituted amino means a radical from the group of the substituted amino radicals which are N-substituted, for example, by one or two identical or different radicals from the group consisting of alkyl, hydroxy, amino, alkoxy, acyl and aryl; preferably N-mono- and N,N-dialkylamino, (for example methylamino, ethylamino, N,N-dimethylamino, N,N-diethylamino, N,N-di-n-propylamino, N,N-diisopropylamino or N,N-dibutylamino), N-mono- or N,N-dialkoxyalkylamino groups (for example N-methoxymethylamino, N-methoxyethylamino, N,N-di(methoxymethyl)amino or N,N-di(methoxyethyl)amino), N-mono- and N,N-diarylamino, such as optionally substituted anilines, acylamino, N,N-diacylamino, N-alkyl-N-arylamino, N-alkyl-N-acylamino and also saturated N-heterocycles; preference is given here to alkyl radicals having 1 to 4 carbon atoms; here, aryl is preferably phenyl or substituted phenyl; for acyl, the definition given further below applies, preferably $(C_1-C_4)$-alkanoyl. The same applies to substituted hydroxylamino or hydrazino.

According to the invention, the term "cyclic amino groups" embraces heteroaromatic or aliphatic ring systems having one or more nitrogen atoms. The heterocycles are saturated or unsaturated, consist of one or more optionally fused ring systems and optionally contain further heteroatoms such as, for example, one or two nitrogen, oxygen and/or sulphur atoms. Furthermore, the term also includes groups having a spiro ring or a bridged ring system. The number of atoms which form the cyclic amino group is not limited and, in the case of a one-ring system, for example, the groups can consist of 3 to 8 ring atoms, and in the case of a two-ring system of 7 to 11 atoms.

Examples of cyclic amino groups having saturated and unsaturated monocyclic groups having a nitrogen atom as heteroatom which may be mentioned are 1-azetidinyl, pyrrolidino, 2-pyrrolidin-1-yl, 1-pyrrolyl, piperidino, 1,4-dihydropyrazin-1-yl, 1,2,5,6-tetrahydropyrazin-1-yl, 1,4-dihydropyridin-1-yl, 1,2,5,6-tetrahydropyridin-1-yl, homopiperidinyl; examples of cyclic amino groups having saturated and unsaturated monocyclic groups having two or more nitrogen atoms as heteroatoms which may be mentioned are 1-imidazolidinyl, 1-imidazolyl, 1-pyrazolyl, 1-triazolyl, 1-tetrazolyl, 1-piperazinyl, 1-homopiperazinyl, 1,2-dihydropiperazin-1-yl, 1,2-dihydropyrimidin-1-yl, perhydropyrimidin-1-yl, 1,4-diazacycloheptan-1-yl; examples of cyclic amino groups having saturated and unsaturated monocyclic groups having one or two oxygen atoms and one to three nitrogen atoms as heteroatoms, such as, for example, oxazolidin-3-yl, 2,3-dihydroisoxazol-2-yl, isoxazol-2-yl, 1,2,3-oxadiazin-2-yl, morpholino, examples of cyclic amino groups having saturated and unsaturated monocyclic groups having one to three nitrogen atoms and one to two sulphur atoms as heteroatoms which may be mentioned are thiazolidin-3-yl, isothiazolin-2-yl, thiomorpholino, or dioxothiomorpholino; examples of cyclic amino groups having saturated and unsaturated fused cyclic groups which may be mentioned are indol-1-yl, 1,2-dihydrobenzimidazol-1-yl, perhydropyrrolo[1,2-a]pyrazin-2-yl; examples of cyclic amino groups having spirocyclic groups which may be mentioned are 2-azaspiro[4,5]decan-2-yl; examples of cyclic amino groups having bridged heterocyclic groups which may be mentioned are 2-azabicyclo[2.2.1]heptan-7-yl.

Substituted amino also includes quaternary ammonium compounds (salts) with four organic substituents on the nitrogen atom.

Optionally substituted phenyl is preferably phenyl which is unsubstituted or mono- or polysubstituted, preferably up to trisubstituted, by identical or different radicals from the group of halogen, $(C_1-C_4)$-alkyl, $(C_1-C_4)$-alkoxy, $(C_1-C_4)$-alkoxy-$(C_1-C_4)$-alkoxy, $(C_1-C_4)$-alkoxy-$(C_1-C_4)$-alkyl, $(C_1-C_4)$-haloalkyl, $(C_1-C_4)$-haloalkoxy, $(C_1-C_4)$-alkylsulphanyl, $(C_1-C_4)$-haloalkylsulphanyl, cyano, isocyano and nitro, for example o-, m- and p-tolyl, dimethylphenyls, 2-, 3- and 4-chlorophenyl, 2-, 3- and 4-fluorophenyl, 2-, 3- and 4-trifluoromethyl- and -trichloromethylphenyl, 2,4-, 3,5-, 2,5- and 2,3-dichlorophenyl, o-, m- and p-methoxyphenyl.

Optionally substituted cycloalkyl is preferably cycloalkyl, which is unsubstituted or mono- or polysubstituted, preferably up to trisubstituted, by identical or different radicals from the group of halogen, cyano, $(C_1-C_4)$-alkyl, $(C_1-C_4)$-alkoxy, $(C_1-C_4)$-alkoxy-$(C_1-C_4)$-alkoxy, $(C_1-C_4)$-alkoxy-$(C_1-C_4)$-alkyl, $(C_1-C_4)$-haloalkyl and $(C_1-C_4)$-haloalkoxy, especially by one or two $(C_1-C_4)$-alkyl radicals.

Optionally substituted heterocyclyl is preferably heterocyclyl which is unsubstituted or mono- or polysubstituted, preferably up to trisubstituted, by identical or different radicals from the group of halogen, cyano, $(C_1-C_4)$-alkyl, $(C_1-C_4)$-alkoxy, $(C_1-C_4)$-alkoxy-$(C_1-C_4)$-alkoxy, $(C_1-C_4)$-alkoxy-$(C_1-C_4)$-alkyl, $(C_1-C_4)$-haloalkyl, $(C_1-C_4)$-haloalkoxy, nitro and oxo, especially mono- or polysubstituted by radicals from the group of halogen, $(C_1-C_4)$-alkyl, $(C_1-C_4)$-alkoxy, $(C_1-C_4)$-haloalkyl and oxo, most preferably substituted by one or two $(C_1-C_4)$-alkyl radicals.

Examples of alkyl-substituted heteroaryl groups are furylmethyl, thienylmethyl, pyrazolylmethyl, imidazolylmethyl, 1,2,3- and 1,2,4-triazolylmethyl, isoxazolylmethyl, thiazolylmethyl, isothiazolylmethyl, 1,2,3-, 1,3,4-, 1,2,4- and 1,2,5-oxadiazolylmethyl, azepinylmethyl, pyrrolylmethyl, pyridylmethyl, pyridazinylmethyl, pyrimidinylmethyl, pyrazinylmethyl, 1,3,5-, 1,2,4- and 1,2,3-triazinylmethyl, 1,2,4-, 1,3,2-, 1,3,6- and 1,2,6-oxazinylmethyl, oxepinylmethyl, thiepinylmethyl and 1,2,4-diazepinylmethyl.

Salts which are suitable according to the invention of the compounds according to the invention, for example salts with bases or acid addition salts, are all customary non-toxic salts, preferably agriculturally and/or physiologically acceptable salts. For example salts with bases or acid addition salts. Preference is given to salts with inorganic bases such as, for example, alkali metal salts (e.g. sodium, potassium or caesium salts), alkaline earth metal salts (e.g. calcium or magnesium salts), ammonium salts or salts with organic bases, in particular with organic amines, such as, for example, triethylammonium, dicyclohexylammonium, N,N'-dibenzylethylenediammonium, pyridinium, picolinium or ethanolammonium salts, salts with inorganic acids (e.g. hydrochlorides, hydrobromides, dihydrosulphates, trihydrosulphates or phosphates), salts with organic carboxylic acids or organic sulphoacids (e.g. formates, acetates, trifluoroacetates, maleates, tartrates, methanesulphonates, benzenesulphonates or 4-toluenesulphonates). It is known that t-amines such as some of the compounds according to the invention are capable of forming N-oxides, which also represent salts according to the invention.

The compounds according to the invention may, depending on the nature of the substituents, be in the form of geometric and/or optically active isomers or corresponding isomer mixtures in different compositions. These stereoisomers are, for example, enantiomers, diastereomers, atropisomers or geometric isomers. Accordingly, the invention encompasses both pure stereoisomers and any mixtures of these isomers.

If appropriate, the compounds according to the invention may be present in various polymorphic forms or as a mixture of different polymorphic forms. Both the pure polymorphs and the polymorph mixtures are provided by the invention and can be used in accordance with the invention.

The compounds of the general formula (I) can be mixed or applied jointly with other insecticidal, nematicidal, acaricidal or antimicrobial active compounds. In these mixtures or joint applications, synergistic effects occur, i.e. the observed effect of these mixture or joint applications is higher than the total of the effects of the individual active compounds in these applications. Examples of such mixing or combination partners are:

(1) Acetylcholinesterase (AChE) inhibitors such as, for example, carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos-ethyl, azinphos-methyl, cadusafos, chlorethoxyfos, chlorfenvinphos, chlormephos, chloropyrifos, chloropyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl)salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion.

(2) GABA-gated chloride channel antagonists such as, for example, cyclodiene organochlorines, e.g. chlordane and endosulfan; or phenylpyrazoles (fiproles), e.g. ethiprole and fipronil.

(3) Sodium channel modulators/voltage-dependent sodium channel blockers such as, for example, pyrethroids, e.g. acrinathrin, allethrin, d-cis-trans allethrin, d-trans allethrin, bifenthrin, bioallethrin, bioallethrin s-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans-isomers], deltamethrin, empenthrin [(EZ)-(1R)-isomers], esfenvalerate, etofenprox, fenpropathrin, fenvalerate, flucythrinate, flumethrin, tau-fluvalinate, halfenprox, imiprothrin, kadethrin, permethrin, phenothrin [(1R)-trans-isomer], prallethrin, pyrethrins (pyrethrum), resmethrin, silafluofen, tefluthrin, tetramethrin, tetramethrin [(1R)-isomers)], tralomethrin and transfluthrin; or DDT; or methoxychlor.

(4) Nicotinergic acetylcholine receptor (nAChR) agonists such as, for example, neonicotinoids, e.g. acetamiprid, clothianidin, dinotefuran, imidacloprid, nitenpyram, thiacloprid and thiamethoxam; or nicotine; or sulfoxaflor.

(5) Nicotinergic acetylcholine receptor (nAChR) allosteric activators such as, for example, spinosyns, e.g. spinetoram and spinosad.

(6) Chloride channel activators such as, for example, avermectins/milbemycins, for example abamectin, emamectin benzoate, lepimectin and milbemectin.

(7) Juvenile hormone imitators such as, for example, juvenile hormone analogues, e.g. hydroprene, kinoprene and methoprene; or fenoxycarb; or pyriproxyfen.

(8) Active compounds with unknown or nonspecific mechanisms of action such as, for example, alkyl halides, e.g. methyl bromide and other alkyl halides; or chloropicrin; or sulphuryl fluoride; or borax; or tartar emetic.

(9) Selective antifeedants, for example pymetrozine or flonicamid.

(10) Mite growth inhibitors, for example clofentezine, hexythiazox and diflovidazin; or etoxazole.

(11) Microbial disruptors of the insect gut membrane, e.g. *Bacillus thuringiensis* subspecies *israelensis*, *Bacillus thuringiensis* subspecies *aizawai*, *Bacillus thuringiensis* subspecies *kurstaki*, *Bacillus thuringiensis* subspecies *tenebrionis* and B.t. plant proteins: Cry1Ab, Cry1Ac, Cry1Fa, Cry1A.105, Cry2Ab, Vip3A, mCry3A, Cry3Ab, Cry3Bb, Cry34 Ab1/35Ab1; or

*Bacillus sphaericus*.

(12) Oxidative phosphorylation inhibitors, ATP disruptors, for example diafenthiuron; or organotin compounds, e.g. azocyclotin, cyhexatin and fenbutatin oxide; or propargite; or tetradifon.

(13) Oxidative phosphorylation decouplers acting by interrupting the H proton gradient such as, for example, chlorfenapyr, DNOC and sulfluramid.

(14) Nicotinergic acetylcholine receptor antagonists such as, for example, bensultap, cartap hydrochloride, thiocyclam, and thiosultap-sodium.

(15) Chitin biosynthesis inhibitors, type 0, such as, for example, bistrifluron, chlorfluazuron, diflubenzuron, flucycloxuron, flufenoxuron, hexaflumuron, lufenuron, novaluron, noviflumuron, teflubenzuron and triflumuron.

(16) chitin biosynthesis inhibitors, type 1, such as, for example, buprofezin.

(17) Molting disruptors, dipteran such as, for example, cyromazine.

(18) Ecdysone receptor agonists such as, for example, chromafenozide, halofenozide, methoxyfenozide and tebufenozide.

(19) Octopaminergic agonists such as, for example, amitraz.

(20) Complex-III electron transport inhibitors such as, for example, hydramethylnone or acequinocyl or fluacrypyrim.

(21) Complex-I electron transport inhibitors, for example

METI acaricides, e.g. fenazaquin, fenpyroximate, pyrimidifen, pyridaben, tebufenpyrad and tolfenpyrad; or rotenone (Derris).

(22) Voltage-gated sodium channel blockers, for example indoxacarb or metaflumizone.

(23) Inhibitors of acetyl-CoA carboxylase such as, for example, tetronic and tetramic acid derivatives, e.g. spirodiclofen, spiromesifen and spirotetramat.

(24) Complex-IV electron transport inhibitors such as, for example, phosphines, e.g. aluminium phosphide, calcium phosphide, phosphine and zinc phosphide; or cyanide.

(25) Complex-II electron transport inhibitors, such as, for example, cyenopyrafen and cyflumetofen.

(28) Ryanodine receptor effectors such as, for example, diamides, e.g. chlorantraniliprole, cyantraniliprole and flubendiamide.

Further active compounds having an unknown mechanism of action, such as, for example, amidoflumet, azadirachtin, benclothiaz, benzoximate, bifenazate, bromopropylate, chinomethionat, cryolite, dicofol, diflovidazin, fluensulphone, flufenerim, flufiprole, fluopyram, fufenozide, imidaclothiz, iprodione, meperfluthrin, pyridalyl, pyrifluquinazon, tetramethylfluthrin and iodomethane; and additionally preparations based on *Bacillus firmus* (particularly strain CNCM I-1582, for example VOTiVO™, BioNem), and the following known active compounds:

3-bromo-N-{2-bromo-4-chlor-6-[(1-cyclopropylethyl) carbamoyl]phenyl}-1-(3-chloropyridin-2-yl)-1H-pyrazole-5-carboxamide (known from WO 2005/077934), 4-{[(6-bromopyrid-3-yl)methyl](2-fluoroethyl)amino}furan-2 (5H)-one (known from WO 2007/115644), 4-{[(6-fluoropyrid-3-yl)methyl](2,2-difluoroethyl)amino}furan-2 (5H)-one (known from WO 2007/115644), 4-{[(2-chloro-1, 3-thiazol-5-yl)methyl](2-fluoroethyl)amino}furan-2(5H)-one (known from WO 2007/115644), 4-{[(6-chloropyrid-3-yl)methyl](2-fluoroethyl)amino}furan-2(5H)-one (known from WO 2007/115644), flupyradifurone, 4-{[(6-chloro-5-fluoropyrid-3-yl)methyl](methyl)amino}furan-2(5H)-one (known from WO 2007/115643), 4-{[(5,6-dichloropyrid-3- yl)methyl](2-fluoroethyl)amino}furan-2(5H)-one (known from WO 2007/115646), 4-{[(6-chloro-5-fluoropyrid-3-yl)methyl](cyclopropyl)amino}furan-2(5H)-one (known from WO 2007/115643), 4-{[(6-chloropyrid-3-yl)methyl](cyclopropyl)amino}furan-2(5H)-one (known from EP A 0 539 588), 4-{[(6-chloropyrid-3-yl)methyl](methyl)amino}furan-2(5H)-one (known from EP A 0 539 588), {[1-(6-chloropyridin-3-yl)ethyl](methyl)oxido-$\lambda^4$-sulphanylidene}cyanamide (known from WO2007/149134) and its diastereomers {[(1R)-1-(6-chloropyridin-3-yl)ethyl](methyl)oxido-$\lambda^4$-sulphanylidene}cyanamide (A) and {[(1S)-1-(6-chloropyridin-3-yl)ethyl](methyl)oxido-$\lambda^4$-sulphanylidene}cyanamide (B) (likewise known from WO 2007/149134) and also diastereomers [(R)-methyl(oxido){(1R)-1-[6-(trifluoromethyl)pyridin-3-yl]ethyl}-$\lambda^4$-sulphanylidene]cyanamide (A1) and [(S)-methyl(oxido){(1S)-1-[6-(trifluoromethyl)pyridin-3-yl]ethyl}-$\lambda^4$-sulphanylidene]cyanamide (A2), identified as diastereomer group A (known from WO 2010/074747, WO 2010/074751), [(R)-methyl(oxido){(1S)-1-[6-(trifluoromethyl)pyridin-3-yl]ethyl}-$\lambda^4$-sulphanylidene]cyanamide (B1) and [(S)-methyl(oxido){(1R)-1-[6-(trifluoromethyl)pyridin-3-yl]ethyl}-$\lambda^4$-sulphanylidene]cyanamide (B2), identified as diastereomer group B (likewise known from WO 2010/074747, WO 2010/074751) and 11-(4-chloro-2,6-dimethylphenyl)-12-hydroxy-1,4-dioxa-9-azadispiro[4.2.4.2]tetradec-11-en-10-one (known from WO 2006/089633), 3-(4'-fluoro-2,4-dimethylbiphenyl-3-yl)-4-hydroxy-8-oxa-1-azaspiro[4.5]dec-3-en-2-one (known from WO 2008/067911), 1-{2-fluoro-4-methyl-5-[(2,2,2-trifluoroethyl)sulphinyl]phenyl}-3-(trifluoromethyl)-1H-1,2,4-triazol-5-amine (known from WO 2006/043635), afidopyropen (known from WO 2008/066153), 2-cyano-3-(difluoromethoxy)-N,N-dimethylbenzolsulphonamide (known from WO 2006/056433), 2-cyano-3-(difluoromethoxy)-N-methylbenzolsulphonamide (known from WO 2006/100288), 2-cyano-3-(difluoromethoxy)-N-ethylbenzenesulphonamide (known from WO 2005/035486), 4-(difluoromethoxy)-N-ethyl-N-methyl-1,2-benzothiazol-3-amine-1,1-dioxide (known from WO 2007/057407), N-[1-(2,3-dimethylphenyl)-2-(3,5-dimethylphenyl)ethyl]-4,5-dihydro-1,3-thiazol-2-amine (known from WO 2008/104503), {1'-[(2E)-3-(4-chlorophenyl)prop-2-en-1-yl]-5-fluorospiro[indol-3,4'-piperidine]-1(2H)-yl}(2-chloropyridin-4-yl)methanone (known from WO 2003/106457), 3-(2,5-dimethylphenyl)-4-hydroxy-8-methoxy-1,8-diazaspiro[4.5]dec-3-en-2-one (known from WO 2009/049851), 3-(2,5-dimethylphenyl)-8-methoxy-2-oxo-1,8-diazaspiro[4.5]dec-3-en-4-yl ethyl carbonate (known from WO 2009/049851), 4-(but-2-yn-1-yloxy)-6-(3,5-dimethylpiperidin-1-yl)-5-fluoropyrimidine (known from WO 2004/099160), (2,2,3,3,4,4,5,5-octafluoropentyl)(3,3,3-trifluoropropyl)malononitrile (known from WO 2005/063094), (2,2,3,3,4,4,5,5-octafluoropentyl)(3,3,4,4,4-pentafluorobutyl)malononitrile (known from WO 2005/063094), 8-[2-(cyclopropylmethoxy)-4-(trifluoromethyl)phenoxy]-3-[6-(trifluoromethyl)pyridazin-3-yl]-3-azabicyclo[3.2.1]octane (known from WO 2007/040280), flometoquin, PF1364 (CAS Reg. No. 1204776-60-2) (known from JP 2010/018586), 5-[5-(3,5-dichlorophenyl)-5-(trifluoromethyl)-4,5-dihydro-1,2-oxazol-3-yl]-2-(1H-1,2,4-triazol-1-yl)benzonitrile (known from WO 2007/075459), 5-[5-(2-chloropyridin-4-yl)-5-(trifluoromethyl)-4,5-dihydro-1,2-oxazol-3-yl]-2-(1H-1,2,4-triazol-1-yl)benzonitrile (known from WO 2007/075459), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (known from WO 2005/085216), 4-{[(6-chloropyridin-3-yl)methyl](cyclopropyl)amino}-1,3-oxazol-2(5H)-one, 4-{[(6-chloropyridin-3-yl)methyl](2,2-difluoroethyl)amino}-1,3-oxazol-2(5H)-one, 4-{[(6-chloropyridin-3-yl)methyl](ethyl)amino}-1,3-oxazol-2(5H)-one, 4-{[(6-chloropyridin-3-yl)methyl](methyl)amino}-1,3-oxazol-2(5H)-one (all known from WO 2010/005692), pyflubumide (known from WO 2002/096882), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO 2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO 2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (known from WO 2005/085216), methyl 2-[3,5-dibromo-2-({[3-bromo-1-(3-chloropyridin-2-yl)-1H-pyrazol-5-yl]carbonyl}amino)benzoyl]-1,2-diethylhydrazinecarboxylate (known from WO 2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (known from WO 2005/085216), (5RS,7RS;5RS,7SR)-1-(6-chloro-3-pyridylmethyl)-1,2,3,5,6,7-hexahydro-7-methyl-8-nitro-5-propoxyimidazo[1,2-a]pyridine (known from WO 2007/101369), 2-{6-[2-(5-fluoropyridin-3-yl)-1,3-thiazol-5-yl]pyridin-2-yl}pyrimidine (known from WO 2010/006713), 2-{6-[2-(pyridin-3-yl)-1,3-thiazol-5-yl]pyridin-2-yl}pyrimidine (known from WO 2010/006713), 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide (known from WO 2010/069502), 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (known from WO 2010/069502), N-[2-(tert-butylcarbamoyl)-4-cyano-6-methylphenyl]-1-(3-chloropyridin-2-yl)-3-{[5-(trifluoromethyl)-1H-tetrazol-1-yl]methyl}-1H-pyrazole-5-carboxamide (known from WO 2010/069502), N-[2-(tert-butylcarbamoyl)-4-cyano-6-methylphenyl]-1-(3-chloropyridin-2-yl)-3-{[5-(trifluoromethyl)-2H-tetrazol-2-yl]methyl}-1H-pyrazole-5-carboxamide (known from WO 2010/069502), (1E)-N-[(6-chloropyridin-3-yl)methyl]-N'-cyano-N-(2,2-difluoroethyl)ethanimideamide (known from WO 2008/009360), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN 102057925), methyl 2-[3,5-dibromo-2-({[3-bromo-1-(3-chloropyridin-2-yl)-1H-pyrazol-5-yl]carbonyl}amino)benzoyl]-2-ethyl-1-methylhydrazinecarboxylate (known from WO 2011/049233), heptafluthrin, pyriminostrobin, flufenoxystrobin and 3-chloro-N$^2$-(2-cyanopropan-2-yl)-N$^1$-[4-(1,1,1,2,3,3,3-heptafluoropropan-2-yl)-2-methylphenyl]phthalamide (known from WO2012/034472).

Antimicrobially Active Compounds:

(1) Ergosterol biosynthesis inhibitors, for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulphate, imibenconazole, ipconazole, metconazole, myclobutanil, naftifin, nuarimol, oxpoconazole, paclobutrazole, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, uniconazole-p, viniconazole, voriconazole, 1-(4-chlorophenyl)-2-(1H-1,2,4-triazol-1-yl) cycloheptanol, methyl 1-(2,2-dimethyl-2,3-dihydro-1H-inden-1-yl)-1H-imidazole-5-carboxylate, N'-{5-(difluoromethyl)-2-methyl-4-[3-(trimethylsilyl)propoxy]phenyl}-N-ethyl-N-methylimidoformamide, N-ethyl-N-methyl-N'-{2-methyl-5-(trifluoromethyl)-4-[3-(trimethylsilyl)propoxy] phenyl}imidoformamide and O-[1-(4-methoxyphenoxy)-3, 3-dimethylbutan-2-yl]1H-imidazole-1-carbothioate.

(2) Respiration inhibitors (respiratory chain inhibitors), for example bixafen, boscalid, carboxin, diflumetorim, fenfuram, fluopyram, flutolanil, fluxapyroxad, furametpyr, furmecyclox, isopyrazam mixture of the syn-epimeric racemate 1RS,4SR,9RS and of the anti-epimeric racemate 1RS,4SR, 9SR, isopyrazam (anti-epimeric racemate), isopyrazam (anti-epimeric enantiomer 1R,4S,9S), isopyrazam (anti-epimeric enantiomer 1S,4R,9R), isopyrazam (syn-epimeric racemate 1RS,4SR,9RS), isopyrazam (syn-epimeric enantiomer 1R,4S,9R), isopyrazam (syn-epimeric enantiomer 1S,4R,9S), mepronil, oxycarboxin, penflufen, penthiopyrad, sedaxane, thifluzamide, 1-methyl-N-[2-(1,1, 2,2-tetrafluoroethoxy)phenyl]-3-(trifluoromethyl)-1H-pyrazole-4-carboxamide, 3-(difluoromethyl)-1-methyl-N-[2-(1, 1,2,2-tetrafluoroethoxy)phenyl]-1H-pyrazole-4-carboxamide, 3-(difluoromethyl)-N-[4-fluoro-2-(1,1,2,3,3, 3-hexafluoropropoxy)phenyl]-1-methyl-1H-pyrazole-4-carboxamide and N-[1-(2,4-dichlorophenyl)-1-methoxypropan-2-yl]-3-(difluoromethyl)-1-methyl-1H-pyrazole-4-carboxamide.

(3) Respiration inhibitors (respiratory chain inhibitors) acting on complex III of the respiratory chain, for example ametoctradin, amisulbrom, azoxystrobin, cyazofamid, dimoxystrobin, enestroburin, famoxadone, fenamidone, fluoxastrobin, kresoxim-methyl, metominostrobin, orysastrobin, picoxystrobin, pyraclostrobin, pyrametostrobin, pyraoxystrobin, pyribencarb, trifloxystrobin, (2E)-2-(2-{[6-(3-chloro-2-methylphenoxy)-5-fluoropyrimidin-4-yl] oxy}phenyl)-2-(methoxyimino)-N-methylethanamide, (2E)-2-(methoxyimino)-N-methyl-2-(2-{[({(1E)-1-[3-(trifluoromethyl)phenyl]ethylidene}amino)oxy]methyl}phenyl) ethanamide, (2E)-2-(methoxyimino)-N-methyl-2-{2-[(E)-({1-[3-(trifluoromethyl)phenyl]ethoxy}imino)methyl] phenyl}ethanamide, (2E)-2-{2-[({[(1E)-1-(3-{[(E)-1-fluoro-2-phenylethenyl]oxy}phenyl)ethylidene]amino}oxy) methyl]phenyl}-2-(methoxyimino)-N-methylethanamide, (2E)-2-{2-[({[(2E,3E)-4-(2,6-dichlorophenyl)but-3-en-2-ylidene]amino}oxy)methyl]phenyl}-2-(methoxyimino)-N-methylethanamide, 2-chloro-N-(1,1,3-trimethyl-2,3-dihydro-1H-inden-4-yl)pyridine-3-carboxamide, 5-methoxy-2-methyl-4-(2-{[({(1E)-1-[3-(trifluoromethyl)phenyl] ethylidene}amino)oxy]methyl}phenyl)-2,4-dihydro-3H-1, 2,4-triazol-3-one, methyl(2E)-2-{2-[({cyclopropyl[(4-methoxyphenyl)imino]methyl}sulphanyl)methyl]phenyl}-3-methoxyprop-2-enoate, N-(3-ethyl-3,5,5-trimethylcyclohexyl)-3-(formylamino)-2-hydroxybenzamide, 2-{2-[(2,5-dimethylphenoxy)methyl] phenyl}-2-methoxy-N-methylacetamide and (2R)-2-{2-[(2, 5-dimethylphenoxy)methyl]phenyl}-2-methoxy-N-methylacetamide.

(4) Mitosis and cell division inhibitors, for example benomyl, carbendazim, chlorfenazole, diethofencarb, ethaboxam, fluopicolide, fuberidazole, pencycuron, thiabendazole, thiophanate-methyl, thiophanate, zoxamide, 5-chloro-7-(4-methylpiperidin-1-yl)-6-(2,4,6-trifluorophenyl)[1,2,4] triazolo[1,5-a]pyrimidine and 3-chloro-5-(6-chloropyridin-3-yl)-6-methyl-4-(2,4,6-trifluorophenyl)pyridazine.

(5) Compounds with multisite activity, for example Bordeaux mixture, captafol, captan, chlorothalonil, copper formulations such as copper hydroxide, copper naphthenate, copper oxide, copper oxychloride, copper sulphate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propamidine, propineb, sulphur and sulphur preparations, for example calcium polysulphide, thiram, tolylfluanid, zineb and ziram.

(6) Resistance inductors, for example acibenzolar-S-methyl, isotianil, probenazole and tiadinil.

(7) Amino acid and protein biosynthesis inhibitors, for example andoprim, blasticidin-S, cyprodinil, kasugamycin, kasugamycin hydrochloride hydrate, mepanipyrim and pyrimethanil.

(8) ATP production inhibitors, for example fentin acetate, fentin chloride, fentin hydroxide and silthiofam.

(9) Cell wall synthesis inhibitors, for example benthiavalicarb, dimethomorph, flumorph, iprovalicarb, mandipropamid, polyoxins, polyoxorim, validamycin A and valifenalate.

(10) Lipid and membrane synthesis inhibitors, for example biphenyl, chloroneb, dicloran, edifenphos, etridiazole, iodocarb, iprobenfos, isoprothiolane, propamocarb, propamocarb hydrochloride, prothiocarb, pyrazophos, quintozene, tecnazene and tolclofos-methyl.

(11) Melanin biosynthesis inhibitors, for example carpropamid, diclocymet, fenoxanil, phthalide, pyroquilon and tricyclazole.

(12) Nucleic acid synthesis inhibitors, for example benalaxyl, benalaxyl-M (kiralaxyl), bupirimate, clozylacon, dimethirimol, ethirimol, furalaxyl, hymexazol, metalaxyl, metalaxyl-M (mefenoxam), ofurace, oxadixyl, oxolinic acid.

(13) Signal transduction inhibitors, for example chlozolinate, fenpiclonil, fludioxonil, iprodione, procymidone, quinoxyfen and vinclozolin.

(14) Decouplers, for example binapacryl, dinocap, ferimzone, fluazinam and meptyldinocap.

(15) Further compounds, for example benthiazole, bethoxazin, capsimycin, carvone, chinomethionat, chlazafenone, cufraneb, cyflufenamid, cymoxanil, cyprosulfamide, dazomet, debacarb, dichlorophen, diclomezine, difenzoquat, difenzoquat methylsulphate, diphenylamine, ecomat, fenpyrazamine, flumetover, fluoromide, flusulfamide, flutianil, fosetyl-aluminium, fosetyl-calcium, fosetyl-sodium, hexachlorobenzene, irumamycin, methasulfocarb, methyl isothiocyanate, metrafenon, mildiomycin, natamycin, nickel dimethyldithiocarbamate, nitrothal-isopropyl, octhilinone, oxamocarb, oxyfenthiin, pentachlorophenol and salts thereof, phenothrin, phosphoric acid and salts thereof, propamocarb-fosetylate, propanosine-sodium, proquinazid, pyrrolnitrin, tebufloquin, tecloftalam, tolnifanid, triazoxide, trichlamide, zarilamide, 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-methoxyphenoxy)-3,3-dimethylbutan-2-yl 1H-imidazole-1-carboxylate, 2,3,5,6-tetrachloro-4-(methylsulphonyl) pyridine, 2,3-dibutyl-6-chlorothieno[2,3-d]pyrimidin-4 (3H)-one, 2-[5-methyl-3-(trifluoromethyl)-1H-pyrazol-1- yl]-1-(4-{4-[(5R)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, 2-butoxy-6-iodo-3-propyl-4H-chromen-4-one, 2-chloro-5-[2-chloro-1-(2,6-difluoro-4-methoxyphenyl)-4-methyl-1H-imidazol-5-yl]pyridine, 2-phenylphenol and salts thereof, 3,4,5-trichloropyridine-2,6-dicarbonitrile, 3-[5-(4-chlorophenyl)-2,3-dimethyl-1,2-oxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 5-amino-1,3,4-thiadiazole-2-thiol, 5-chloro-N'-phenyl-N'-(prop-2-yn-1-yl)thiophene-2-sulphonohydrazide, 5-methyl-6-octyl[1,2,4]triazolo[1,5-a]pyrimidine-7-amine, ethyl (2Z)-3-amino-2-cyano-3-phenylprop-2-enoate, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloropyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(E)-[(cyclopropylmethoxy)imino][6-(difluoromethoxy)-2,3-difluorophenyl]methyl}-2-phenylacetamide, N-{(Z)-[(cyclopropylmethoxy)imino][6-(difluoromethoxy)-2,3-difluorophenyl]methyl}-2-phenylacetamide, N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, pentyl{6-[({[(1-methyl-1H-tetrazol-5-yl)(phenyl)methylidene]amino}oxy)methyl]pyridin-2-yl}carbamate, phenazine-1-carboxylic acid, quinolin-8-ol and quinolin-8-ol sulphate (2:1).

(16) Further antimicrobially active compounds: (16.1) benthiazole, (16.2) bethoxazine, (16.3) capsimycin, (16.4) carvone, (16.5) chinomethionat, (16.6) pyriofenone (chlazafenone), (16.7) cufraneb, (16.8) cyflufenamid, (16.9) cymoxanil, (16.10) cyprosulfamide, (16.11) dazomet, (16.12) debacarb, (16.13) dichlorophen, (16.14) diclomezine, (16.15) difenzoquat, (16.16) difenzoquat methylsulphate, (16.17) diphenylamine, (16.18) EcoMate, (16.19) fenpyrazamine, (16.20) flumetover, (16.21) fluoroimide, (16.22) flusulfamide, (16.23) flutianil, (16.24) fosetyl-aluminium, (16.25) fosetyl-calcium, (16.26) fosetyl-sodium, (16.27) hexachlorobenzene, (16.28) irumamycin, (16.29) methasulfocarb, (16.30) methyl isothiocyanate, (16.31) metrafenone, (16.32) mildiomycin, (16.33) natamycin, (16.34) nickel dimethyldithiocarbamate, (16.35) nitrothal-isopropyl, (16.37) oxamocarb, (16.38) oxyfenthiin, (16.39) pentachlorophenol and salts, (16.40) phenothrin, (16.41) phosphoric acid and its salts, (16.42) propamocarb-fosetylate, (16.43) propanosine-sodium, (16.44) pyrimorph, (16.45) (2E)-3-(4-tert-butylphenyl)-3-(2-chloropyridin-4-yl)-1-(morpholin-4-yl)prop-2-en-1-one, (16.46) (2Z)-3-(4-tert-butylphenyl)-3-(2-chloropyridin-4-yl)-1-(morpholin-4-yl)prop-2-en-1-one, (16.47) pyrrolnitrin, (16.48) tebufloquin, (16.49) tecloftalam, (16.50) tolnifanide, (16.51) triazoxide, (16.52) trichlamide, (16.53) zarilamid, (16.54) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (16.55) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (16.56) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (16.57) 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (16.58) 1-(4-methoxyphenoxy)-3,3-dimethylbutan-2-yl 1H-imidazole-1-carboxylate, (16.59) 2,3,5,6-tetrachloro-4-(methylsulphonyl)pyridine, (16.60) 2,3-dibutyl-6-chlorothieno[2,3-d]pyrimidin-4(3H)-one, (16.61) 2,6-dimethyl-1H,5H-[1,4]dithiino[2,3-c:5,6-c']dipyrrole-1,3,5,7(2H,6H)-tetrone, (16.62) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, (16.63) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, (16.64) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, (16.65) 2-butoxy-6-iodo-3-propyl-4H-chromen-4-one, (16.66) 2-chloro-5-[2-chloro-1-(2,6-difluoro-4-methoxyphenyl)-4-methyl-1H-imidazol-5-yl]pyridine, (16.67) 2-phenylphenol and salts, (16.68) 3-(4,4,5-trifluoro-3,3-dimethyl-3,4-dihydroisoquinolin-1-yl)quinoline, (16.69) 3,4,5-trichloropyridine-2,6-dicarbonitrile, (16.70) 3-chloro-5-(4-chlorophenyl)-4-(2,6-difluorophenyl)-6-methylpyridazine, (16.71) 4-(4-chlorophenyl)-5-(2,6-difluorophenyl)-3,6-dimethylpyridazine, (16.72) 5-amino-1,3,4-thiadiazole-2-thiol, (16.73) 5-chloro-N'-phenyl-N'-(prop-2-yn-1-yl)thiophene-2-sulphonohydrazide, (16.74) 5-fluoro-2-[(4-fluorobenzyl)oxy]pyrimidine-4-amine, (16.75) 5-fluoro-2-[(4-methylbenzyl)oxy]pyrimidine-4-amine, (16.76) 5-methyl-6-octyl[1,2,4]triazolo[1,5-a]pyrimidine-7-amine, (16.77) ethyl (2Z)-3-amino-2-cyano-3-phenylacrylate, (16.78) N'-(4-{[3-(4-chlorobenzyl)-1,2,4-thiadiazol-5-yl]oxy}-2,5-dimethylphenyl)-N-ethyl-N-methylimidoformamide, (16.79) N-(4-chlorobenzyl)-3-[3-methoxy-4-(prop-2-yn-1-yloxy)phenyl]propanamide, (16.80) N-[(4-chlorophenyl)(cyano)methyl]-3-[3-methoxy-4-(prop-2-yn-1-yloxy)phenyl]propanamide, (16.81) N-[(5-bromo-3-chloropyridin-2-yl)methyl]-2,4-dichloronicotinamide, (16.82) N-[1-(5-bromo-3-chloropyridin-2-yl)ethyl]-2,4-dichloronicotinamide, (16.83) N-[1-(5-bromo-3-chloropyridin-2-yl)ethyl]-2-fluoro-4-iodonicotinamide, (16.84) N-{(E)-[(cyclopropylmethoxy)imino][6-(difluoromethoxy)-2,3-difluorophenyl]methyl}-2-phenylacetamide, (16.85) N-{(Z)-[(cyclopropylmethoxy)imino][6-(difluoromethoxy)-2,3-difluorophenyl]methyl}-2-phenylacetamide, (16.86) N'-{4-[(3-tert-butyl-4-cyano-1,2-thiazol-5-yl)oxy]-2-chloro-5-methylphenyl}-N-ethyl-N-methylimidoformamide, (16.87) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, (16.88) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, (16.89) N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, (16.90) pentyl {6-[({[(1-methyl-1H-tetrazol-5-yl)(phenyl)methylene]amino}oxy)methyl]pyridin-2- yl}carbamate, (16.91) phenazine-1-carboxylic acid, (16.92) quinolin-8-ol, (16.93) quinolin-8-ol sulphate (2:1), (16.94) tert-butyl {6-[({[(1-methyl-1H-tetrazol-5-yl)(phenyl)methylene]amino}oxy)methyl]pyridin-2-yl}carbamate, (16.95) 1-methyl-3-(trifluoromethyl)-N-[2'-(trifluoromethyl)biphenyl-2-yl]-1H-pyrazole-4-carboxamide, (16.96) N-(4'-chlorobiphenyl-2-yl)-3-(difluoromethyl)-1-methyl-1H-pyrazole-4-carboxamide, (16.97) N-(2',4'-dichlorobiphenyl-2-yl)-3-(difluoromethyl)-1-methyl-1H-pyrazole-4-carboxamide, (16.98) 3-(difluoromethyl)-1-methyl-N-[4'-(trifluoromethyl)biphenyl-2-yl]-1H-pyrazole-4-carboxamide, (16.99) N-(2',5'-difluorobiphenyl-2-yl)-1-methyl-3-(trifluoromethyl)-1H-pyrazole-4-carboxamide, (16.100) 3-(difluoromethyl)-1-methyl-N-[4'-(prop-1-yn-1-yl)biphenyl-2-yl]-1H-pyrazole-4-carboxamide, (16.101) 5-fluoro-1,3-dimethyl-N-[4'-(prop-1-yn-1-yl)biphenyl-2-yl]-1H-pyrazole-4-carboxamide, (16.102) 2-chloro-N-[4'-(prop-1-yn-1-yl)biphenyl-2-yl]nicotinamide, (16.103) 3-(difluoromethyl)-N-[4'-(3,3-dimethylbut-1-yn-1-yl)biphenyl-2-yl]-1-methyl-1H-pyrazole-4-carboxamide, (16.104) N-[4'-(3,3-dimethylbut-1-yn-1-yl)biphenyl-2-yl]-5-fluoro-1,3-dimethyl-1H-pyrazole-4-carboxamide, (16.105) 3-(difluoromethyl)-N-(4'-ethynylbiphenyl-2-yl)-1-methyl-1H-pyrazole-4-carboxamide, (16.106) N-(4'-ethynylbiphenyl-2-yl)-5-fluoro-1,3-dimethyl-1H-pyrazole-4-carboxamide, (16.107) 2-chloro-N-(4'-ethynylbiphenyl-2-yl)nicotinamide, (16.108) 2-chloro-N-[4'-(3,3-dimethylbut-1-yn-1-yl)biphenyl-2-yl]nicotinamide, (16.109) 4-(difluoromethyl)-2-methyl-N-[4'-(trifluoromethyl)biphenyl-2-yl]-1,3-thiazole-5-carboxamide, (16.110) 5-fluoro-N-[4'-(3-hydroxy-3-methylbut-1-yn-1-yl)biphenyl-2-yl]-1,3-dimethyl-1H-pyrazole-4-carboxamide, (16.111) 2-chloro-N-[4'-(3-hydroxy-3-methylbut-1-yn-1-yl)biphenyl-2-yl]nicotinamide, (16.112) 3-(difluoromethyl)-N-[4'-(3-methoxy-3-methylbut-1-yn-1-yl)biphenyl-2-yl]-1-methyl-1H-pyrazole-4-carboxamide, (16.113) 5-fluoro-N-[4'-(3-methoxy-3-methylbut-1-yn-1-yl)biphenyl-2-yl]-1,3-dimethyl-1H-pyrazole-4-carboxamide, (16.114) 2-chloro-N-[4'-(3-methoxy-3-methylbut-1-yn-1-yl)biphenyl-2-yl]nicotinamide, (16.115) (5-bromo-2-methoxy-4-methylpyridin-3-yl)(2,3,4-trimethoxy-6-methylphenyl)methanone, (16.116) N-[2-(4-{[3-(4-chlorophenyl)prop-2-yn-1-yl]oxy}-3-methoxyphenyl)ethyl]-N2-(methylsulphonyl)valinamide, (16.117) 4-oxo-4-[(2-phenylethyl)amino]butanoic acid, (16.118) but-3-yn-1-yl {6-[({[(Z)-(1-methyl-1H-tetrazol-5-yl)(phenyl)methylene]amino}oxy)methyl]pyridin-2-yl}carbamate, (16.119) 4-amino-5-fluoropyrimidin-2-ol (mesomeric form: 4-amino-5-fluoropyrimidin-2(1H)-one), (16.120) propyl 3,4,5-trihydroxybenzoate, (16.121) 1,3-dimethyl-N-(1,1,3-trimethyl-2,3-dihydro-1H-inden-4-yl)-1H-pyrazole-4-carboxamide, (16.122) 1,3-dimethyl-N-[(3R)-1,1,3-trimethyl-2,3-dihydro-1H-inden-4-yl]-1H-pyrazole-4-carboxamide, (16.123) 1,3-dimethyl-N-[(3S)-1,1,3-trimethyl-2,3-dihydro-1H-inden-4-yl]-1H-pyrazole-4-carboxamide, (16.124) [3-(4-chloro-2-fluorophenyl)-5-(2,4-difluorophenyl)-1,2-oxazol-4-yl](pyridin-3-yl)methanol, (16.125) (S)-[3-(4-chloro-2-fluorophenyl)-5-(2,4-difluorophenyl)-1,2-oxazol-4-yl](pyridin-3-yl)methanol, (16.126) (R)-[3-(4-chloro-2-fluorophenyl)-5-(2,4-difluorophenyl)-1,2-oxazol-4-yl](pyridin-3-yl)methanol, (16.127) 2-{[3-(2-chlorophenyl)-2-(2,4-difluorophenyl)oxiran-2-yl]methyl}-2,4-dihydro-3H-1,2,4-triazole-3-thione, (16.128) 1-{[3-(2-chlorophenyl)-2-(2,4-difluorophenyl)oxiran-2-yl]methyl}-1H-1,2,4-triazol-5-yl thiocyanate, (16.129) 5-(allylsulphanyl)-1-{[3-(2-chlorophenyl)-2-(2,4-difluorophenyl)oxiran-2-yl]methyl}-1H-1,2,4-triazole, (16.130) 2-[1-(2,4-dichlorophenyl)-5-hydroxy-2,6,6-trimethylheptan-4-yl]-2,4-dihydro-3H-1,2,4-triazole-3-thione, (16.131) 2-{[rel(2R,3S)-3-(2-chlorophenyl)-2-(2,4-difluorophenyl)oxiran-2-yl]methyl}-2,4-dihydro-3H-1,2,4-triazole-3-thione, (16.132) 2-{[rel(2R,3R)-3-(2-chlorophenyl)-2-(2,4-difluorophenyl)oxiran-2-yl]methyl}-2,4-dihydro-3H-1,2,4-triazole-3-thione, (16.133) 1-{[rel(2R,3S)-3-(2-chlorophenyl)-2-(2,4-difluorophenyl)oxiran-2-yl]methyl}-1H-1,2,4-triazol-5-yl thiocyanate, (16.134) 1-{[rel(2R,3R)-3-(2-chlorophenyl)-2-(2,4-difluorophenyl)oxiran-2-yl]methyl}-1H-1,2,4-triazol-5-yl thiocyanate, (16.135) 5-(allylsulphanyl)-1-{[rel(2R,3S)-3-(2-chlorophenyl)-2-(2,4-difluorophenyl)oxiran-2-yl]methyl}-1H-1,2,4-triazole, (16.136) 5-(allylsulphanyl)-1-{[rel(2R,3R)-3-(2-chlorophenyl)-2-(2,4-difluorophenyl)oxiran-2-yl]methyl}-1H-1,2,4-triazole, (16.137) 2-[(2S,4S,5S)-1-(2,4-dichlorophenyl)-5-hydroxy-2,6,6-trimethylheptan-4-yl]-2,4-dihydro-3H-1,2,4-triazole-3-thione, (16.138) 2-[(2R,4S,5S)-1-(2,4-dichlorophenyl)-5-hydroxy-2,6,6-trimethylheptan-4-yl]-2,4-dihydro-3H-1,2,4-triazole-3-thione, (16.139) 2-[(2R,4R,5R)-1-(2,4-dichlorophenyl)-5-hydroxy-2,6,6-trimethylheptan-4-yl]-2,4-dihydro-3H-1,2,4-triazole-3-thione, (16.140) 2-[(2S,4R,5R)-1-(2,4-dichlorophenyl)-5-hydroxy-2,6,6-trimethylheptan-4-yl]-2,4-dihydro-3H-1,2,4-triazole-3-thione, (16.141) 2-[(2S,4S,5R)-1-(2,4-dichlorophenyl)-5-hydroxy-2,6,6-trimethylheptan-4-yl]-2,4-dihydro-3H-1,2,4-triazole-3-thione, (16.142) 2-[(2R,4S,5R)-1-(2,4-dichlorophenyl)-5-hydroxy-2,6,6-trimethylheptan-4-yl]-2,4-dihydro-3H-1,2,4-triazole-3-thione, (16.143) 2-[(2R,4R,5S)-1-(2,4-dichlorophenyl)-5-hydroxy-2,6,6-trimethylheptan-4-yl]-2,4-dihydro-3H-1,2,4-triazole-3-thione, (16.144) 2-[(2S,4R,5S)-1-(2,4-dichlorophenyl)-5-hydroxy-2,6,6-trimethylheptan-4-yl]-2,4-dihydro-3H-1,2,4-triazole-3-thione, (16.145) 2-fluoro-6-(trifluoromethyl)-N-(1,1,3-trimethyl-2,3-dihydro-1H-inden-4-yl)benzamide, (16.146) 2-(6-benzylpyridin-2-yl)quinazoline, (16.147) 2-[6-(3-fluoro-4-methoxyphenyl)-5-methylpyridin-2-yl]quinazoline, (16.148) 3-(4,4-difluoro-3,3-dimethyl-3,4-dihydroisoquinolin-1-yl)quinoline, (16.149) abscisic acid.

The active compounds according to the invention can furthermore be combined with microorganisms. The microorganisms, given good plant tolerance, favourable homeotherm toxicity and good environmental compatibility, are suitable for protecting plants and plant organs, for increasing harvest yields, for improving the quality of the harvested material and for controlling animal pests, especially insects, arachnids, helminths, nematodes and molluscs, which are encountered in agriculture, in horticulture, in animal husbandry, in forests, in gardens and leisure facilities, in the protection of stored products and of materials, and in the hygiene sector. They can preferably be used as crop protection compositions. They are active against normally sensitive and resistant species and against all or some stages of development. The abovementioned microorganisms include:

microorganisms from the group of the bacteria, for example *Bacillus agri, Bacillus aizawai, Bacillus albolactis, Bacillus amyloliquefaciens*, in particular the strain *B. amyloliquefaciens* IN937a, or strain FZB42, *Bacillus cereus*, in particular spores of *B. cereus* CNCM I-1562, *Bacillus coagulans, Bacillus endoparasiticus, Bacillus endorhythmos, Bacillus firmus*, in particular spores of *B. firmus* CNCM I-1582, *Bacillus kurstaki, Bacillus lacticola, Bacillus lactimorbus, Bacillus lactis, Bacillus laterosporus, Bacillus lentimorbus, Bacillus licheniformis, Bacillus medusa, Bacillus megaterium, Bacillus metiens, Bacillus natto, Bacillus nigrificans, Bacillus popillae, Bacillus pumilus*, in particular the strain *B. pumilus* GB34, *Bacillus siamensis, Bacillus sphaericus, Bacillus subtilis*, in particular the strain *B. subtilis* GB03, or the strain *B. subtilis* var. *amyloliquefaciens* FZB24, *Bacillus thuringiensis*, in particular *B. thuringiensis* var. *israelensis* or *B. thuringiensis* ssp. *aizawai* strain ABTS-1857 or *B. thuringiensis* ssp *kurstaki* strain HD-1, *B. thuringiensis* var. san diego, *B. thuringiensis* var. *tenebrinos, Bacillus uniflagellatus, Delftia acidovorans*, in particular strain RAY209, *Lysobacter antibioticus*, in particular strain 13-1, *Metarhizium anisopliae, Pseudomonas chlororaphis*, in particular strain MA342, *Pseudomonas proradix, Streptomyces galbus*, in particular strain K61, *Streptomyces griseoviridis;* microorganisms from the group of the fungi, for example *Ampelomyces quisqualis*, in particular strain AQ10, *Aureobasidium pullulans*, in particular blastospores of strain DSM14940 or blastospores of strain DSM14941 or mixtures thereof, *Beauveria bassiana*, in particular strain ATCC74040, *Beauveria brongniartii, Candida oleophila*, in particular strain O, *Coniothyrium minitans*, in particular strain CON/M/91-8, *Dilophosphora alopecuri, Gliocladium catenulatum*, in particular strain J1446; *Hirsutella thompsonii, Lagenidium giganteum, Lecanicillium lecanii* (previously known as *Verticillium lecanii*), in particular conidia of strain KV01, *Metarhizium anisopliae*, in particular strain F52, *Metschnikovia fructicola*, in particular strain NRRL Y-30752, *Microsphaeropsis ochracea, Muscodor albus*, in particular strain QST20799, *Nomuraea rileyi, Paecilomyces lilacinus*, in particular spores of strain *P. lilacinus* 251, *Penicillium bilaii*, in particular strain ATCC22348, *Pichia anomala*, in particular strain WRL-076, *Pseudozyma flocculosa*, in particular strain PF-A22 UL, *Pytium oligandrum* DV74, *Trichoderma asperellum*, in particular strain ICC012, *Trichoderma harzianum, insbesondere T. harzianum* T39, *Verticillium lecanii*, in particular the strains DAOM198499 and DAOM216596;

insecticidal microorganisms from the group of the protozoa, for example *Nosema locustae, Vairimorpha;* insecticidal microorganisms from the group of the viruses, for example Gypsy moth (*Lymantria dispar*) nuclear polyhedrosis virus (NPV), Tussock moth (Lymantriidae) NPV, *Heliothis* NPV, Pine sawfly (Neodiprion) NPV, Codling moth (*Cydia pomonella*) granulosis virus (GV);

microorganisms from the group of the entomopathogenic nematodes, for example *Steinernema scapterisci, Steinernema feltiae (Neoaplectana carpocapsae), Heterorhabditis heliothidis, Xenorhabdus luminescence.*

The active compounds identified here by their common names are known and are described, for example, in the pesticide handbook ("The Pesticide Manual" 14th Ed., British Crop Protection Council 2006) or can be found on the Internet (e.g. http://www.alanwood.net/pesticides).

All mixing partners mentioned in classes (1) to (16) can, if they are capable on the basis of their functional groups, optionally form salts with suitable bases or acids.

Finally, it has been found that the novel compounds of the formula (I), whilst being well tolerated by plants, with favourable homeotherm toxicity and good environmental compatibility, are suitable in particular for controlling animal pests, especially arthropods, insects, arachnids, helminths, nematodes and molluscs, which are encountered in agriculture, in forests, in the protection of stored products and materials and in the hygiene sector, or in the animal health sector. The compounds according to the invention can likewise be used in the animal health sector, for example for controlling endo- and/or ectoparasites.

The compounds according to the invention can be used as agents for controlling animal pests, preferably as crop protection agents. They are active against normally sensitive and resistant species and against all or some stages of development.

The compounds according to the invention can be converted into generally known formulations. In general, such formulations comprise from 0.01 to 98% by weight of active compound, preferably from 0.5 to 90% by weight.

The compounds according to the invention can be present in their commercially available formulations and in the use forms, prepared from these formulations, as a mixture with other active compounds or synergists. Synergists are compounds which enhance the action of the active compounds, without any need for the synergist added to be active itself.

The active compound content of the use forms prepared from the commercially available formulations may vary within wide limits. The active compound concentration of the use forms may be from 0.00000001 to 95% by weight of active compound, preferably from 0.00001 to 1% by weight.

The compounds are employed in a customary manner appropriate for the use forms.

All plants and plant parts can be treated in accordance with the invention. Plants are understood here to mean all plants and plant populations, such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Plant parts are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. The plant parts also include harvested material and vegetative and generative propagation material, for example cuttings, tubers, rhizomes, slips and seed.

The treatment according to the invention of the plants and plant parts with the active compounds is effected directly or by allowing them to act on the surroundings, habitat or storage space thereof by the customary treatment methods, for example by dipping, spraying, evaporating, fogging, scattering, painting on, injecting, and, in the case of propagation material, especially in the case of seeds, also by applying one or more coats.

As already mentioned above, it is possible to treat all plants and their parts according to the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts" and "parts of plants" or "plant parts" have been elucidated above.

More preferably, plants of the plant cultivars which are each commercially available or in use are treated in accordance with the invention. Plant cultivars are to be understood as meaning plants having new properties ("traits") and which have been obtained by conventional breeding, by mutagenesis or by recombinant DNA techniques. They may be cultivars, biotypes and genotypes.

In the animal health sector, i.e. in the field of veterinary medicine, the active compounds according to the present invention act against animal parasites, especially ectoparasites or endoparasites. The term "endoparasites" includes especially helminths such as cestodes, nematodes or trematodes, and protozoa such as coccidia. Ectoparasites are typically and preferably arthropods, especially insects such as flies (biting and licking), parasitic fly larvae, lice, hair lice, bird lice, fleas and the like; or acaricides such as ticks, for example hard ticks or soft ticks, or mites such as scab mites, harvest mites, bird mites and the like.

It has also been found that the compounds according to the invention have strong insecticidal action against insects which destroy industrial materials. Industrial materials in the present context are understood to mean inanimate materials, such as preferably plastics, adhesives, sizes, papers and cards, leather, wood, processed wood products and coating compositions.

In addition, the compounds according to the invention can be used as antifouling compositions, alone or in combinations with other active compounds.

The active compounds are also suitable for controlling animal pests in the domestic sector, in the hygiene sector and in the protection of stored products, especially insects, arachnids and mites, which are found in enclosed spaces, for example homes, factory halls, offices, vehicle cabins and the like. They can be used to control these pests alone or in combination with other active compounds and auxiliaries in domestic insecticide products. They are effective against sensitive and resistant species, and against all developmental stages.

Plants are to be understood to mean all plant species, plant cultivars and plant populations such as wanted and unwanted wild plants or crop plants. Crop plants to be treated according to the invention are plants which occur naturally or those which are obtained by conventional breeding and optimization methods or by biotechnological and genetic engineering methods or by combining the methods mentioned above. The term crop plant does, of course, also include transgenic plants.

Plant cultivars are to be understood as meaning plants having new properties (traits) and which have been obtained by conventional breeding, by mutagenesis or by recombinant DNA techniques or a combination thereof. They can be cultivars, varieties, bio- or genotypes.

Plant parts are understood to mean all parts and organs of plants above and below the ground, such as shoot, leaf, flower and root, in particular leaves, needles, stalks, stems, flowers, fruit-bodies, fruits, seeds, roots, tubers and rhizomes. The term plant parts also includes harvested material and vegetative and generative propagation material, for example cuttings, tubers, rhizomes, slips and seeds or seed.

In one embodiment according to the invention, naturally occurring plant species and plant cultivars, or those obtained by conventional breeding and optimization methods (e.g. crossing or protoplast fusion), and also parts thereof, are treated.

In a further embodiment according to the invention, transgenic plants obtained by genetic engineering methods, if appropriate in combination with conventional methods, and parts thereof are treated.

The treatment method according to the invention is preferably employed for genetically modified organisms such as, for example, plants or plant parts.

Genetically modified plants, so-called transgenic plants, are plants in which a heterologous gene has been stably integrated into the genome.

The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing (an)other gene(s) which (is) are present in the plant (using, for example, antisense technology, cosuppression technology or RNA interference—RNAi—technology). A heterologous gene that is present in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. For example, the following effects which exceed the effects actually to be expected are possible: reduced application rates and/or widened spectrum of activity and/or increased efficacy of the active compounds and compositions which can be used in accordance with the invention, better plant growth, increased tolerance to high or low temperatures, increased tolerance to drought or to water or soil salinity, increased flowering performance, easier harvesting, accelerated maturation, higher harvest yields, bigger fruits, greater plant height, greener leaf colour, earlier flowering, higher quality and/or a higher nutritional value of the harvested products, higher sugar concentration within the fruits, better storage stability and/or processability of the harvested products.

At certain application rates, the active compound combinations according to the invention may also have a strengthening effect on plants. Accordingly, they are suitable for mobilizing the defence system of the plant against attack by unwanted phytopathogenic fungi and/or microorganisms and/or viruses. This may optionally be one of the reasons for the enhanced activity of the combinations according to the invention, for example against fungi. Plant-strengthening (resistance-inducing) substances are to be understood as meaning, in the present context, those substances or combinations of substances which are capable of stimulating the defence system of plants in such a way that, when subsequently inoculated with unwanted phytopathogenic fungi and/or microorganisms and/or viruses, the treated plants display a substantial degree of resistance to these unwanted phytopathogenic fungi and/or microorganisms and/or viruses. In the present case, unwanted phytopathogenic fungi and/or microorganisms and/or viruses are understood as meaning phytopathogenic fungi, bacteria and viruses. The substances according to the invention can therefore be used for protection of plants from attack by the pathogens mentioned within a certain period of time after treatment. The period of time within which protection is effected generally extends from 1 to 10 days, preferably 1 to 7 days, after the treatment of the plants with the active compounds.

Plants which are furthermore preferably treated according to the invention are resistant against one or more biotic stress factors, i.e. said plants have a better defence against animal and microbial pests, such as nematodes, insects, mites, phytopathogenic fungi, bacteria, viruses and/or viroids.

In addition to the plants and plant cultivars mentioned above, it is also possible to treat those according to the invention which are resistant to one or more abiotic stress factors.

Abiotic stress conditions may include, for example, drought, cold temperature exposure, heat exposure, osmotic stress, waterlogging, increased soil salinity, increased exposure to minerals, exposure to ozone, exposure to strong light, limited availability of nitrogen nutrients, limited availability of phosphorus nutrients or shade avoidance.

Plants and plant cultivars which may also be treated according to the invention are those plants characterized by enhanced yield characteristics Enhanced yield in these plants may be the result of, for example, improved plant physiology, improved plant growth and development, such as water use efficiency, water retention efficiency, improved nitrogen use, enhanced carbon assimilation, improved photosynthesis, increased germination efficiency and accelerated maturation. Yield can also be affected by improved plant architecture (under stress and non-stress conditions), including early flowering, flowering control for hybrid seed production, seedling vigour, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and oil composition, nutritional value, reduction in antinutritional compounds, improved processability and better storage stability.

Plants that may be treated according to the invention are hybrid plants that already express the characteristics of heterosis or hybrid vigour which results in generally higher yield, vigour, health and resistance towards biotic and abiotic stresses. Such plants are typically made by crossing an inbred male-sterile parent line (the female parent) with another inbred male-fertile parent line (the male parent). Hybrid seed is typically harvested from the male-sterile plants and sold to growers. Male-sterile plants can sometimes (e.g. in maize) be produced by detasseling, (i.e. the mechanical removal of the male reproductive organs or male flowers) but, more typically, male sterility is the result of genetic determinants in the plant genome. In that case, and especially when seed is the desired product to be harvested from the hybrid plants, it is typically useful to ensure that male fertility in hybrid plants, which contain the genetic determinants responsible for male sterility, is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described for *Brassica* species. However, genetic determinants for male sterility can also be located in the nuclear genome. Male-sterile plants can also be obtained by plant biotechnology methods such as genetic engineering. A particularly useful means of obtaining male-sterile plants is described in WO 89/10396, in which, for example, a ribonuclease such as a barnase is selectively expressed in the tapetum cells in the stamens. Fertility can then be restored by expression in the tapetum cells of a ribonuclease inhibitor such as barstar.

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. Thus, for example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium*, the CP4 gene of the bacterium *Agrobacterium* sp., the genes encoding a petunia EPSPS, a tomato EPSPS, or an *Eleusine* EPSPS. It can also be a mutated EPSPS. Glyphosate-tolerant plants can also be obtained by expressing a gene that encodes a glyphosate oxidoreductase enzyme. Glyphosate-tolerant plants can also be obtained by expressing a gene that encodes a glyphosate acetyltransferase enzyme. Glyphosate-tolerant plants can also be obtained by selecting plants containing naturally-occurring mutations of the above-mentioned genes.

Other herbicide-resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant of the glutamine synthase enzyme that is resistant to inhibition. One such efficient detoxifying enzyme is, for example, an enzyme encoding a phosphinothricin acetyltransferase (such as the bar or pat protein from *Streptomyces* species for example). Plants expressing an exogenous phosphinothricin acetyltransferase have been described.

Further herbicide-tolerant plants are also plants that have been made tolerant to the herbicides inhibiting the enzyme hydroxyphenylpyruvate dioxygenase (HPPD). Hydroxyphenylpyruvate dioxygenases are enzymes that catalyse the reaction in which para-hydroxyphenylpyruvate (HPP) is converted to homogentisate. Plants tolerant to HPPD inhibitors can be transformed with a gene encoding a naturally-occurring resistant HPPD enzyme, or a gene encoding a mutated HPPD enzyme. Tolerance to HPPD inhibitors can also be obtained by transforming plants with genes encoding certain enzymes enabling the formation of homogentisate despite the inhibition of the native HPPD enzyme by the HPPD inhibitor. Tolerance of plants to HPPD inhibitors can also be improved by transforming plants with a gene encoding an enzyme prephenate dehydrogenase in addition to a gene encoding an HPPD-tolerant enzyme.

Further herbicide-resistant plants are plants that have been made tolerant to acetolactate synthase (ALS) inhibitors. Known ALS inhibitors include, for example, sulphonylurea, imidazolinone, triazolopyrimidines, pyrimidinyl oxy(thio) benzoates, and/or sulphonylaminocarbonyltriazolinone herbicides. Different mutations in the ALS enzyme (also known as acetohydroxy acid synthase, AHAS) are known to confer tolerance to different herbicides and groups of herbicides. The production of sulphonylurea-tolerant plants and imidazolinone-tolerant plants has been described in the international publication WO 1996/033270. Further sulphonylurea- and imidazolinone-tolerant plants have also been described, for example, in WO 2007/024782.

Other plants tolerant to imidazolinone and/or sulphonylurea can be obtained by induced mutagenesis, selection in cell cultures in the presence of the herbicide or mutation breeding.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation or by selection of plants containing a mutation imparting such insect resistance.

The term "insect-resistant transgenic plant", as used herein, includes any plant containing at least one transgene comprising a coding sequence encoding:
1) an insecticidal crystal protein from *Bacillus thuringiensis* or an insecticidal portion thereof, such as the insecticidal crystal proteins compiled online at: http://www.lifesci.sussex.ac.uk/Home/Neil_Crickmore/Bt/, or insecticidal portions thereof, e.g., proteins of the Cry protein classes Cry1Ab, Cry1Ac, Cry1F, Cry2Ab, Cry3Ae, or Cry3Bb or insecticidal portions thereof; or
2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins; or
3) a hybrid insecticidal protein comprising parts of two different insecticidal crystal proteins from *Bacillus thuringiensis*, such as a hybrid of the proteins of 1) above or a hybrid of the proteins of 2) above, e.g., the Cry1A.105 protein produced by maize event MON98034 (WO 2007/027777); or
4) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced into the encoding DNA during cloning or transformation, such as the Cry3Bb1 protein in maize events MON863 or MON88017, or the Cry3A protein in maize event MIR 604;
5) an insecticidal secreted protein from *Bacillus thuringiensis* or *Bacillus cereus*, or an insecticidal portion thereof, such as the vegetative insecticidal proteins (VIP) listed at: http://www.lifesci.sussex.ac.uk/Home/Neil_Crickmore/Bt/vip.html, for example proteins from the VIP3Aa protein class; or
6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins;
7) a hybrid insecticidal protein comprising parts from different secreted proteins from *Bacillus thuringiensis* oder *Bacillus cereus*, such as a hybrid of the proteins in 1) above or a hybrid of the proteins in 2) above; or
8) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced into the encoding DNA during cloning or transformation (while still encoding an insecticidal protein), such as the VIP3Aa protein in cotton event COT 102.

Of course, an insect-resistant transgenic plant, as used herein, also includes any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected, or to delay insect resistance development to the plants by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stress factors. Such plants can be obtained by genetic transformation, or by selection of plants containing a mutation imparting such stress resistance. Particularly useful stress tolerant plants include:
a. plants which contain a transgene capable of reducing the expression and/or the activity of the poly(ADP-ribose) polymerase (PARP) gene in the plant cells or plants;
b. plants which contain a stress tolerance-enhancing transgene capable of reducing the expression and/or the activity of the PARG encoding genes of the plants or plant cells;
c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase.

Plants or plant cultivars (obtained by plant biotechnology methods such as genetic engineering) which may also be treated according to the invention show altered quantity, quality and/or storage stability of the harvested product and/or altered properties of specific ingredients of the harvested product such as, for example:
1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this modified starch is better suited for special applications;
2) transgenic plants which synthesize non starch carbohydrate polymers or which synthesize non starch carbohydrate polymers with altered properties in comparison to wild type plants without genetic modification. Examples are plants which produce polyfructose, especially of the inulin and levan type, plants which produce alpha-1,4-glucans, plants which produce alpha-1,6-branched alpha-1,4-glucans, and plants producing alternan;
3) transgenic plants which produce hyaluronan.

Plants or plant cultivars (obtained by plant biotechnology methods such as genetic engineering) which may also be treated according to the invention are plants, such as cotton plants, with altered fibre characteristics. Such plants can be obtained by genetic transformation, or by selection of plants containing a mutation imparting such altered fibre characteristics and include:
a) plants, such as cotton plants, containing an altered form of cellulose synthase genes;
b) plants, such as cotton plants, containing an altered form of rsw2 or rsw3 homologous nucleic acids;
c) plants, such as cotton plants, with increased expression of sucrose phosphate synthase;
d) plants, such as cotton plants, with increased expression of sucrose synthase;
e) plants, such as cotton plants, wherein the timing of the plasmodesmatal gating at the basis of the fibre cell is altered, for example through downregulation of fibre-selective β-1,3-glucanase;
f) plants, such as cotton plants, having fibers with altered reactivity, e.g. through the expression of N-acetylglucosaminetransferase gene including nodC, and chitin synthase genes.

Plants or plant cultivars (obtained by plant biotechnology methods such as genetic engineering) which may also be treated according to the invention are plants, such as oilseed rape or related *Brassica* plants, with altered oil profile characteristics. Such plants can be obtained by genetic transformation or by selection of plants containing a mutation imparting such altered oil characteristics and include:
a) plants, such as oilseed rape plants, which produce oil having a high oleic acid content;
b) plants, such as oilseed rape plants, which produce oil having a low linolenic acid content;
c) plants, such as oilseed rape plants, producing oil having a low level of saturated fatty acids.

Particularly useful transgenic plants which may be treated according to the invention are plants which comprise one or more genes which encode one or more toxins and are the transgenic plants available under the following trade names: YIELD GARD® (for example maize, cotton, soya beans), KnockOut® (for example maize), BiteGard® (for example maize), BT-Xtra® (for example maize), StarLink® (for example maize), Bollgard® (cotton), Nucotn® (cotton), Nucotn 33B® (cotton), NatureGard® (for example maize), Protecta® and NewLeaf® (potato). Examples of herbicide-tolerant plants which may be mentioned are maize varieties, cotton varieties and soya bean varieties which are available under the following trade names: Roundup Ready® (tolerance to glyphosate, for example maize, cotton, soya beans), Liberty Link® (tolerance to phosphinothricin, for example oilseed rape), IMI® (tolerance to imidazolinone) and SCS® (tolerance to sulphonylurea, for example maize). Herbicide-resistant plants (plants bred in a conventional manner for herbicide tolerance) which may be mentioned include the varieties sold under the name Clearfield® (for example maize).

Particularly useful transgenic plants which may be treated according to the invention are plants containing transformation events, or a combination of transformation events, and that are listed for example in the databases for various national or regional regulatory agencies (see for example http://gmoinfo.jrc.it/gmp_browse.aspx and http://www.agbios.com/dbase.php).

Treatment according to the invention of the plants and plant parts with the active compound combinations is carried out directly or by allowing the compounds to act on their surroundings, environment or storage space by the customary treatment methods, for example by immersion, spraying, evaporation, fogging, scattering, painting on and, in the case of propagation material, in particular in the case of seeds, also by applying one or more coats.

The mixtures according to the invention are particularly suitable for the treatment of seed. Here, mention may preferably be made of the combinations according to the invention mentioned above as preferred or particularly preferred. Thus, most of the damage to crop plants which is caused by pests occurs as early as when the seed is infested during storage and after the seed is introduced into the soil, and during and immediately after germination of the plants. This phase is particularly critical since the roots and shoots of the growing plant are particularly sensitive and even minor damage can lead to the death of the whole plant. Protecting the seed and the germinating plant by the use of suitable compositions is therefore of particularly great interest.

The control of pests by treating the seed of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with the additional application of crop protection compositions after sowing or after emergence of the plants. It is furthermore desirable to optimize the amount of active compound employed in such a way as to provide optimum protection for the seed and the germinating plant from attack by pests, but without damaging the plant itself by the active compound employed. In particular, methods for the treatment of seed should also take into consideration the intrinsic insecticidal properties of transgenic plants in order to achieve optimum protection of the seed and also the germinating plant with a minimum of crop protection compositions being employed.

The present invention therefore in particular also relates to a method for the protection of seed and germinating plants from attack by pests, by treating the seed with a composition according to the invention. The invention likewise relates to the use of the compositions according to the invention for the treatment of seed for protecting the seed and the resulting plant from pests. The invention further relates to seed which has been treated with a composition according to the invention for protection from pests.

One of the advantages of the present invention is that the particular systemic properties of the compositions according to the invention mean that treatment of the seed with these compositions not only protects the seed itself, but also the resulting plants after emergence, from pests. In this way, the immediate treatment of the crop at the time of sowing or shortly thereafter can be dispensed with.

A further advantage is the synergistically increased insecticidal activity of the compositions according to the invention in comparison with the individual insecticidally active compound, which exceeds the expected activity of the two active compounds when applied individually. Also advantageous is the synergistic enhancement of the fungicidal activity of the compositions according to the invention compared with the individual fungicidally active compound, which exceeds the expected activity of the active compound applied individually. This makes possible an optimization of the amount of active compounds employed.

Furthermore, it must be considered as advantageous that the mixtures according to the invention can also be employed in particular in transgenic seed, the plants arising from this seed being capable of expressing a protein directed against pests. By treating such seed with the compositions according to the invention, certain pests can be controlled merely by the expression of the, for example, insecticidal protein, and additionally damage to the seed may be averted by the compositions according to the invention.

The compositions according to the invention are suitable for protecting seed of any plant variety as already mentioned above which is employed in agriculture, in the greenhouse, in forests or in horticulture. In particular, this takes the form of seed of maize, peanut, canola, oilseed rape, poppy, soya, cotton, beet (for example sugar beet and fodder beet), rice, millet, wheat, barley, oats, rye, sunflower, tobacco, potatoes or vegetables (for example tomatoes, cabbage species). The compositions according to the invention are likewise suitable for treating the seed of fruit plants and vegetables as already mentioned above. The treatment of the seed of maize, soya, cotton, wheat and canola or oilseed rape is of particular importance.

As already mentioned above, the treatment of transgenic seed with a composition according to the invention is also of particular significance. This takes the form of seed of plants which, as a rule, comprise at least one heterologous gene which governs the expression of a polypeptide with in particular insecticidal properties. In this context, the heterologous genes in transgenic seed may be derived from microorganisms such as *Bacillus, Rhizobium, Pseudomonas, Serratia, Trichoderma, Clavibacter, Glomus* or *Gliocladium*. The present invention is particularly suitable for the treatment of transgenic seed which comprises at least one heterologous gene originating from *Bacillus* sp. and whose gene product shows activity against the European corn borer and/or the corn root worm. The gene involved is more preferably a heterologous gene which originates from *Bacillus thuringiensis*.

Within the context of the present invention, the composition according to the invention is applied to the seed either alone or in a suitable formulation. Preferably, the seed is treated in a state in which it is stable enough to avoid damage during treatment. In general, the seed can be treated at any time between harvest and sowing. The seed usually used has been separated from the plant and freed from cobs, shells, stalks, coats, hairs or the flesh of the fruits.

When treating the seed, it generally has to be ensured that the amount of the composition according to the invention applied to the seed and/or the amount of further additives is selected such that the germination of the seed is not impaired, or that the resulting plant is not damaged. This must be ensured particularly in the case of active compounds which can exhibit phytotoxic effects at certain application rates.

In addition, the compounds according to the invention can be used to control a multitude of different pests, including, for example, harmful sucking insects, biting insects and other pests which are plant parasites, stored material pests, pests which destroy industrial materials, and hygiene pests including parasites in the animal health sector, and for the control thereof, for example the elimination and eradication thereof. The present invention thus also includes a method for controlling pests.

In the animal health sector, i.e. in the field of veterinary medicine, the active compounds according to the present invention act against animal parasites, especially ectoparasites or endoparasites. The term "endoparasites" includes especially helminths such as cestodes, nematodes or trematodes, and protozoa such as coccidia. Ectoparasites are typically and preferably arthropods, especially insects such as flies (biting and licking), parasitic fly larvae, lice, hair lice, bird lice, fleas and the like; or acaricides such as ticks, for example hard ticks or soft ticks, or mites such as scab mites, harvest mites, bird mites and the like.

These parasites include:

From the order of the Anoplurida, for example, *Haematopinus* spp., *Linognathus* spp., *Pediculus* spp., *Phthirus* spp., *Solenopotes* spp.; specific examples are: *Linognathus setosus, Linognathus vituli, Linognathus ovillus, Linognathus oviformis, Linognathus pedalis, Linognathus stenopsis, Haematopinus asini macrocephalus, Haematopinus eurysternus, Haematopinus suis, Pediculus humanus capitis, Pediculus humanus corporis, Phylloera vastatrix, Phthirus pubis, Solenopotes capillatus;*

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; specific examples are: *Bovicola bovis, Bovicola ovis, Bovicola limbata, Damalina bovis, Trichodectes canis, Felicola subrostratus, Bovicola caprae, Lepikentron ovis, Werneckiella equi;*

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; specific examples are: *Aedes aegypti, Aedes albopictus, Aedes taeniorhynchus, Anopheles gambiae, Anopheles maculipennis, Calliphora erythrocephala, Chrysozona pluvialis, Culex quinquefasciatus, Culex pipiens, Culex tarsalis, Fannia canicularis, Sarcophaga carnaria, Stomoxys calcitrans, Tipula paludosa, Lucilia cuprina, Lucilia sericata, Simulium reptans, Phlebotomus papatasi, Phlebotomus longipalpis, Odagmia ornata, Wilhelmia equina, Boophthora erythrocephala, Tabanus bromius, Tabanus spodopterus, Tabanus atratus, Tabanus sudeticus, Hybomitra ciurea, Chrysops caecutiens, Chrysops relictus, Haematopota pluvialis, Haematopota italica, Musca autumnalis, Musca domestica, Haematobia irritans irritans, Haematobia irritans exigua, Haematobia stimulans, Hydrotaea irritans, Hydrotaea albipuncta, Chrysomya chloropyga, Chrysomya bezziana, Oestrus ovis, Hypoderma bovis, Hypoderma lineatum, Przhevalskiana silenus, Dermatobia hominis, Melophagus ovinus, Lipoptena capreoli, Lipoptena cervi, Hippobosca variegata, Hippobosca equina, Gasterophilus intestinalis, Gasterophilus haemorroidalis, Gasterophilus inermis, Gasterophilus nasalis, Gasterophilus nigricornis, Gasterophilus pecorum, Braula coeca;*

From the order of the Siphonapterida, for example, *Pulex* spp., *Ctenocephalides* spp., *Tunga* spp., *Xenopsylla* spp., *Ceratophyllus* spp.; specific examples are: *Ctenocephalides canis, Ctenocephalides felis, Pulex irritans, Tunga penetrans, Xenopsylla cheopis;*

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana, Blattela germanica* and *Supella* spp. (e.g. *Suppella longipalpa*);

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Rhipicephalus (Boophilus)* spp., *Dermacentor* spp., *Haemophysalis* spp., *Hyalomma* spp., *Dermanyssus* spp., *Rhipicephalus* spp. (the original genus of multihost ticks), *Ornithonyssus* spp., *Pneumonyssus* spp., *Raillietia* spp., *Pneumonyssus* spp., *Sternostoma* spp., *Varroa* spp., *Acarapis* spp.; specific examples are: *Argas persicus, Argas reflexus, Ornithodorus moubata, Otobius megnini, Rhipicephalus (Boophilus) microplus, Rhipicephalus (Boophilus) decoloratus, Rhipicephalus (Boophilus) annulatus, Rhipicephalus (Boophilus) calceratus, Hyalomma anatolicum, Hyalomma aegypticum, Hyalomma marginatum, Hyalomma transiens, Rhipicephalus evertsi, Ixodes ricinus, Ixodes hexagonus, Ixodes canisuga, Ixodes pilosus, Ixodes rubicundus, Ixodes scapularis, Ixodes holocyclus, Haemaphysalis concinna, Haemaphysalis punctata, Haemaphysalis cinnabarina, Haemaphysalis otophila, Haemaphysalis leachi, Haemaphysalis longicorni, Dermacentor marginatus, Dermacentor reticulatus, Dermacentor pictus, Dermacentor albipictus, Dermacentor andersoni, Dermacentor variabilis, Hyalomma mauritanicum, Rhipicephalus sanguineus, Rhi-* picephalus bursa, Rhipicephalus appendiculatus, Rhipicephalus capensis, Rhipicephalus turanicus, Rhipicephalus zambeziensis, Amblyomma americanum, Amblyomma variegatum, Amblyomma maculatum, Amblyomma hebraeum, Amblyomma cajennense, Dermanyssus gallinae, Ornithonyssus bursa, Ornithonyssus sylviarum, Varroa jacobsoni;

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.; specific examples are: *Cheyletiella yasguri, Cheyletiella blakei, Demodex canis, Demodex bovis, Demodex ovis, Demodex caprae, Demodex equi, Demodex caballi, Demodex suis, Neotrombicula autumnalis, Neotrombicula desaleri, Neoschongastia xerothermobia, Trombicula akamushi, Otodectes cynotis, Notoedres cati, Sarcoptis canis, Sarcoptes bovis, Sarcoptes ovis, Sarcoptes rupicaprae (=S. caprae), Sarcoptes equi, Sarcoptes suis, Psoroptes ovis, Psoroptes cuniculi, Psoroptes equi, Chorioptes bovis, Psoergates ovis, Pneumonyssoidic mange, Pneumonyssoides caninum, Acarapis woodi.*

The active compounds according to the invention are also suitable for controlling arthropods, helminths and protozoa which attack animals. The animals include agricultural livestock, for example cattle, sheep, goats, horses, pigs, donkeys, camels, buffalo, rabbits, chickens, turkeys, ducks, geese, cultured fish, honey bees. The animals also include domestic animals—also referred to as companion animals—for example dogs, cats, caged birds, aquarium fish, and what are known as test animals, for example hamsters, guinea pigs, rats and mice.

The control of these arthropods, helminths and/or protozoa should reduce cases of death and improve the performance (for meat, milk, wool, hides, eggs, honey etc.) and the health of the host animal, and so the use of the active compounds according to the invention enables more economically viable and easier animal husbandry.

For example, it is desirable to prevent or to interrupt the uptake of blood from the host by the parasites (if relevant). Control of the parasites can also contribute to preventing the transmission of infectious substances.

The term "control" as used herein with regard to the field of animal health means that the active compounds act by reducing the occurrence of the parasite in question in an animal infested with such parasites to a harmless level. More specifically, "control" as used herein means that the active compound kills the parasite in question, retards its growth or inhibits its proliferation.

In general, the active compounds according to the invention can be employed directly when they are used for the treatment of animals. They are preferably employed in the form of pharmaceutical compositions which may comprise pharmaceutically acceptable excipients and/or auxiliaries known in the prior art.

In the sector of animal health and in animal husbandry, the active compounds are employed (administered) in a known manner, by enteral administration in the form of, for example, tablets, capsules, potions, drenches, granules, pastes, boluses, the feed-through process and suppositories, by parenteral administration, for example by injection (intramuscular, subcutaneous, intravenous, intraperitoneal inter alia), implants, by nasal administration, by dermal administration in the form, for example, of dipping or bathing, spraying, pouring on and spotting on, washing and powdering, and also with the aid of moulded articles containing the active compound, such as collars, earmarks, tailmarks, limb bands, halters, marking devices, etc. The active compounds can be formulated as a shampoo or as suitable formulations applicable in aerosols or unpressurized sprays, for example pump sprays and atomizer sprays.

In the case of employment for livestock, poultry, domestic pets, etc., the active compounds according to the invention can be employed as formulations (for example powders, wettable powders ["WP"], emulsions, emulsifiable concentrates ["EC"], free-flowing compositions, homogeneous solutions and suspension concentrates ["SC"]), which contain the active compounds in an amount of 1 to 80% by weight, directly or after dilution (e.g. 100- to 10,000-fold dilution), or they can be used as a chemical bath.

In the case of use in the animal health sector, the active compounds according to the invention can be used in combination with suitable synergists or other active compounds, for example acaricides, insecticides, anthelmintics, anti-protozoal agents.

The compounds according to the invention can be prepared by customary methods known to those skilled in the art.

Reaction Scheme 1 shows the general Preparation Process A for the compounds (I-1) according to the invention.

Reaction Scheme 1

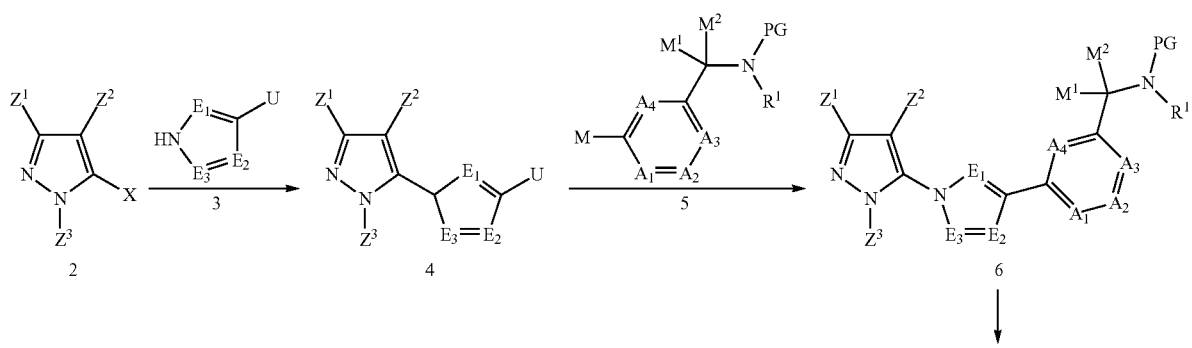

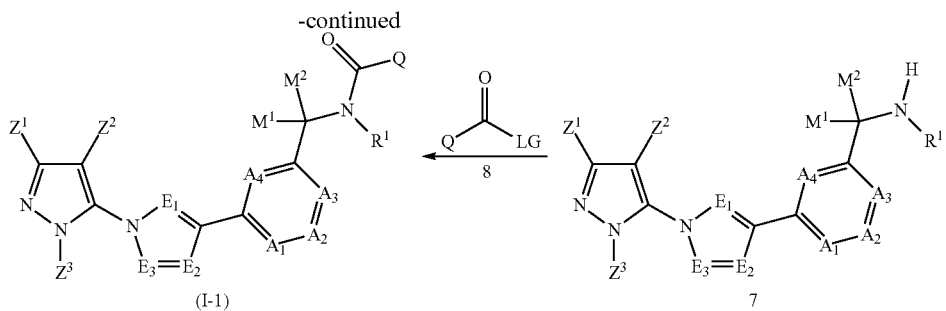

(I-1)

The radicals $A_1$-$A_4$, $R^1$, $M^1$, $M^2$, Q and $Z^1$-$Z^3$ have the meanings described above. PG represents a suitable protective group, e.g. t-butoxycarbonyl. LG represents a leaving group, e.g. chlorine. The five-membered cycles of E1-E3, carbon and nitrogen represent the 5-membered heterocycles defined under T. X represents a halogen, e.g. fluorine. U represents bromine, iodine or triflate if M represents a boronic acid, boronic ester or trifluoroboronate. U represents a boronic acid, boronic ester or trifluoroboronate if M represents bromine, iodine or triflate.

Compounds according to the invention of the general structure (I-1) can be prepared by processes known from the literature by reacting intermediate 7 with acylating agents of the general structure 8 [WO2010-051926; WO2010-133312]. Intermediates of the general structure 7 can be prepared from N-protected derivatives of the general structure 6. Compounds of the general structure 6 can be prepared by palladium-catalysed reactions from the reaction partners 4 and 5 [WO2005-040110; WO2009-089508]. The compounds of the general structure 5 are either commercially available or can be prepared by processes known to the person skilled in the art. The compounds of the general structure 4 can be prepared by processes known from the literature either by nucleophilic substitution at the aromatic ring (X=chlorine or fluorine) [WO2007-107470; Tetrahedron Letters 2003, 44, 7629-7632] or by a transition metal-catalysed reaction (X=bromine or iodine) [WO2012-003405; WO2009-158371] from the appropriate starting materials 2 and 3.

Alternatively, the compounds (I-1-1) according to the invention can be prepared by the general Preparation Process B (Reaction Scheme 2).

Reaction Scheme 2

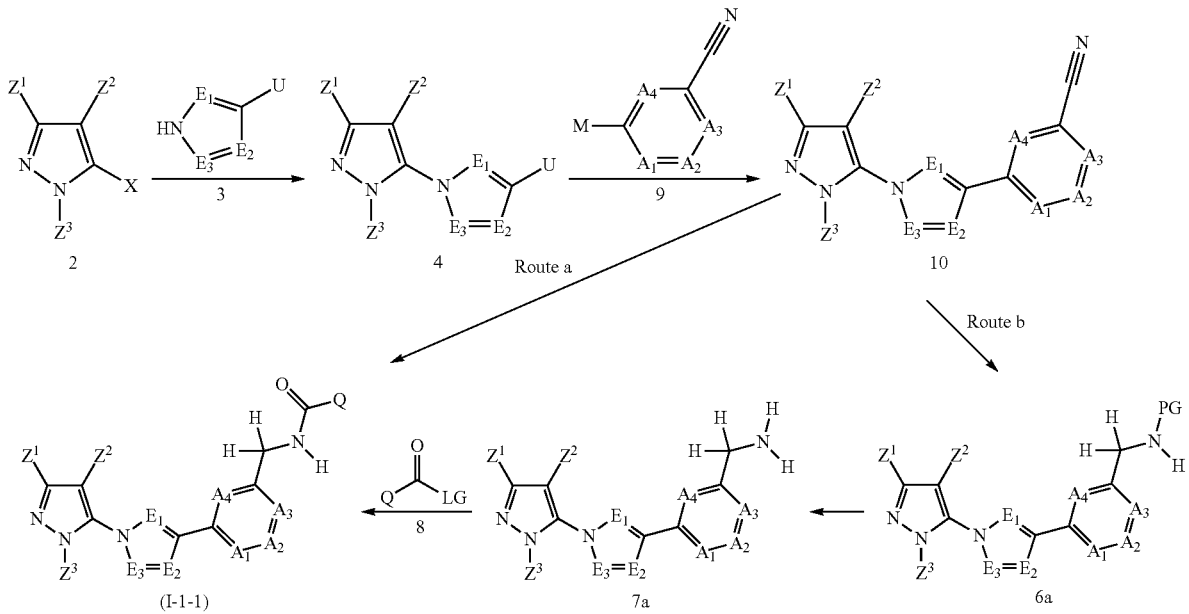

The radicals $A_1$-$A_4$, $R^1$, Q and $Z^1$-$Z^3$ have the meanings described above. PG represents a suitable protective group, e.g. t-butoxycarbonyl. LG represents a leaving group, e.g. chlorine. The five-membered cycles of E1-E3, carbon and nitrogen represent the 5-membered heterocycles defined under T. X represents a halogen, e.g. fluorine. U represents bromine, iodine or triflate if M represents a boronic acid, boronic ester or trifluoroboronate. U represents a boronic acid, boronic ester or trifluoroboronate if M represents bromine, iodine or triflate.

Compounds according to the invention of the general structure (I-1-1) can be prepared analogously to peptide coupling methods known from the literature from starting materials 8 and 7a [WO2010-051926; WO2010-133312]. Alternatively, the compounds according to the invention of the general structure (I-1-1) can also be prepared directly from compounds of the general structure 10 by processes known from the literature [Tetrahedron Letters 2000, 41(18), 3513-3516; Journal of the American Chemical Society 1925, 47, 3051-7]. Depending on the protective group used, compounds of the general structure 7a can be prepared by suitable deprotection of the amino function from compounds of the general structure 6a [Green's Protective Groups in Organic Synthesis, 4th Edition, P. G. M. Wuts, T. W. Greene, John Wiley & Sons, Inc., Hoboken, N.J., USA]. Compounds of the general structure 6a can be prepared analogously to processes known from the literature from compounds of the general structure 10 [Tetrahedron 2003, 59(29), 5417-5423; Journal of Medicinal Chemistry 2013, 56(5), 1946-1960]. Compounds of the general structure 10 can be prepared analogously to the above-described synthesis of 6. The preparation of the compounds of the general structure 4 has already been discussed in the Preparation Process.

Compounds according to the invention of the general structure (I-2) can be synthesized by the Preparation Process C shown in Reaction Scheme 3.

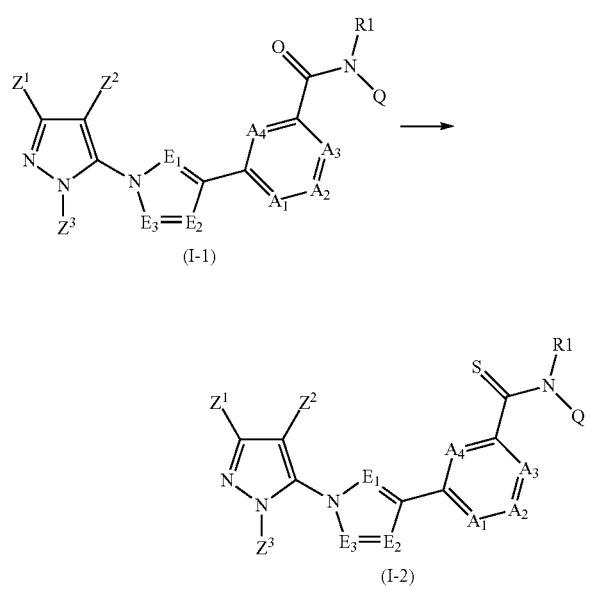

(I-1)

(I-2)

The radicals $A_1$-$A_4$, Q, $R^1$ and $Z^1$-$Z^3$ have the meanings described above. The five-membered cycles of E1-E3, carbon and nitrogen represent the 5-membered heterocycles defined under T.

Compounds according to the invention of the general structure (I-2) can be prepared analogously to processes known from the literature from compounds of the general structure (I-1) [WO2012-056372; WO2003-066050].

Compounds according to the invention of the general structure (II) can be synthesized by the Preparation Process D shown in Reaction Scheme 4.

Reaction Scheme 4

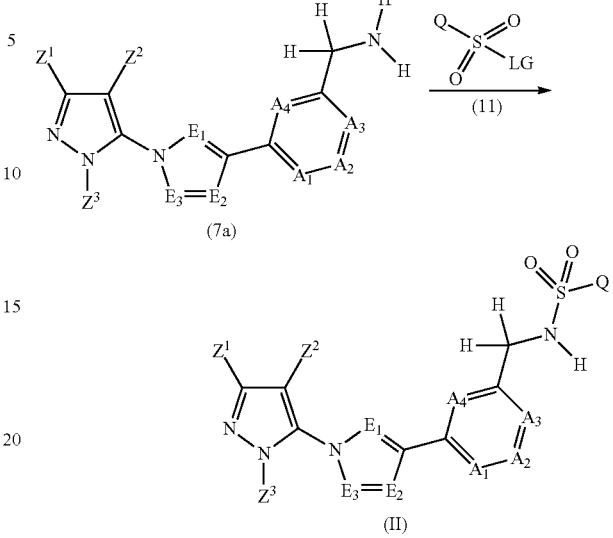

(7a)

(II)

The radicals $A_1$-$A_4$, $R^1$, Q and $Z^1$-$Z^3$ have the meanings described above. LG represents a leaving group, e.g. chlorine. The five-membered cycles of E1-E3, carbon and nitrogen represent the 5-membered heterocycles defined under T.

Compounds according to the invention of the general structure II can be prepared analogously to processes known from the literature from compounds of the general structure 7a and 11 [US2007/0117858; WO2013/068462; US2009/0233878]

The compounds of the general structure 5 are either commercially available or can be prepared by processes known to the person skilled in the art or analogously to these processes [WO2012004217; WO2009-130475; WO2008-107125; WO2003-099805; WO2012-0225061; WO2009-010488].

The compounds of the general structure 2 are either commercially available or can be prepared by processes known to the person skilled in the art or analogously to these processes [WO2010-051926; WO2011-131615; WO2006-018725; WO2012-065932; WO2007077961; US2012-0115903; WO2010-017902; WO2010-127856; Tetrahedron Letters 2011, 44, 8451-8457].

The compounds of the general structure 3 are either commercially available or can be prepared by processes known to the person skilled in the art or analogously to these processes.

Oxidizing agents for the oxidation of alcoholic groups are known (cf., for example, oxidizing agents in Organic Synthesis by Oxidation with Metal Compounds, Mijs, de Jonge, Plenum Verlag, New York, 1986; Manganese Compounds as Oxidizing Agents in Organic Chemistry, Arndt, Open Court Publishing Company, La Salle, Ill., 1981; The Oxidation of Organic Compounds by Permanganate Ion and Hexavalent Chromium, Lee, Open Court Publishing Company, La Salle, Ill., 1980). An oxidation can be carried out, for example, in the presence of permanganates (for example potassium permanganate), metal oxides (for example manganese dioxide, chromium oxides which are used, for example, in dipyridinechromium(VI) oxide as Collins reagent (cf. J. C. Collins et al., Tetrahedron Lett. 30, 3363-3366, 1968)). Likewise in the presence of pyridinium chlorochromate (for example Corey's reagent) (cf. also R. O. Hutchins et al., Tetrahedron Lett. 48, 4167-4170, 1977; D. Landini et al. Synthesis 134-136, 1979) or ruthenium tetroxide (cf. S.-I. Murahashi, N. Komiya Ruthenium-catalyzed Oxidation of Alkenes, Alcohols, Amines, Amides, β-Lactams, Phenols and Hydrocarbons, in: Modern Oxidation Methods, Baeckvall, Jan-Erling (Eds.), Wiley-VCH-Verlag GmbH & Co. KGaA, 2004). Likewise suitable are ultrasound-induced oxidation reactions and the use of potassium permanganate (cf. J. Yamawaki et al., Chem. Lett. 3, 379-380, 1983).

All known suitable acidic or basic reaction auxiliaries can be used according to the procedures described in the literature to deblock/remove the protective group SG. When protective groups of the carbamate type are used for amino groups, preference is given to using acidic reaction auxiliaries. When the t-butylcarbamate protective group (BOC group) is employed, for example, mixtures of mineral acids such as hydrochloric acid, hydrobromic acid, nitric acid, sulphuric acid, phosphoric acid or organic acids such as benzoic acid, formic acid, acetic acid, trifluoroacetic acid, methanesulphonic acid, benzenesulphonic acid or toluenesulphonic acid and a suitable diluent such as water and/or an organic solvent such as tetrahydrofuran, dioxane, dichloromethane, chloroform, ethyl acetate, ethanol or methanol are used. Preference is given to mixtures of hydrochloric acid or acetic acid with water and/or an organic solvent such as ethyl acetate.

It is known that certain reactions and preparation processes can be carried out particularly efficiently in the presence of diluents or solvents and basic or acidic reaction auxiliaries. It is also possible to use mixtures of the diluents or solvents. The diluents or solvents are advantageously employed in such an amount that the reaction mixture is readily stirrable during the entire process.

Suitable diluents or solvents for carrying out the processes according to the invention are, in principle, all organic solvents which are inert under the specific reaction conditions. Examples include: halohydrocarbons (for example chlorohydrocarbons such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloro ethane, chlorobenzene, bromobenzene, dichlorobenzene, chlorotoluene, trichlorobenzene), alcohols (for example methanol, ethanol, isopropanol, butanol), ethers (for example ethyl propyl ether, methyl tert-butyl ether, n-butyl ether, anisole, phenetole, cyclohexyl methyl ether, dimethyl ether, diethyl ether, dipropyl ether, diisopropyl ether, di-n-butyl ether, diisobutyl ether, diisoamyl ether, ethylene glycol dimethyl ether, tetrahydrofuran, dioxane, dichlorodiethyl ether and polyethers of ethylene oxide and/or propylene oxide), amines (for example trimethyl-, triethyl-, tripropyl-, tributylamine, N-methylmorpholine, pyridine and tetramethylenediamine), nitrohydrocarbons (for example nitromethane, nitroethane, nitropropane, nitrobenzene, chloronitrobenzene, o-nitrotoluene); nitriles (for example acetonitrile, propionitrile, butyronitrile, isobutyronitrile, benzonitrile, m-chlorobenzonitrile), tetrahydrothiophene dioxide, dimethyl sulphoxide, tetramethylene sulphoxide, dipropyl sulphoxide, benzyl methyl sulphoxide, diisobutyl sulphoxide, dibutyl sulphoxide, diisoamyl sulphoxide, sulphones (for example dimethyl, diethyl, dipropyl, dibutyl, diphenyl, dihexyl, methyl ethyl, ethyl propyl, ethyl isobutyl and pentamethylene sulphone), aliphatic, cycloaliphatic or aromatic hydrocarbons (for example pentane, hexane, heptane, octane, nonane and technical hydrocarbons), and also what are called "white spirits" with components having boiling points in the range from, for example, 40° C. to 250° C., cymene, petroleum fractions within a boiling range from 70° C. to 190° C., cyclohexane, methylcyclohexane, petroleum ether, ligroin, octane, benzene, toluene, chlorobenzene, bromobenzene, nitrobenzene, xylene, esters (for example methyl, ethyl, butyl and isobutyl acetate, dimethyl, dibutyl and ethylene carbonate); amides (for example hexamethylphosphoric triamide, formamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine, N,N'-diformylpiperazine) and ketones (for example acetone, acetophenone, methyl ethyl ketone, methyl butyl ketone).

The basic reaction auxiliaries used to perform the processes according to the invention may be all suitable acid binders. Examples include: alkaline earth metal or alkali metal compounds (e.g. hydroxides, hydrides, oxides and carbonates of lithium, sodium, potassium, magnesium, calcium and barium), amidine bases or guanidine bases (e.g. 7-methyl-1,5,7-triazabicyclo[4.4.0]dec-5-ene (MTBD); diazabicyclo[4.3.0]nonene (DBN), diazabicyclo[2.2.2]octane (DABCO), 1,8-diazabicyclo[5.4.0]undecene (DBU), cyclohexyltetrabutylguanidine (CyTBG), cyclohexyltetramethylguanidine (CyTMG), N,N,N,N-tetramethyl-1,8-naphthalenediamine, pentamethylpiperidine) and amines, especially tertiary amines (e.g. triethylamine, trimethylamine, tribenzylamine, triisopropylamine, tributylamine, tricyclohexylamine, triamylamine, trihexylamine, N,N-dimethylaniline, N,N-dimethyltoluidine, N,N-dimethyl-p-aminopyridine, N-methylpyrrolidine, N-methylpiperidine, N-methylimidazole, N-methylpyrazole, N-methylmorpholine, N-methylhexamethylenediamine, pyridine, 4-pyrrolidinopyridine, 4-dimethylaminopyridine, quinoline, α-picoline, β-picoline, isoquinoline, pyrimidine, acridine, N,N,N', N'-tetramethylenediamine, N,N,N',N'-tetraethylenediamine, quinoxaline, N-propyldiisopropylamine, N-ethyldiisopropylamine, N,N'-dimethylcyclohexylamine, 2,6-lutidine, 2,4-lutidine or triethyldiamine).

The acidic reaction auxiliaries used to perform the processes according to the invention include all mineral acids (e.g. hydrohalic acids such as hydrofluoric acid, hydrochloric acid, hydrobromic acid or hydriodic acid, and also sulphuric acid, phosphoric acid, phosphorous acid, nitric acid), Lewis acids (e.g. aluminium(III) chloride, boron trifluoride or its etherate, titanium(IV) chloride, tin(IV) chloride) and organic acids (e.g. formic acid, acetic acid, propionic acid, malonic acid, lactic acid, oxalic acid, fumaric acid, adipic acid, stearic acid, tartaric acid, oleic acid, methanesulphonic acid, benzoic acid, benzenesulphonic acid or para-toluenesulphonic acid).

If protective groups are intended in the reaction schemes, all generally known protective groups may be used. In particular those described by Greene T. W., Wuts P. G. W. in Protective Groups in Organic Synthesis; John Wiley & Sons, Inc. 1999, "Protection for the hydroxyl group including 1,2- and 1,3-diols".

Also suitable are protective groups
of the substituted methyl ether type (for example methoxymethyl ether (MOM), methylthiomethyl ether (MTM), (phenyldimethylsilyl)methoxymethyl ether (SNOM-OR), benzyloxymethyl ether (BOM-OR) para-methoxybenzyloxymethyl ether (PMBM-OR), para-nitrobenzyloxymethyl ether (NBOM-OR), ortho-nitrobenzyloxymethyl ether (NBOM-OR), (4-methoxyphenoxy)methyl ether (p-AOM-OR), guaiacolmethyl ether (GUM-OR), t-butoxymethyl ether, 4-pentyloxymethyl ether (POM-OR), syliloxymethyl ether, 2-methoxyethoxymethyl ether (MEM-OR), 2,2,2-trichloroethoxymethyl ether, bis(2-chloroethoxy) methyl ether, 2-(trimethylsilyl)ethoxymethyl ether (SEM-OR), methoxymethyl ether (MM-OR));

of the substituted ethyl ether type (for example 1-ethoxyethyl ether (EE-OR), 1-(2-chloroethoxy)ethyl ether (CEE-OR), 1-[2-(trimethylsilyl)ethoxy]ethyl ether (SEE-OR), 1-methyl-1-methoxyethyl ether (MIP-OR), 1-methyl-1-benzyloxyethyl ether (MBE-OR), 1-methyl-1-benzyloxy-2-fluorpethyl ether (MIP-OR), 1-methyl-1-phenoxyethyl ether, 2,2,2-trichloroethyl ether, 1,1-dianisyl-2,2,2-trichloroethyl ether (DATE-OR), 1,1,1,3,3,3-hexafluoro-2-phenylisopropyl ether (HIP-OR), 2-trimethylsilylethyl ether, 2-(benzylthio)ethyl ether, 2-(phenylselenyl)ethyl ether), an ether (for example tetrahydropyranyl ether (THP-OR), 3-bromotetrahydropyranyl ether (3-BrTHP-OR), tetrahydrothiopyranyl ether, 1-methoxycyclohexyl ether, 2- and 4-picolyl ether, 3-methyl-2-picolyl-N-oxido ether, 2-quinolinylmethyl ether (Qm-OR), 1-pyrenylmethyl ether, diphenylmethyl ether (DPM-OR), para, para'-dinitrobenzhydryl ether (DNB-OR), 5-dibenzosuberyl ether, triphenylmethyl ether (Tr-OR), alpha-naphthyldiphenylmethyl ether, para-methoxyphenyldiphenylmethyl ether (MMTrOR), di(para-methoxyphenyl)phenylmethyl ether (DMTr-OR), tri(para-methoxyphenyl)phenylmethyl ether (TMTr-OR), 4-(4'-bromophenacyloxy)phenyldiphenylmethyl ether, 4,4',4"-tris (4,5-dichlorophthalimidophenyl)methyl ether (CPTr-OR), 4,4',4"-tris(benzoyloxyphenyl)methyl ether (TBTr-OR), 4,4'-dimethoxy-3"-[N-(imidazolylmethyl)]trityl ether (IDTr-OR), 4,4'-dimethoxy-3"-[N-(imidazolylethyl)carbamoyl]trityl ether (IETr-OR), 1,1-bis(4-methoxyphenyl)-1'-pyrenylmethyl ether (Bmpm-OR), 9-anthryl ether, 9-(9-phenyl)xanthenyl ether (Pixyl-OR), 9-(9-phenyl-10-oxo) anthryl (tritylone ether), 4-methoxytetrahydropyranyl ether (MTHP-OR), 4-methoxytetrahydrothiopyranyl ether, 4-methoxytetrahydrothiopyranyl S,S-dioxide, 1-[(2-chloro-4-methyl)phenyl]-4-methoxypiperidin-4-yl ether (CTMP-OR), 1-(2-fluorophenyl)-4-methoxypiperidin-4-yl ether (Fpmp-OR), 1,4-dioxan-2-yl ether, tetrahydrofuranyl ether, tetrahydrothiofuranyl ether, 2,3,3a,4,5,6,7,7a-octahydro-7,8, 8-trimethyl-4,7-methanebenzofuran-2-yl ether (MBF-OR), t-butyl ether, allyl ether, propargyl ether, para-chlorophenyl ether, para-methoxyphenyl ether, para-nitrophenyl ether, para-2,4-dinitrophenyl ether (DNP-OR), 2,3,5,6-tetrafluoro-4-(trifluoromethyl)phenyl ether, benzyl ether (Bn-OR));

of the substituted benzyl ether type (for example para-methoxybenzyl ether (MPM-OR), 3,4-dimethoxybenzyl ether (DMPM-OR), ortho-nitrobenzyl ether, para-nitrobenzyl ether, para-halobenzyl ether, 2,6-dichlorobenzyl ether, para-aminoacylbenzyl ether (PAB-OR), para-azidobenzyl ether (Azb-OR), 4-azido-3-chlorobenzyl ether, 2-trifluoromethylbenzyl ether, para-(methylsulphinyl)benzyl ether (Msib-OR));

of the silyl ether type (for example trimethylsilyl ether (TMS-OR), triethylsilyl ether (TES-OR), triisopropylsilyl ether (TIPS-OR), dimethylisopropylsilyl ether (IPDMS-OR), diethylisopropylsilyl ether (DEIPS-OR), dimethylhexylsilyl ether (TDS-OR), t-butyldimethylsilyl ether (TBDMS-OR), t-butyldiphenylsilyl ether (TBDPS-OR), tribenzylsilyl ether, tri-para-xylylsilyl ether, triphenylsilyl ether (TPS-OR), diphenylmethylsilyl ether (DPMS-OR), di-t-butylmethylsilyl ether (DTBMS-OR), tris(trimethylsilyl)silyl ether (sisyl ether), di-t-butylmethylsilyl ether (DTBMS-OR), tris(trimethylsilyl)silyl ether (sisyl ether), (2-hydroxystyryl)dimethylsilyl ether (HSDMS-OR), (2-hydroxystyryl)diisopropylsilyl ether (HSDIS-OR), t-butylmethoxyphenylsilyl ether (TBMPS-OR), t-butoxydiphenylsilyl ether (DPTBOS-OR));

of the ester type (for example formate ester, benzoylformate ester, acetate ester (Ac-OR), chloroacetate ester, dichloroacetate ester, trichloroacetate ester, trifluoroacetate ester (TFA-OR), methoxyacetate ester, triphenylmethoxyacetate ester, phenoxyacetate ester, para-chlorophenoxyacetate ester, phenylacetate ester, diphenylacetate ester (DPA-OR), nicotinate ester, 3-phenylpropionate ester, 4-pentoate ester, 4-oxopentoate ester (levulinate) (Lev-OR), 4,4-(ethylenedithio)pentanoate ester (LevS-OR), 5-[3-bis(4-methoxyphenyl)hydroxymethoxyphenoxy]levulinate ester, pivaloate ester (Pv-OR), 1-adamantanoate ester, crotonate ester, 4-methoxycrotonate ester, benzoate ester (Bz-OR), para-phenylbenzoate ester, 2,4,6-trimethylbenzoate ester (mesitoate), 4-(methylthiomethoxy)butyrate ester (MTMB-OR), 2-(methylthiomethoxymethyl)benzoate ester (MTMT-OR), of the ester type (for example methyl carbonate, methoxymethyl carbonate, 9-fluorenylmethyl carbonate (Fmoc-OR), ethyl carbonate, 2,2,2-trichloroethyl carbonate (Troc-OR), 1,1-dimethyl-2,2,2-trichloroethyl carbonate (TCBOC-OR), 2-(trimethylsilyl)ethyl carbonate (TMS-OR), 2-(phenylsulphonyl)ethyl carbonate (Ps-OR), 2-(triphenylphosphonio)ethyl carbonate (Peoc-OR), t-butyl carbonate (Boc-OR), isobutyl carbonate, vinyl carbonate, allyl carbonate (Alloc-OR), para-nitrophenyl carbonate, benzyl carbonate (Z-OR), para-methoxybenzyl carbonate, 3,4-dimethoxybenzyl carbonate, ortho-nitrobenzyl carbonate, para-nitrobenzyl carbonate, 2-dansylethyl carbonate (Dnseoc-OR), 2-(4-nitrophenyl)ethyl carbonate (Npeoc-OR), 2-(2,4-dinitrophenyl)ethyl carbonate (Dnpeoc)), and of the sulphate type (for example allylsulphonate (Als-OR), methanesulphonate (Ms-OR), benzylsulphonate, tosylate (Ts-OR), 2-[(4-nitrophenyl)ethyl]sulphonate (Npes-OR)).

Suitable catalysts for carrying out a catalytic hydrogenation in the process according to the invention are all customary hydrogenation catalysts such as, for example, platinum catalysts (for example platinum plate, platinum sponge, platinum black, colloidal platinum, platinum oxide, platinum wire), palladium catalysts (for example palladium sponge, palladium black, palladium oxide, palladium/carbon, colloidal palladium, palladium/barium sulphate, palladium/barium carbonate, palladium hydroxide), nickel catalysts (for example reduced nickel, nickel oxide, Raney nickel), ruthenium catalysts, cobalt catalysts (for example reduced cobalt, Raney cobalt), copper catalysts (for example reduced copper, Raney copper, Ullmann copper). Preference is given to using noble metal catalysts (for example platinum and palladium or ruthenium catalysts), which may be applied to a suitable support (for example carbon or silicon), rhodium catalysts (for example tris(triphenylphosphine)rhodium(I) chloride in the presence of triphenylphosphine). Furthermore, it is possible to use "chiral hydrogenation catalysts" (for example those comprising chiral diphosphine ligands such as (2S,3S)-(−)-2,3-bis(diphenylphosphino)butane[(S,S)-chiraphos] or (R)-(+)-2,2'- or (S)-(−)-2,2'-bis(diphenylphosphino)-1,1'-binaphthalene [R(+)-BINAP or S(−)-BINAP]), whereby the proportion of an isomer in the isomer mixture is increased or the formation of another isomer is virtually completely suppressed.

Salts of the compounds according to the invention are prepared by standard methods. Representative acid addition salts are, for example, those formed by reaction with inorganic acids, such as, for example, sulphuric acid, hydrochloric acid, hydrobromic acid, phosphoric acid, or organic carboxylic acids such as acetic acid, trifluoroacetic acid, citric acid, succinic acid, butyric acid, lactic acid, formic acid, fumaric acid, maleic acid, malonic acid, camphoric acid, oxalic acid, phthalic acid, propionic acid, glycolic acid, glutaric acid, stearic acid, salicylic acid, sorbic acid, tartaric acid, cinnamic acid, valeric acid, picric acid, benzoic acid or organic sulphonic acids such as methanesulphonic acid and 4-toluenesulphonic acid.

Also representative are salts of compounds according to the invention formed from organic bases such as, for example, pyridine or triethylamine, or those formed from inorganic bases such as, for example, hydrides, hydroxides or carbonates of sodium, lithium, calcium, magnesium or barium, provided the compounds of the general formula (I) have a structural element suitable for this salt formation.

Synthesis methods for preparing heterocyclic N-oxides and t-amines are known. They can be obtained using peroxy acids (for example peracetic acid and meta-chloroperbenzoic acid (MCPBA), hydrogen peroxide), alkyl hydroperoxides (for example t-butyl hydroperoxide), sodium perborate and dioxiranes (for example dimethyldioxirane). These methods have been described, for example, by T. L. Gilchrist, in Comprehensive Organic Synthesis, Vol. 7, pp. 748-750, 1992, S. V. Ley, (Ed.), Pergamon Press; M. Tisler, B. Stanovnik, in Comprehensive Heterocyclic Chemistry, Vol. 3, pp. 18-20, 1984, A. J. Boulton, A. McKillop, (Eds.), Pergamon Press; M. R. Grimmett, B. R. T. Keene in Advances in Heterocyclic Chemistry, Vol. 43, pp. 149-163, 1988, A. R. Katritzky, (Ed.), Academic Press; M. Tisler, B. Stanovnik, in Advances in Heterocyclic Chemistry, Vol. 9, pp. 285-291, 1968, A. R. Katritzky, A. J. Boulton (Eds.), Academic Press; G. W. H. Cheeseman, E. S. G. Werstiuk in Advances in Heterocyclic Chemistry, Vol. 22, pp. 390-392, 1978, A. R. Katritzky, A. J. Boulton, (Eds.), Academic Press.

EXPERIMENTAL PART

Preparation Process A

Preparation of N-{2-fluoro-5-[5'-(pentafluoroethyl)-4'-(trifluoromethyl)-2'H-1,3'-bipyrazol-4-yl]benzyl}propanamide (Example Ic-1) and tert-butyl {3-[2'-methyl-5'-(pentafluoroethyl)-4'-(trifluoromethyl)-2'H-1,3'-bipyrazol-4-yl]benzyl}carbamate (Example Ic-18)

Reaction Scheme 5 shows the synthesis of the compounds (Ic-18) and (Ic-1) according to the invention.

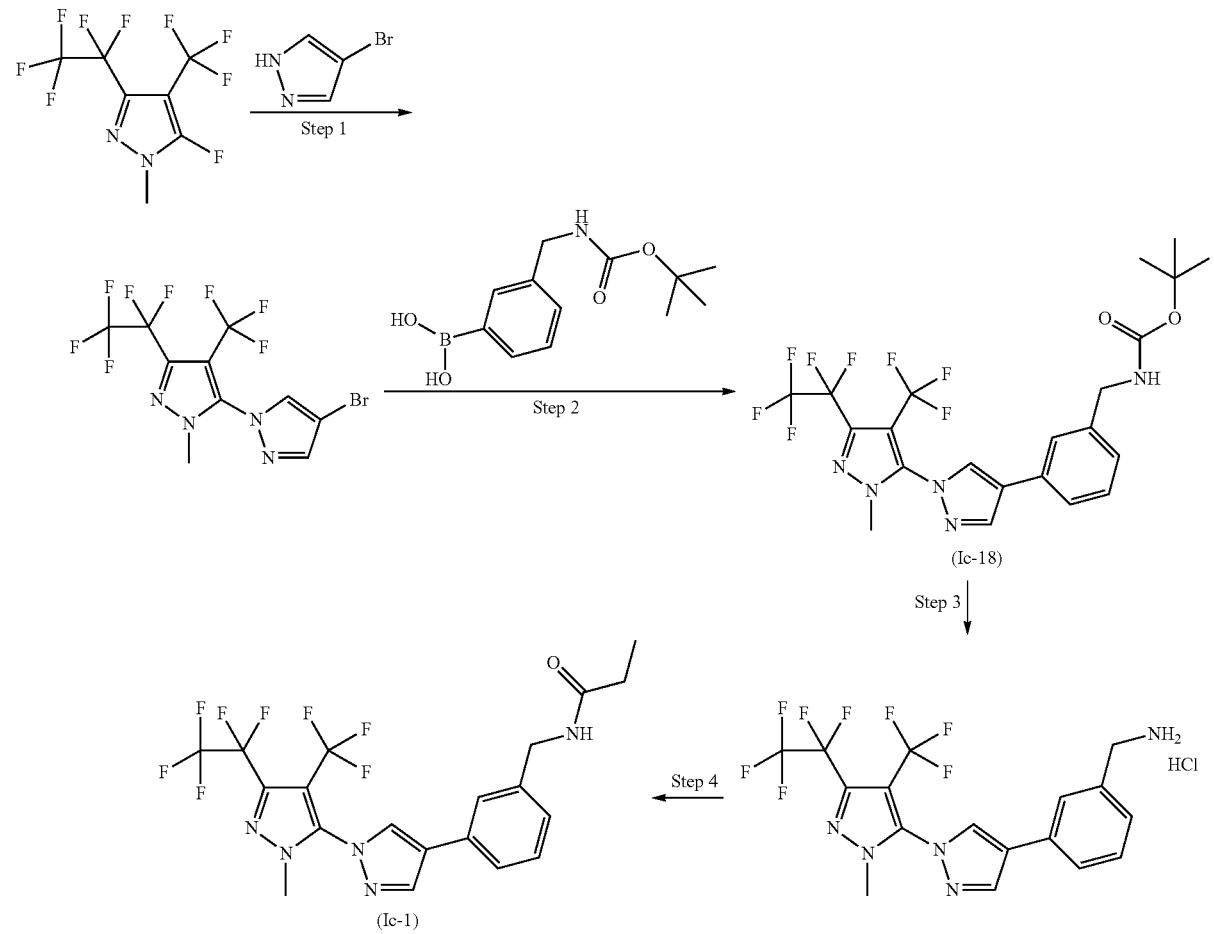

Reaction Scheme 5

Step 1: Synthesis of 4-bromo-2'-methyl-5'-(pentafluoroethyl)-4'-(trifluoromethyl)-2'H-1,3'-bipyrazole 16.0 g (55.9 mmol) of 5-fluoro-1-methyl-3-(pentafluoroethyl)-4-(trifluoromethyl)-1H-pyrazole, 8.22 g (55.9 mmol)

of 4-bromo-1H-pyrazole and 15.5 g (112 mmol) of potassium carbonate are suspended in 250 ml of tetrahydrofuran. The reaction mixture is heated under reflux for 16 h. The solid reaction components are filtered off and washed with tetrahydrofuran. The combined organic phases are concentrated under reduced pressure on a rotary evaporator.

This gives 23.0 g of 4-bromo-2'-methyl-5'-(pentafluoroethyl)-4'-(trifluoromethyl)-2'H-1,3'-bipyrazole $^1$H-NMR (400 MHz, d$_6$-DMSO): δ=8.58 (s, 1H); 8.16 (s, 1H); 3.32 (s, 3H);

HPLC-MS: log P$^{a)}$=4.17

Step 2: Synthesis of tert-butyl {3-[2'-methyl-5'-(pentafluoroethyl)-4'-(trifluoromethyl)-2'H-1,3'-bipyrazol-4-yl]benzyl}carbamate (Ic-18)

500 mg (1.21 mmol) of 4-bromo-2'-methyl-5'-(pentafluoroethyl)-4'-(trifluoromethyl)-2'H-1,3'-bipyrazole, 304 mg (1.21 mmol) of (3-{[(tert-butoxycarbonyl)amino]methyl}phenyl)boronic acid and 69.9 mg (0.06 mmol) of tetrakis(triphenylphosphine)palladium(0) are dissolved in a mixture of 10 ml of 2-propanol and 3.69 ml of 1N sodium bicarbonate solution. The solutions were thoroughly degassed beforehand. Under an atmosphere of protective gas, the reaction mixture is heated at 90° C. for 16 h. The reaction mixture is diluted with water and extracted repeatedly with chloroform. The combined organic phases are dried over sodium sulphate, filtered and concentrated on a rotary evaporator under reduced pressure. The crude product is purified on an RP phase.

This gives 410 mg of tert-butyl {3-[2'-methyl-5'-(pentafluoroethyl)-4'-(trifluoromethyl)-2'H-1,3'-bipyrazol-4-yl]benzyl}carbamate (Ic-18)

$^1$H-NMR (400 MHz, d$_6$-DMSO): δ=8.68 (s, 1H); 8.44 (s, 1H); 7.64-7.19 (5H, m); 4.19 (m, 2H); 3.82 (s, 3H); 1.40 (s, 9H)

HPLC-MS: log P$^{a)}$=4.74; mass (m/z)=540.1 [M+H]$^+$.

Step 3: Synthesis of 1-{3-[2'-methyl-5'-(pentafluoroethyl)-4'-(trifluoromethyl)-2'H-1,3'-bipyrazol-4-yl]phenyl}methanamine hydrochloride (1:1)

400 mg (0.74 mmol) of tert-butyl {3-[2'-methyl-5'-(pentafluoroethyl)-4'-(trifluoromethyl)-2'H-1,3'-bipyrazol-4-yl]benzyl}carbamate are dissolved in 5 ml of 4N hydrogen chloride in dioxane, and the mixture is stirred for 1 h. The solvent is removed on a rotary evaporator under reduced pressure.

This gives 410 mg of 1-{3-[2'-methyl-5'-(pentafluoroethyl)-4'-(trifluoromethyl)-2'H-1,3'-bipyrazol-4-yl]phenyl}methanamine hydrochloride (1:1)

$^1$H-NMR (400 MHz, d$_6$-DMSO): δ=8.71 (s, 1H); 8.48 (s, 1H); 7.87-7.42 (m, 4H)

HPLC-MS: log P$^{a)}$=1.93, mass (m/z)=440.1 [M+H]$^+$.

Step 4: Synthesis of N-{3-[2'-methyl-5'-(pentafluoroethyl)-4'-(trifluoromethyl)-2'H-1,3'-bipyrazol-4-yl]benzyl}propanamide (Ic-1)

133 mg (0.32 mmol) of 1-{3-[2'-methyl-5'-(pentafluoroethyl)-4'-(trifluoromethyl)-2'H-1,3'-bipyrazol-4-yl]phenyl}methanamine and 0.13 ml of N,N-diethyl-N-isopropylamine are dissolved in 3 ml of chloroform, and 29 μl (0.35 mmol) of propionyl chloride are then added. After one hour, 5% strength sodium hydrogen phosphate solution is added to the reaction mixture. The aqueous phase is extracted repeatedly with chloroform. The combined organic phases are dried over sodium sulphate, filtered and concentrated under reduced pressure on a rotary evaporator. The crude product is purified by column chromatography on silica gel.

This gives 40 mg of N-{3-[2'-methyl-5'-(pentafluoroethyl)-4'-(trifluoromethyl)-2'H-1,3'-bipyrazol-4-yl]benzyl}propanamide (Ic-1)

$^1$H-NMR see NMR data in peak list

HPLC-MS: log P$^{a)}$=3.59, mass (m/z)=496.1 [M+H]$^+$.

Preparation of N-(3-{1-[1-methyl-3-(pentafluoroethyl)-4-(trifluoromethyl)-1H-pyrazol-5-yl]-1H-imidazol-4-yl}benzyl)propanamide (Ib-5) and tert-butyl (3-{1-[1-methyl-3-(pentafluoroethyl)-4-(trifluoromethyl)-1H-pyrazol-5-yl]-1H-imidazol-4-yl}benzyl)carbamate (Ib-1)

Reaction Scheme 6 shows the synthesis of the compounds (Ib-5) and (Ib-1) according to the invention.

Reaction Scheme 6

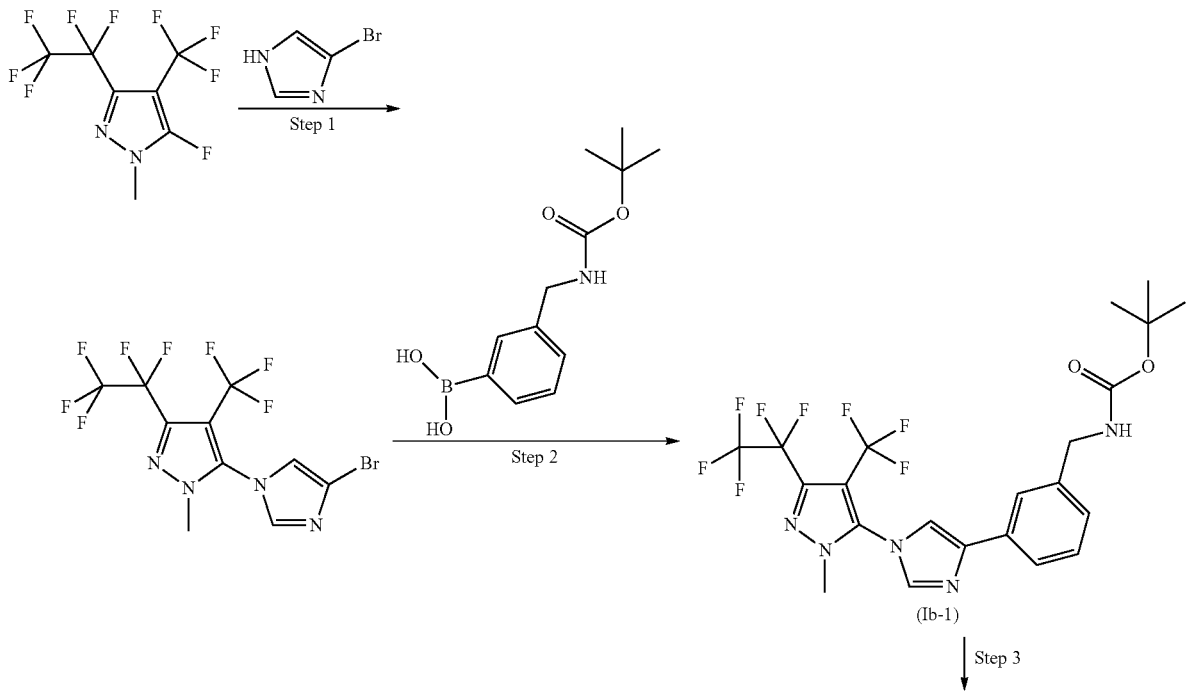

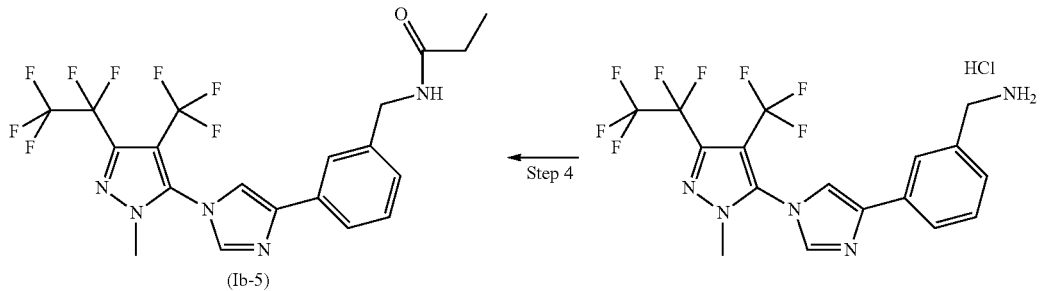

Step 1: Synthesis of 5-(4-iodo-1H-imidazol-1-yl)-1-methyl-3-(pentafluoroethyl)-4-(trifluoromethyl)-1H-pyrazole 7.0 g (24.5 mmol) of 5-fluoro-1-methyl-3-(pentafluoroethyl)-4-(trifluoromethyl)-1H-pyrazole, 4.75 g (24.5 mmol) of 4-iodo-1H-imidazole and 6.76 g (48.9 mmol) of potassium carbonate are suspended in 100 ml of tetrahydrofuran. The reaction mixture is heated under reflux for 16 h. The solid components are filtered off and washed with tetrahydrofuran. The solvent is removed under reduced pressure on a rotary evaporator. The crude product is purified by column chromatography on silica gel. This gives 8.73 g of 5-(4-iodo-1H-imidazol-1-yl)-1-methyl-3-(pentafluoroethyl)-4-(trifluoromethyl)-1H-pyrazole.

$^1$H-NMR (400 MHz, d$_6$-DMSO): δ=8.073 (s, 1H); 7.86 (s, 1H); 3.73 (s, 3H);

HPLC-MS: log P$^{a)}$=3.47, mass (m/z)=460.8; 461.8 [M+H]$^+$.

Step 2: Synthesis of tert-butyl (3-{1-[1-methyl-3-(pentafluoroethyl)-4-(trifluoromethyl)-1H-pyrazol-5-yl]-1H-imidazol-4-yl}benzyl)carbamate (Ib-1)

2.00 g (4.35 mmol) of 5-(4-iodo-1H-imidazol-1-yl)-1-methyl-3-(pentafluoroethyl)-4-(trifluoromethyl)-1H-pyrazole, 1.09 g (4.35 mmol) of (3-{[(tert-butoxycarbonyl)amino]methyl}phenyl)boronic acid and 251 mg (0.22 mmol) of tetrakis(triphenylphosphine)palladium(0) are dissolved in a mixture of 40 ml of 2-propanol and 13 ml of 1N aqueous sodium bicarbonate solution. The solvents were thoroughly degassed beforehand. Under an atmosphere of protective gas, the reaction solution is heated at 90° C. for 16 h. After the reaction has ended, water and chloroform are added to the reaction mixture. The organic phase is extracted with chloroform. The combined organic phases are then concentrated under reduced pressure on a rotary evaporator. The crude product is then purified on an RP phase. This gives 1.43 g of tert-butyl (3-{1-[1-methyl-3-(pentafluoroethyl)-4-(trifluoromethyl)-1H-pyrazol-5-yl]-1H-imidazol-4-yl}benzyl)carbamate (Ib-1)

$^1$H-NMR (400 MHz, d$_6$-DMSO): δ=8.17 (s, 1H); 8.06 (s, 1H); 7.72 (s, 1H); 7.65 (d, 1H); 7.55 (t, 1H); 7.45 (t, 1H); 7.25 (d, 1H); 4.17 (d, 2H); 3.78 (s, 3H); 1.40 (s, 9H)

HPLC-MS: log P$^{a)}$=4.21; mass (m/z)=540.1 [M+H]$^+$.

Step 3: Synthesis of 1-(3-{1-[1-methyl-3-(pentafluoroethyl)-4-(trifluoromethyl)-1H-pyrazol-5-yl]-1H-imidazol-4-yl}phenyl)methanamine hydrochloride 600 mg (1.11 mmol) of tert-butyl (3-{1-[1-methyl-3-(pentafluoroethyl)-4-(trifluoromethyl)-1H-pyrazol-5-yl]-1H-imidazol-4-yl}benzyl)carbamate are dissolved in 8.34 ml of 4N hydrogen chloride in dioxane, and the mixture is stirred for 1 h. The solvent is removed on a rotary evaporator under reduced pressure. This gives 650 mg of crude product which is used without further purification in the subsequent reactions.

HPLC-MS: log P$^{a)}$=1.83, mass (m/z)=440.1 [M+H-HCl]$^+$.

Step 4: Synthesis of N-(3-{1-[1-methyl-3-(pentafluoroethyl)-4-(trifluoromethyl)-1H-pyrazol-5-yl]-1H-imidazol-4-yl}benzyl)propanamide (Ib-5)

216 mg (0.45 mmol) of 1-(3-{1-[1-methyl-3-(pentafluoroethyl)-4-(trifluoromethyl)-1H-pyrazol-5-yl]-1H-imidazol-4-yl}phenyl)methanamine hydrochloride and 190 μl (1.1 mmol) of N,N-diethyl-N-isopropylamine are dissolved in chloroform, and 46 mg (0.5 mmol) of propionyl chloride are then added. A catalytic amount of 4-(dimethylamino)pyridine is added. After one hour, 5% strength sodium hydrogen phosphate solution is added to the reaction mixture. The aqueous phase is extracted repeatedly with chloroform. The combined organic phases are dried over sodium sulphate, filtered and concentrated under reduced pressure on a rotary evaporator. The crude product is purified by column chromatography on silica gel.

This gives 70 mg of N-(3-{1-[1-methyl-3-(pentafluoroethyl)-4-(trifluoromethyl)-1H-pyrazol-5-yl]-1H-imidazol-4-yl}benzyl)propanamide (Ib-5)

$^1$H-NMR see NMR data in peak list

HPLC-MS: log P$^{a)}$=3.14, mass (m/z)=496.1 [M+H]$^+$.

Preparation Process B

Preparation of N-{2-fluoro-5-[2'-methyl-5'-(pentafluoroethyl)-4'-(trifluoromethyl)-2'H-1,3'-bipyrazol-4-yl]benzyl}propanamide (Ib-8)

Reaction Scheme 7 shows the synthesis of the compound (Ib-8) according to the invention.

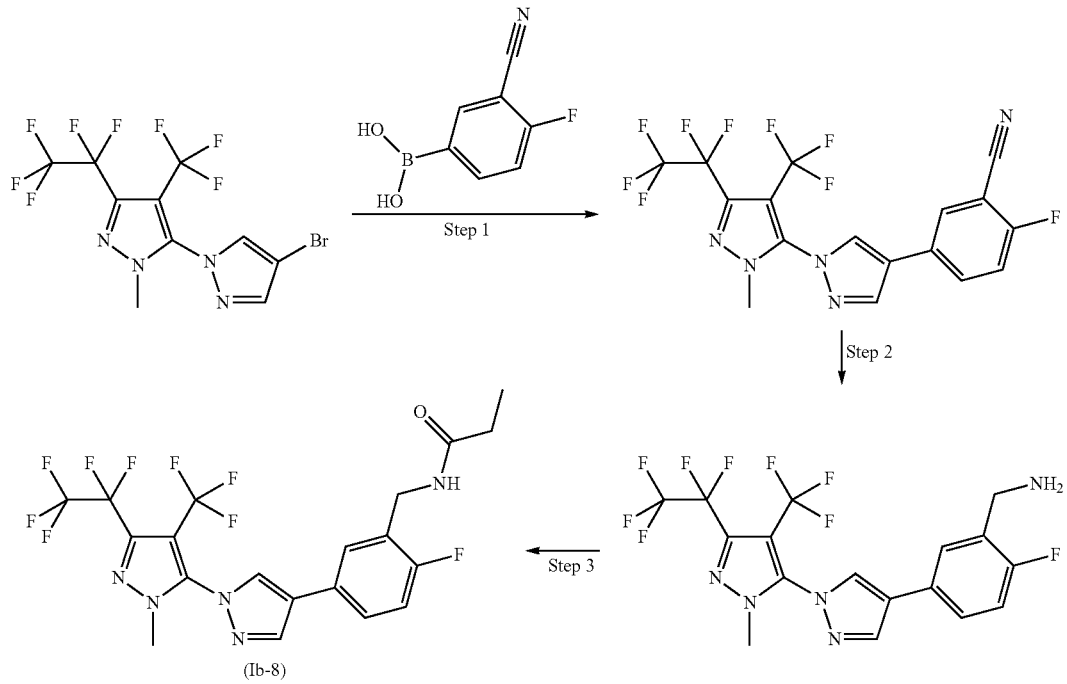

Reaction Scheme 7

Step 1: Synthesis of 2-fluoro-5-[2'-methyl-5'-(pentafluoroethyl)-4'-(trifluoromethyl)-2'H-1,3'-bipyrazol-4-yl]benzonitrile 4.00 g (10 mmol) of 4-bromo-2'-methyl-5'-(pentafluoroethyl)-4'-(trifluoromethyl)-2'H-1,3'-bipyrazole, 1.60 g (10 mmol) of (3-cyano-4-fluorophenyl)boronic acid and 0.56 g (0.2 mmol) of tetrakis(triphenylphosphine)palladium(0) are dissolved in a mixture of 80 ml of 2-propanol and 30 ml of 1N aqueous sodium bicarbonate solution. The solvents were thoroughly degassed beforehand. Under an atmosphere of protective gas, the reaction solution is heated at 85° C. for 5 h. After the reaction has ended, water and chloroform are added to the reaction mixture. The organic phase is extracted with chloroform. The combined organic phases are then concentrated under reduced pressure on a rotary evaporator. The crude product is then purified on an RP phase.

This gives 3.31 g of 2-fluoro-5-[2'-methyl-5'-(pentafluoroethyl)-4'-(trifluoromethyl)-2'H-1,3'-bipyrazol-4-yl]benzonitrile.

$^1$H-NMR (400 MHz, $d_6$-DMSO): δ=8.83 (s, 1H); 8.60 (s, 1H); 8.37 (dd, 1H); 8.14-8.12 (m, 1H); 7.67-7.61 (m, 1H); 3.83 (s, 3H)

HPLC-MS: log $P^{a)}$=4.37, mass (m/z)=454.0 [M+H]$^+$.

Step 2: Synthesis of 1-{2-fluoro-5-[5'-(pentafluoroethyl)-4'-(trifluoromethyl)-2'H-1,3'-bipyrazol-4-yl]phenyl}methanamine 4.60 g (10 mmol) of 2-fluoro-5-[2'-methyl-5'-(pentafluoroethyl)-4'-(trifluoromethyl)-2'H-1,3'-bipyrazol-4-yl]benzonitrile are dissolved in 120 ml of methanol. The solution is cooled to 0° C., and 13 mg (0.1 mmol) of nickel(II) chloride×6H$_2$O are then added. In small portions, 768 mg (20 mmol) of sodium borohydride are added to the mixture. After the last addition, the reaction mixture is slowly warmed to room temperature. After 1 h at room temperature, another 4 mg (0.03 mmol) of nickel(II) chloride×6H$_2$O and 220 mg (5.7 mmol) pf sodium borohydride are added to the reaction mixture. The reaction mixture is stirred at room temperature for a further hour. The reaction mixture is then diluted with water. The mixture is extracted three times with chloroform. The combined organic phases are dried over sodium sulphate, filtered and then concentrated under reduced pressure on a rotary evaporator. The residue is purified on an RP phase.

This gives 1.25 g of 1-{2-fluoro-5-[5'-(pentafluoroethyl)-4'-(trifluoromethyl)-2'H-1,3'-bipyrazol-4-yl]phenyl}methanamine.

$^1$H-NMR (400 MHz, $d_6$-DMSO): δ=8.68 (s, 1H); 8.45 (s, 1H); 7.83 (dd, 1H); 7.60-7.56 (m, 1H); 7.20 (t, 1H); 3.82 (s, 3H); 3.78 (s, 2H); 1.83 (s, 2H)

HPLC-MS: log $P^{a)}$=1.90, mass (m/z)=458.0 [M+H-HCl]$^+$.

Step 3: Synthesis of N-{2-fluoro-5-[5'-(pentafluoroethyl)-4'-(trifluoromethyl)-2'H-1,3'-bipyrazol-4-yl]benzyl}propanamide (Ib-8)

250 mg (0.55 mmol) of 1-{2-fluoro-5-[5'-(pentafluoroethyl)-4'-(trifluoromethyl)-2'H-1,3'-bipyrazol-4-yl]phenyl}methanamine and 0.23 ml (1.31 mmol) of N,N-diethyl-N-isopropylamine are dissolved in 3 ml of chloroform, and 52 μl (0.61 mmol) of propionyl chloride are added. After one hour, 5% strength sodium hydrogen phosphate solution is added to the reaction mixture. The aqueous phase is extracted repeatedly with chloroform. The combined organic phases are dried over sodium sulphate, filtered and concentrated under reduced pressure on a rotary evaporator. The crude product is purified by column chromatography on silica gel. After extraction and evaporation, the residue obtained was purified by flash chromatography on silica gel with cyclohexane and ethylacetate as eluents. This afforded 100 mg (32%) of the title compound.

This gives 100 mg of N-{2-fluoro-5-[5'-(pentafluoroethyl)-4'-(trifluoromethyl)-2'H-1,3'-bipyrazol-4-yl]benzyl}propanamide (Ib-8)

$^1$H-NMR see NMR data in peak list

HPLC-MS: log P$^{a)}$=3.27, mass (m/z)=514.0 [M+H]$^+$.

$^{a)}$ Note regarding the determination of the log P values and mass detection: The determination of the given log P values was carried out in accordance with EEC Directive 79/831 Annex V.A8 by HPLC (High Performance Liquid Chromatography) on a reversed-phase column (C18). Agilent 1100 LC system; 50*4.6 Zorbax Eclipse Plus C18 1.8 micron; mobile phase A: acetonitrile (0.1% formic acid); mobile phase B: water (0.09% formic acid); linear gradient from 10% acetonitrile to 95% acetonitrile in 4.25 min, then 95% acetonitrile for a further 1.25 min; oven temperature 55° C.; flow rate: 2.0 ml/min. Mass detection is carried out via an Agilend MSD system.

The stated mass is the peak of the isotope pattern of the [M+H]$^+$ ion of the highest intensity; if the [M−H]$^−$ ion was detected, the stated mass is marked with[2].

[2] The stated mass is the peak of the isotope pattern of the [M−H]$^−$ ion of the highest intensity.

The compounds listed in Table 1 were prepared analogously to Preparation Processes A, B & D described above.

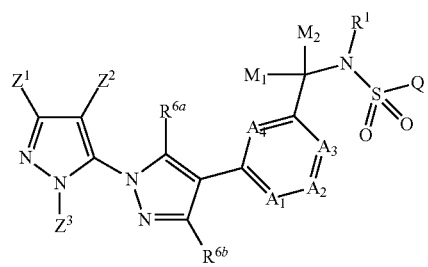

(IIc)

$^{b)}$ Note for the alternative method for determining log P values and masses: The stated log P values were determined in accordance with EEC Directive 79/831 Annex V.A8 by HPLC (High Performance Liquid Chromatography) using a reversed-phase column (C18). Waters ACQUITY UPLC-MS system; 2.1*50 mm Zorbax Eclipse Plus C18 1.8 μm 600 bar; injection volume: 0.5 ul about 1000 ppm; mobile phase A: acetonitrile (0.1% formic acid); mobile phase B: water (0.085% formic acid); linear gradient from 10% acetonitrile to 95% acetonitrile in 1.5 min, then 95% acetonitrile for a further 0.5 min; oven temperature 60° C.; flow rate: 1.0 ml/min. Mass detection is carried out via a Waters SQD system.

The stated mass is the peak of the isotope pattern of the [M+H]$^+$ ion of the highest intensity; if the [M−H]$^−$ ion was detected, the stated mass is marked with[2].

[2] The stated mass is the peak of the isotope pattern of the [M−H]$^−$ ion of the highest intensity.

NMR Data of Selected Examples

The $^1$H-NMR data of selected examples are stated in the form of $^1$H-NMR peak lists. For each signal peak, the δ-value in ppm and the signal intensity in brackets are listed.

Example IIc-1: $^1$H-NMR(400.0 MHz, DMSO):

δ = 10.267(0.6); 8.853(0.4); 8.678(5.4); 8.584(0.5); 8.424(5.7); 8.415(0.6); 8.316(0.4); 7.774(1.4); 7.768(1.5); 7.756(1.4); 7.750(1.3); 7.690(0.9); 7.684(0.9); 7.678(1.0); 7.670(1.2); 7.663(1.0); 7.657(1.0); 7.651(0.8); 7.620(0.9); 7.605(2.0); 7.590(1.0); 7.303(1.5); 7.279(1.9); 7.257(1.4); 5.756(0.5); 4.260(3.4); 4.245(3.3); 3.829(1.6); 3.813(16.0); 3.537(1.1); 3.518(1.7); 3.498(1.2); 3.479(0.3); 3.325(114.5); 2.675(0.6); 2.671(0.9); 2.666(0.7); 2.541(0.5); 2.511(51.6); 2.506(101.6); 2.502(132.7); 2.497(96.4); 2.493(46.9); 2.333(0.7); 2.329(0.9); 2.324(0.7); 1.887(1.5); 1.871(6.3); 1.853(4.1); 1.836(1.8); 1.664(0.9); 1.657(1.3); 1.646(1.7); 1.628(1.3); 1.614(0.4); 1.603(0.5); 1.576(0.6); 1.570(0.5); 1.564(0.5); 1.551(1.5); 1.544(0.9); 1.533(1.6); 1.520(1.2); 1.513(0.7); 1.504(0.5); 1.235(1.5); 1.218(1.3); 0.146(0.7); 0.008(6.7); 0.000(165.4); −0.009(6.3); −0.150(0.8)

Example IIc-2: $^1$H-NMR(400.0 MHz, DMSO):

δ = 8.687(0.4); 8.676(4.6); 8.430(0.5); 8.419(5.0); 8.315(0.5); 7.777(1.1); 7.772(1.2); 7.760(1.1); 7.754(1.2); 7.689(0.7); 7.683(0.7); 7.677(0.8); 7.668(0.9); 7.662(0.8); 7.656(0.8); 7.650(0.7); 7.607(0.9); 7.592(1.7); 7.577(0.8); 7.302(1.3); 7.281(1.5); 7.278(1.6); 7.256(1.2); 4.256(2.9); 4.241(3.0);

TABLE 1

| Beisp.-Nr. | Z$^1$ | Z$^2$ | Z$^3$ | R$^1$ | R$^{6a}$ | R$^{6b}$ | A$_4$ | A$_3$ | A$_2$ | A$_1$ | M$_1$ | M$_2$ | Q | logP $^{a)}$ | Masse $^{a)}$ |
|---|---|---|---|---|---|---|---|---|---|---|---|---|---|---|---|
| IIc-1 | C$_2$F$_5$ | CF$_3$ | CH$_3$ | H | H | H | C—H | C—F | C—H | C—H | H | H | cyclopentyl | 4.37 | 590.1 |
| IIc-2 | C$_2$F$_5$ | CF$_3$ | CH$_3$ | H | H | H | C—H | C—F | C—H | C—H | H | H | propan-2-yl | 4.06 | 564.0 |
| IIc-3 | C$_2$F$_5$ | CF$_3$ | CH$_3$ | H | H | H | C—H | C—F | C—H | C—H | H | H | ethyl | 3.85 | 550.1 |
| IIc-4 | C$_2$F$_5$ | CF$_3$ | CH$_3$ | H | H | H | C—H | C—F | C—H | C—H | H | H | CH$_3$ | 3.58 | 536.100 |

$^{a)}$ Unless indicated otherwise, the following method was used to determine the log P values and masses: The determination of the given log P values was carried out in accordance with EEC Directive 79/831 Annex V.A8 by HPLC (High Performance Liquid Chromatography) on a reversed-phase column (C18). Agilent 1100 LC system; 50*4.6 Zorbax Eclipse Plus C18 1.8 micron; mobile phase A: acetonitrile (0.1% formic acid); mobile phase B: water (0.09% formic acid); linear gradient from 10% acetonitrile to 95% acetonitrile in 4.25 min, then 95% acetonitrile for a further 1.25 min; oven temperature 55° C.; flow rate: 2.0 ml/min. Mass detection is carried out via an Agilend MSD system.

-continued 3.813(12.7); 3.325(147.5); 3.294(0.3); 3.201(0.4); 3.184(1.1); 3.167(1.6); 3.150(1.2); 3.133(0.4); 2.676(0.5); 2.671(0.7); 2.666(0.5); 2.524(2.0); 2.511(43.1); 2.507(86.0); 2.502(112.8); 2.497(81.9); 2.493(39.9); 2.333(0.6); 2.329(0.8); 2.324(0.6); 1.236(16.0); 1.219(15.7); 0.915(0.6); 0.146(0.6); 0.008(5.9); 0.000(145.5); −0.009(5.8); −0.150(0.6)

Example IIc-3: $^1$H-NMR(400.0 MHz, DMSO):

δ = 8.690(5.9); 8.677(0.6); 8.433(6.8); 7.775(1.4); 7.770(1.6); 7.757(1.4); 7.752(1.5); 7.695(0.9); 7.689(0.8); 7.683(1.0); 7.674(1.2); 7.668(1.0); 7.661(1.0); 7.656(0.9); 7.637(1.1); 7.621(2.2); 7.606(1.1); 7.308(1.7); 7.286(1.9); 7.284(2.0);

-continued 7.262(1.5); 5.757(2.1); 4.235(3.9); 4.220(3.9); 3.814(16.0); 3.328(77.6); 3.042(1.5); 3.024(4.8); 3.006(4.9); 2.987(1.6); 2.671(0.4); 2.667(0.3); 2.524(1.3); 2.511(27.4); 2.507(53.8); 2.502(69.7); 2.498(50.0); 2.333(0.3); 2.329(0.4); 1.235(0.4); 1.204(5.2); 1.185(11.0); 1.167(4.9); 0.146(0.4); 0.008(3.2); 0.000(81.8); −0.009(3.3); −0.150(0.4)

Example IIc-4: $^1$H-NMR(400.0 MHz, DMSO):

δ = 8.701(3.0); 8.442(3.3); 7.765(0.7); 7.760(0.8); 7.748(0.7); 7.743(0.8); 7.696(0.4); 7.690(0.4); 7.684(0.5); 7.676(0.6); 7.669(0.5); 7.663(0.5); 7.657(0.4); 7.596(0.5); 7.580(1.1); 7.566(0.5); 7.312(0.8); 7.290(1.0); 7.288(1.0); 7.266(0.8); 4.254(2.0); 4.238(2.0); 3.813(7.9); 3.400(0.4); 3.328(164.6); 2.936(11.0); 2.675(0.5); 2.671(0.6); 2.667(0.5); 2.506(79.9); 2.502(103.3); 2.497(75.0); 2.333(0.5); 2.329(0.7); 2.324(0.5); 2.086(1.8); 1.398(16.0); 1.141(0.6); 1.125(0.4); 0.000(0.4)

The intensity of sharp signals correlates with the height of the signals in a printed example of an NMR spectrum in cm and shows the true ratios of the signal intensities. In the case of broad signals, several peaks or the middle of the signal and their relative intensities may be shown in comparison to the most intense signal in the spectrum.

The lists of the $^1$H NMR peaks are similar to the conventional $^1$H NMR printouts and thus usually contain all peaks listed in conventional NMR interpretations.

In addition, like conventional $^1$H NMR printouts, they may show solvent signals, signals of stereoisomers of the target compounds, which likewise form part of the subject matter of the invention, and/or peaks of impurities.

In the reporting of compound signals in the delta range of solvents and/or water, our lists of $^1$H NMR peaks show the usual solvent peaks, for example peaks of DMSO in DMSO-$d_6$ and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help in this case to identify reproduction of our preparation process with reference to "by-product fingerprints".

A person skilled in the art calculating the peaks of the target compounds by known methods (MestreC, ACD simulation, but also with empirically evaluated expected values) can, if required, isolate the peaks of the target compounds, optionally using additional intensity filters. This isolation would be similar to the relevant peak picking in conventional $^1$H NMR interpretation.

Biological Working Examples for Applications in the Animal Health Sector and in Crop Protection *Boophilus microplus* Injection Test (BOOPMI Inj)
Solvent: dimethyl sulphoxide To produce a suitable preparation of active compound, 10 mg of active compound are mixed with 0.5 ml of solvent, and the concentrate is diluted with solvent to the desired concentration.

1 µl of the active compound solution is injected into the abdomen of 5 engorged adult female cattle ticks (*Boophilus microplus*). The animals are transferred into dishes and kept in a climate-controlled room.

The activity is assessed after 7 days by laying of fertile eggs. Eggs whose fertility is not visible from the outside are stored in a climate-controlled cabinet until the larvae hatch after about 42 days. An efficacy of 100% means that none of the ticks has laid any fertile eggs; 0% means that all eggs are fertile.

In this test, for example, the following compounds of the Preparation Examples show an efficacy of 100% at an application rate of 20 µg/animal: IIc-3, IIc-4

*Ctenocephalides Felis*—Oral Test (CTECFE)
Solvent: dimethyl sulphoxide

To produce a suitable preparation of active compound, 10 mg of active compound are mixed with 0.5 ml of dimethyl sulphoxide. Dilution with citrated cattle blood gives the desired concentration.

About 20 unfed adult cat fleas (*Ctenocephalides felis*) are placed into a chamber which is closed at the top and bottom with gauze. A metal cylinder whose bottom end is closed with a parafilm is placed onto the chamber. The cylinder contains the blood/active ingredient preparation, which can be imbibed by the fleas through the parafilm membrane.

After 2 days, the kill in % is determined 100% means that all of the fleas have been killed; 0% means that none of the fleas have been killed.

In this test, for example, the following compounds of the Preparation Examples show an activity of 100% at an application rate of 100 ppm: IIc-4

In this test, for example, the following compounds of the Preparation Examples show an activity of 95% at an application rate of 100 ppm: IIc-3

*Lucilia cuprina* Test (LUCICU)
Solvent: dimethyl sulphoxide

To produce a suitable preparation of active compound, 10 mg of active compound are mixed with 0.5 ml of dimethyl sulphoxide, and the concentrate is diluted with water to the desired concentration.

About 20 L1 larvae of the Australian sheep blowfly (*Lucilia cuprina*) are transferred into a test vessel containing minced horsemeat and the active compound preparation of the desired concentration.

After 2 days, the kill in % is determined 100% means that all of the larvae have been killed; 0% means that none of the larvae have been killed.

In this test, for example, the following compounds of the Preparation Examples show an activity of 100% at an application rate of 100 ppm: IIc-3, IIc-4

*Musca domestica* Test (MUSCDO)
Solvents: dimethyl sulphoxide

To produce a suitable preparation of active compound, 10 mg of active compound are mixed with 0.5 ml of dimethyl sulphoxide, and the concentrate is diluted with water to the desired concentration.

Vessels containing a sponge treated with sugar solution and the active compound preparation of the desired concentration are populated with 10 adult houseflies (*Musca domestica*).

After 2 days, the kill in % is determined 100% means that all of the flies have been killed; 0% means that none of the flies have been killed.

In this test, for example, the following compounds of the Preparation Examples show an activity of 100% at an application rate of 100 ppm: IIc-4

*Meloidogyne incognita* Test (MELGIN)
Solvent: 125.0 parts by weight of acetone

To prepare a suitable active compound preparation, 1 part by weight of active compound is mixed with the stated amount of solvent and the concentrate is diluted with water to the desired concentration.

Vessels are filled with sand, active compound solution, an egg/larvae suspension of the southern root-knot nematode (*Meloidogyne incognita*) and lettuce seeds. The lettuce seeds germinate and the plants develop. On the roots, galls are formed.

After 14 days, the nematicidal efficacy in % is determined by the formation of galls. 100% means that no galls have been found; 0% means that the number of galls on the treated plants corresponds to the untreated control.

In this test, for example, the following compounds of the Preparation Examples show an activity of 90% at an application rate of 20 ppm: IIc-3, IIc-4

Myzus persicae—Spray Test (MYZUPE)
Solvents: 78 parts by weight of acetone
  1.5 parts by weight of dimethylformamide
Emulsifier: alkylaryl polyglycol ether To produce a suitable preparation of active compound, 1 part by weight of active compound is dissolved using the stated parts by weight of solvent and made up with water comprising an emulsifier concentration of 1000 ppm until the desired concentration is reached. To produce further test concentrations, the preparation is diluted with emulsifier-containing water.

Discs of Chinese cabbage leaves (Brassica pekinensis) infested by all stages of the green peach aphid (Myzus persicae) are sprayed with an active compound preparation of the desired concentration.

After 6 days, the efficacy in % is determined. 100% here means that all of the aphids have been killed; 0% means that no aphids have been killed.

In this test, for example, the following compounds of the Preparation Examples show an activity of 90% at an application rate of 100 g/IIc-3

Phaedon cochleariae—Spray Test (PHAECO)
Solvents: 78.0 parts by weight of acetone
  1.5 parts by weight of dimethylformamide
Emulsifier: alkylaryl polyglycol ether To produce a suitable preparation of active compound, 1 part by weight of active compound is dissolved using the stated parts by weight of solvent and made up with water comprising an emulsifier concentration of 1000 ppm until the desired concentration is reached. To produce further test concentrations, the preparation is diluted with emulsifier-containing water.

Discs of Chinese cabbage leaves (Brassica pekinensis) are sprayed with an active compound preparation of the desired concentration and, after drying, populated with larvae of the mustard beetle (Phaedon cochleariae).

After 7 days, the efficacy in % is determined. 100% means that all of the beetle larvae have been killed; 0% means that none of the beetle larvae have been killed.

In this test, for example, the following compounds of the Preparation Examples show an efficacy of 100% at an application rate of 100 g/ha: IIc-1, IIc-2, IIc-3, IIc-4

Tetranychus urticae—Spray Test, OP-Resistant (TETRUR)
Solvents: 78.0 parts by weight of acetone
  1.5 parts by weight of dimethylformamide
Emulsifier: alkylaryl polyglycol ether To produce a suitable preparation of active compound, 1 part by weight of active compound is dissolved using the stated parts by weight of solvent and made up with water comprising an emulsifier concentration of 1000 ppm until the desired concentration is reached. To produce further test concentrations, the preparation is diluted with emulsifier-containing water.

Discs of bean leaves (Phaseolus vulgaris) which are infested by all stages of the greenhouse red spider mite (Tetranychus urticae) are sprayed with an active compound preparation of the desired concentration.

After 6 days, the efficacy in % is determined. 100% means that all of the spider mites have been killed; 0% means that none of the spider mites have been killed.

In this test, for example, the following compounds of the Preparation Examples show an activity of 100% at an application rate of 100 g/ha: IIc-2, IIc-3, IIc-4

In this test, for example, the following compounds of the Preparation Examples show an activity of 90% at an application rate of 100 g/ha: IIc-1

We claim:
1. A compound of the general formula (II)

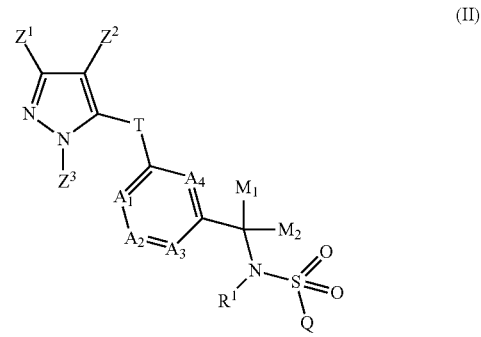

in which
$R^1$ represents hydrogen, or optionally substituted $C_1$-$C_6$-alkyl, $C_3$-$C_6$-alkenyl, $C_3$-$C_6$-alkynyl, $C_3$-$C_7$-cycloalkyl, $C_1$-$C_6$-alkylcarbonyl, $C_1$-$C_6$-alkoxycarbonyl, aryl-($C_1$-$C_3$)-alkyl, or heteroaryl-($C_1$-$C_3$)-alkyl, $M^1$ and $M^2$ each independently of one another represent hydrogen, cyano or represent optionally mono- or polysubstituted $C_1$-$C_6$-alkyl, $C_2$-$C_6$-alkenyl, $C_2$-$C_6$-alkynyl, $C_3$-$C_6$-cycloalkyl, or $C_1$-$C_6$-alkoxycarbonyl, or $M^1$ and $M^2$ with the carbon atom to which they are attached form an optionally substituted 3-, 4-, 5- or 6-membered ring which optionally contains 0, 1 or 2 nitrogen atoms and/or 0, 1 or 2 oxygen atoms and/or 0, 1 or 2 sulphur atoms, the chemical groupings
$A_1$ represents $CR^2$ or nitrogen,
$A_2$ represents $CR^3$ or nitrogen,
$A_3$ represents $CR^4$ or nitrogen and
$A_4$ represents $CR^5$ or nitrogen,
but where not more than three of the chemical groupings $A_1$ to $A_4$ simultaneously represent nitrogen;

$R^2$, $R^3$, $R^4$ and $R^5$ independently of one another represent hydrogen, halogen, cyano, nitro, or optionally substituted $C_1$-$C_6$-alkyl, $C_3$-$C_6$-cycloalkyl, $C_1$-$C_6$-alkoxy, N—$C_1$-$C_6$-alkoxy-imino-$C_1$-$C_3$-alkyl, $C_1$-$C_6$-alkylsulphanyl, $C_1$-$C_6$-alkylsulphinyl, $C_1$-$C_6$-alkylsulphonyl, N—$C_1$-$C_6$-alkylamino or N,N-di-$C_1$-$C_6$-alkylamino;

if none of the groupings $A_2$ and $A_3$ represents nitrogen, $R^3$ and $R^4$ together with the carbon atom to which they are attached may form a 5- or 6-membered ring which contains 0, 1 or 2 nitrogen atoms and/or 0 or 1 oxygen atom and/or 0 or 1 sulphur atom, or if none of the groupings $A_1$ and $A_2$ represents nitrogen, $R^2$ and $R^3$ together with the carbon atom to which they are attached may form a 6-membered ring which contains 0, 1 or 2 nitrogen atoms;

Q represents hydrogen, hydroxy, amino or one of the optionally substituted groupings alkyl, alkoxy, alkenyl, alkynyl, cycloalkyl, heterocycloalkyl, cycloalkylalkyl, arylalkyl, heteroarylalkyl or represents a grouping N-alkylamino, N-alkylcarbonylamino, or N,N-dialkylamino; or Q represents an unsaturated 6-membered carbocycle which is optionally mono- or polysubstituted by V or an unsaturated 5- or 6-membered heterocyclic ring which is optionally mono- or polysubstituted by V, where V independently of one another represent halogen, cyano, nitro, or optionally substituted alkyl, alkenyl, alkynyl, cycloalkyl, alkoxy, N-alkoxyiminoalkyl, alkylsulphanyl, alkylsulphinyl, alkylsulphonyl, or N,N-dialkylamino, T represents one of the 5-membered heteroaromatics T1-T8 listed below, where the bond to the pyrazole head group is marked with an asterisk,

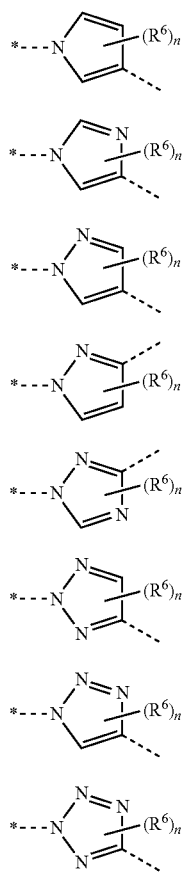

where $R^6$ independently of one another represent halogen, cyano, nitro, amino or optionally substituted $C_1$-$C_6$-alkyl, $C_1$-$C_6$-alkoxy, $C_1$-$C_6$-alkylcarbonyl, $C_1$-$C_6$-alkylsulphanyl, $C_1$-$C_6$-alkylsulphinyl, or $C_1$-$C_6$-alkylsulphonyl, and n represents the values 0, 1, or 2;

$Z^1$ represents optionally substituted alkyl or cycloalkyl, and $Z^2$ represents hydrogen, halogen, cyano, nitro, amino or optionally substituted alkyl, alkylcarbonyl, alkylsulphanyl, alkylsulphinyl, or alkylsulphonyl, and $Z^3$ represents hydrogen or optionally substituted alkyl, cycloalkyl, alkenyl, alkynyl, aryl or hetaryl.

2. A compound according to claim 1 in which $R^1$ represents hydrogen, or optionally substituted $C_1$-$C_6$-alkyl, $C_3$-$C_6$-alkenyl, $C_3$-$C_6$-alkynyl, $C_3$-$C_7$-cycloalkyl, $C_1$-$C_6$-alkylcarbonyl, $C_1$-$C_6$-alkoxycarbonyl, aryl-($C_1$-$C_3$)-alkyl, or heteroaryl-($C_1$-$C_3$)-alkyl, $M^1$ and $M^2$ each independently of one another represent hydrogen, cyano or represent optionally mono- or polysubstituted $C_1$-$C_6$-alkyl, $C_2$-$C_6$-alkenyl, $C_2$-$C_6$-alkynyl, $C_3$-$C_6$-cycloalkyl, or $C_1$-$C_6$-alkoxycarbonyl, or $M^1$ and $M^2$ with the carbon atom to which they are attached form an optionally substituted 3-, 4-, 5- or 6-membered ring which optionally contains 0, 1 or 2 nitrogen atoms and/or 0, 1 or 2 oxygen atoms and/or 0, 1 or 2 sulphur atoms, the chemical groupings $A_1$ represents $CR^2$ or nitrogen,
$A_2$ represents $CR^3$ or nitrogen,
$A_3$ represents $CR^4$ or nitrogen and
$A_4$ represents $CR^5$ or nitrogen, but where not more than three of the chemical groupings $A_1$ to $A_4$ simultaneously represent nitrogen;

$R^2$, $R^3$, $R^4$ and $R^5$ independently of one another represent hydrogen, halogen, cyano, nitro, or optionally substituted $C_1$-$C_6$-alkyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulphanyl, $C_1$-$C_6$-alkylsulphinyl, $C_1$-$C_6$-alkylsulphonyl, N—$C_1$-$C_6$-alkylamino or N,N-di-$C_1$-$C_6$-alkylamino;

if none of the groupings $A_2$ and $A_3$ represents nitrogen, $R^3$ and $R^4$ together with the carbon atom to which they are attached may form a 5- or 6-membered ring which contains 0, 1 or 2 nitrogen atoms and/or 0 or 1 oxygen atom and/or 0 or 1 sulphur atom, or if none of the groupings $A_1$ and $A_2$ represents nitrogen, $R^2$ and $R^3$ together with the carbon atom to which they are attached may form a 6-membered ring which contains 0, 1 or 2 nitrogen atoms;

Q represents hydrogen, formyl, hydroxy, amino or one of the optionally substituted groupings $C_1$-$C_6$-alkyl, $C_2$-$C_6$-alkenyl, $C_2$-$C_6$-alkynyl, $C_3$-$C_6$-cycloalkyl, $C_2$-$C_7$-heterocycloalkyl, $C_1$-$C_4$-alkoxy, $C_3$-$C_6$-cycloalkyl-$C_1$-$C_6$-alkyl, aryl-($C_1$-$C_3$)-alkyl, heteroaryl-($C_1$-$C_3$)-alkyl or represents a grouping N—$C_1$-$C_4$-alkylamino, N—$C_1$-$C_4$-alkylcarbonylamino, or N,N-di-$C_1$-$C_4$-alkylamino; or Q represents an unsaturated 6-membered carbocycle which is optionally mono- or polysubstituted by V or an unsaturated 5- or 6-membered heterocyclic ring which is optionally mono- or polysubstituted by V, where V independently of one another represent halogen, cyano, nitro, or optionally substituted $C_1$-$C_6$-alkyl, $C_2$-$C_4$-alkenyl, $C_2$-$C_4$-alkynyl, $C_3$-$C_6$-cycloalkyl, $C_1$-$C_6$-alkoxy, N—$C_1$-$C_6$-alkoxy-imino-$C_1$-$C_3$-alkyl, $C_1$-$C_6$-alkylsulphanyl, $C_1$-$C_6$-alkylsulphinyl, $C_1$-$C_6$-alkylsulphonyl, or N,N-di-($C_1$-$C_6$-alkyl)amino;

T represents one of the 5-membered heteroaromatics T1-T8 listed below, where the bond to the pyrazole head group is marked with an asterisk,

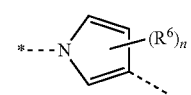

-continued

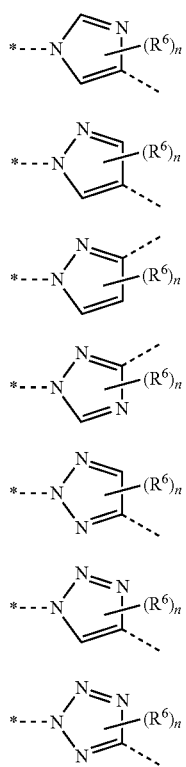

where
- $R^6$ independently of one another represent halogen, cyano, nitro, amino or optionally halogen-substituted $C_1$-$C_6$-alkyl, $C_1$-$C_6$-alkoxy, $C_1$-$C_6$-alkylcarbonyl, $C_1$-$C_6$-alkylsulphanyl, $C_1$-$C_6$-alkylsulphinyl, or $C_1$-$C_6$-alkylsulphonyl, and
- n represents the values 0 or 1;
- $Z^1$ represents optionally substituted $C_1$-$C_6$-haloalkyl, or $C_3$-$C_6$-halocycloalkyl,
- $Z^2$ represents hydrogen, halogen, cyano, nitro, amino or optionally substituted $C_1$-$C_6$-alkyl, $C_1$-$C_6$-alkylcarbonyl, $C_1$-$C_6$-alkylsulphanyl, $C_1$-$C_6$-alkylsulphinyl, or $C_1$-$C_6$-alkylsulphonyl, and
- $Z^3$ represents hydrogen or optionally substituted $C_1$-$C_6$-alkyl, $C_3$-$C_6$-cycloalkyl, $C_3$-$C_6$-alkenyl, $C_3$-$C_6$-alkynyl, aryl or hetaryl.

3. A compound according to claim 1 in which
$R^1$ represents hydrogen or represents $C_1$-$C_6$-alkyl, $C_3$-$C_6$-alkenyl, $C_3$-$C_6$-alkynyl, $C_3$-$C_7$-cycloalkyl, $C_1$-$C_6$-alkylcarbonyl, $C_1$-$C_6$-alkoxycarbonyl, aryl-($C_1$-$C_3$)-alkyl, or heteroaryl-($C_1$-$C_3$)-alkyl which are optionally mono- to heptasubstituted independently of one another by fluorine, chlorine, cyano, $C_1$-$C_6$-alkoxy or $C_1$-$C_6$-alkoxycarbonyl,
$M^1$ represents hydrogen,
$M^2$ represents hydrogen, cyano or represents $C_1$-$C_6$-alkyl, $C_2$-$C_6$-alkenyl, $C_3$-$C_6$-cycloalkyl, or $C_1$-$C_3$-alkoxycarbonyl which are optionally mono- to pentasubstituted independently of one another by fluorine, chlorine, cyano or $C_1$-$C_3$-alkoxy,
$M^1$ and $M^2$ with the carbon atom to which they are attached form an optionally substituted 3-membered ring, the chemical groupings
- $A_1$ represents $CR^2$ or nitrogen,
- $A_2$ represents $CR^3$ or nitrogen,
- $A_3$ represents $CR^4$ or nitrogen and
- $A_4$ represents $CR^5$ or nitrogen,
but where not more than three of the chemical groupings $A_1$ to $A_4$ simultaneously represent nitrogen;
$R^2$, $R^3$, $R^4$ and $R^5$ independently of one another represent hydrogen, fluorine, chlorine, bromine, iodine, cyano, nitro or represent $C_1$-$C_6$-alkyl, $C_3$-$C_6$-cycloalkyl, $C_1$-$C_6$-alkoxy, N—$C_1$-$C_6$-alkoxyimino-$C_1$-$C_3$-alky, $C_1$-$C_6$-alkylsulphanyl, $C_1$-$C_6$-alkylsulphinyl, $C_1$-$C_6$-alkylsulphonyl, N—$C_1$-$C_6$-alkylamino or N,N-di-$C_1$-$C_6$-alkylamino which are optionally mono- to pentasubstituted independently of one another by fluorine, chlorine, cyano, hydroxycarbonyl, $C_1$-$C_6$-alkoxycarbonyl, $C_1$-$C_6$-alkylcarbonyl or phenyl;
Q represents hydrogen, amino or one of the groupings $C_1$-$C_6$-alkyl, $C_2$-$C_6$-alkenyl, $C_2$-$C_6$-alkynyl, $C_3$-$C_6$-cycloalkyl, $C_2$-$C_5$-heterocycloalkyl, $C_1$-$C_4$-alkoxy, $C_3$-$C_6$-cycloalkyl-$C_1$-$C_6$-alkyl, aryl-($C_1$-$C_3$)-alkyl, heteroaryl-($C_1$-$C_3$)-alkyl, N—$C_1$-$C_4$-alkylamino, N—$C_1$-$C_4$-alkylcarbonylamino or N,N-di-$C_1$-$C_4$-alkylamino which are optionally independently of one another mono- to pentasubstituted by hydroxy, nitro, amino, fluorine, chlorine, $C_1$-$C_6$-alkyl, $C_1$-$C_6$-alkoxy, cyano, hydroxycarbonyl, $C_1$-$C_4$-alkoxycarbonyl, $C_1$-$C_4$-alkylcarbamoyl, $C_3$-$C_7$-cycloalkylcarbamoyl, or phenyl; or
Q represents aryl substituted by 0-4 substituents V or a 5- or 6-membered heteroaromatic substituted by 0-4 substituents V, where
V independently of one another represent halogen, cyano, nitro, or optionally substituted $C_1$-$C_6$-alkyl, $C_2$-$C_4$-alkenyl, $C_2$-$C_4$-alkynyl, $C_3$-$C_6$-cycloalkyl, $C_1$-$C_6$-alkoxy, N—$C_1$-$C_6$-alkoxyimino-$C_1$-$C_3$-alky, $C_1$-$C_6$-alkylsulphanyl, $C_1$-$C_6$-alkylsulphinyl, $C_1$-$C_6$-alkylsulphonyl, or N,N-di-($C_1$-$C_6$-alkyl)amino;
T represents one of the 5-membered heteroaromatics T1-T8 listed below, where the bond to the pyrazole head group is marked with an asterisk,

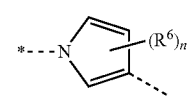
T1

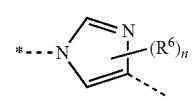
T2

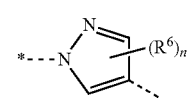
T3

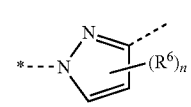
T4

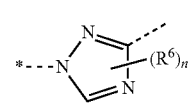
T5

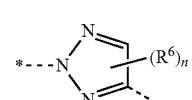
T6

-continued

T7

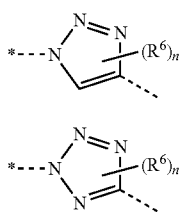

T8

*---N-N=N-(R^6)_n (T8 structure)

where
R$^6$ independently of one another represent fluorine, chlorine, bromine, iodine, cyano, nitro, amino or represents C$_1$-C$_6$-alkyl, C$_1$-C$_6$-alkoxy, C$_1$-C$_6$-alkylcarbonyl, C$_1$-C$_6$-alkylsulphanyl, C$_1$-C$_6$-alkylsulphinyl, C$_1$-C$_6$-alkylsulphonyl which are optionally independently of one another mono to pentasubstituted by fluorine and/or chlorine, and
n represents the values 0 or 1;
Z$^1$ represents optionally substituted C$_1$-C$_6$-haloalkyl, or C$_3$-C$_6$-halocycloalkyl,
Z$^2$ represents hydrogen, fluorine, chlorine, bromine, iodine, cyano, nitro, amino or represents C$_1$-C$_6$-alkyl, C$_1$-C$_6$-alkylcarbonyl, C$_1$-C$_6$-alkylsulphanyl, C$_1$-C$_6$-alkylsulphinyl, or C$_1$-C$_6$-alkylsulphonyl which are optionally independently of one another mono- to pentasubstituted by fluorine and/or chlorine, and
Z$^3$ represents hydrogen or optionally substituted C$_1$-C$_6$-alkyl, C$_3$-C$_6$-cycloalkyl, C$_3$-C$_4$-alkenyl, C$_3$-C$_4$-alkynyl, aryl or hetaryl.

4. A compound according to claim 1 in which
R$^1$ represents hydrogen, methyl, ethyl, n-propyl, isopropyl, n-butyl, isobutyl, s-butyl, t-butyl, methoxymethyl, ethoxymethyl, propoxymethyl, methylcarbonyl, ethylcarbonyl, n-propylcarbonyl, isopropylcarbonyl, n-butylcarbonyl, isobutylcarbonyl, s-butylcarbonyl, t-butylcarbonyl, methoxycarbonyl, ethoxycarbonyl, n-propoxycarbonyl, isopropoxycarbonyl, n-butoxycarbonyl, isobutoxycarbonyl, s-butoxycarbonyl, t-butoxycarbonyl, cyanomethyl, 2-cyanoethyl, benzyl, 4-methoxybenzyl, pyrid-2-ylmethyl, pyrid-3-ylmethyl, pyrid-4-ylmethyl, or 6-chloropyrid-3-ylmethyl;
M$^1$ represents hydrogen,
M$^2$ represents hydrogen, methyl, ethyl, difluoromethyl, trichloromethyl, dichlorofluoromethyl, trifluoromethyl, cyclopropyl, cyclobutyl, methoxycarbonyl, or ethoxycarbonyl,
M$^1$ and M$^2$ with the carbon atom to which they are attached form a 3-membered carbocycle,
the chemical groupings
A$^1$ represents CR$^2$ or nitrogen,
A$^2$ represents CR$^3$ or nitrogen,
A$^3$ represents CR$^4$ or nitrogen and
A$^4$ represents CR$^5$ or nitrogen,
but where not more than three of the chemical groupings A$_1$ to A$_4$ simultaneously represent nitrogen;
R$^2$ and R$^5$ independently of one another represent hydrogen, methyl, fluorine or chlorine and
R$^3$ and R$^4$ independently of one another represent hydrogen, fluorine, chlorine, bromine, iodine, cyano, nitro, methyl, ethyl, fluoromethyl, difluoromethyl, chlorodifluoromethyl, trifluoromethyl, 2,2,2-trifluoroethyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino) ethyl, methylsulfanyl, trifluoromethylsulphanyl, methylsulphonyl, methylsulphinyl, trifluoromethylsulphonyl, or trifluoromethylsulphinyl;
Q represents hydrogen, methyl, ethyl, n-propyl, isopropyl, t-butyl, 1-methylpropyl, n-butyl, 2-methylpropyl, 2-methylbutyl, hydroxymethyl, 2-hydroxyethyl, 2-hydroxypropyl, cyanomethyl, 2-cyanoethyl, trifluoromethyl, 1-fluoroethyl, 2-fluoroethyl, 2,2-difluoroethyl, 2,2,2-trifluoroethyl, 1-trifluoromethylethyl, 2,2-difluoropropyl, 3,3,3-trifluoropropyl, 2,2-dimethyl-3-fluoropropyl, cyclopropyl,1-cyanocyclopropyl, cyclopropylmethyl, cyclobutyl, cyclopentyl, cyclohexyl,1-cyclopropylethyl, bis(cyclopropyl)methyl, 2,2-dimethylcyclopropylmethyl, 2-phenylcyclopropyl, 2,2-dichlorocyclopropyl, trans-2-chlorocyclopropyl, cis-2-chlorocyclopropyl, 2,2-difluorocyclopropyl, trans-2-fluorocyclopropyl, cis-2-fluorocyclopropyl, trans-4-hydroxycyclohexyl, 4-trifluoromethylcyclohexyl, ethenyl, 1-methylethenyl, prop-1-enyl, 2-methylprop-1-enyl, 3-methylbut-1-enyl, 3,3,3-trifluoroprop-1-enyl, 1-ethylethenyl, 1-methylprop-1-enyl, prop-2-ynyl, 3-fluoroprop-2-enyl, oxetan-3-yl, thietan-3-yl, 1-oxidothietan-3-yl, 1,1-dioxidothietan-3-yl, tetrahydrofuran-3-yl, 1,1-dioxidotetrahydrothiophen-3-yl, isoxazol-3-ylmethyl, 1,2,4-triazol-3-ylmethyl, 3-methyloxetan-3-ylmethyl, benzyl, 2,6-difluorophenylmethyl, 3-fluorophenylmethyl, 2-fluorophenylmethyl, 2,5-difluorophenylmethyl, 1-phenylethyl, 4-chlorophenylethyl, 2-trifluoromethylphenylethyl, 1-pyridin-2-ylethyl, pyridin-2-ylmethyl, 5-fluoropyridin-2-ylmethyl, (6-chloropyridin-3-yl)methyl, pyrirnidin-2-ylmethyl, thiophen-2-yl-methyl, 2-ethoxyethyl, 2-methoxyethyl, 1-(methylsulphanyl)ethyl, 2-(methylsulphanyl)ethyl, 1-methyl-2-(ethylsulphanyl)ethyl, 2-methyl-1-(methylsulphanyl)propan-2-yl, methoxycarbonyl, ethoxycarbonyl, methoxycarbonylmethyl, NH$_2$, N-ethylamino, N-allylamino, N,N-dimethylamino, N,N-diethylamino, methoxy, ethoxy, propoxy, isopropoxy, or tert-butoxy; or
Q represents phenyl, naphthyl, pyridazine, pyrazine, pyrimidine, triazine, pyridine, pyrazole, thiazole, isothiazole, oxazole, isoxazole, triazole, imidazole, furan, thiophene, pyrrole, oxadiazole, or thiadiazole substituted by 0, 1, 2 or 3 substituents V, where
V independently of one another represent fluorine, chlorine, bromine, iodine, cyano, nitro, methyl, ethyl, difluoromethyl, trichloromethyl, chlorodifluoromethyl, dichlorofluoromethyl, trifluoromethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, heptafluoro-n-propyl, heptafluoroisopropyl, nonafluoro-n-butyl, cyclopropyl, cyclobutyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, methylsulphonyl, methylsulphinyl, trifluoromethylsulphonyl N,N,trifluoromethylsulphinyl, trifluoromethylsulphanyl, or -dimethylamino;

T represents one of the 5-membered heteroaromatics T1-T8 listed below, where the bond to the pyrazole head group is marked with an asterisk,

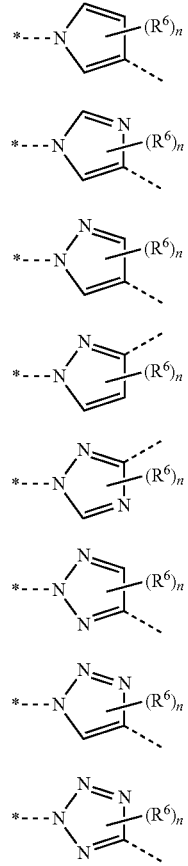

where
R⁶ independently of one another represent fluorine, chlorine, cyano, nitro, amino, methyl, ethyl, propyl, 1-methylethyl, tert-butyl, trifluoromethyl, difluoromethyl, methoxy, ethoxy, trifluoromethoxy, 2,2-difluoroethoxy, 2,2,2-trifluoroethoxy, methylcarbonyl, ethylcarbonyl, trifluoromethylcarbonyl, methylsulphanyl, methylsulphinyl, methylsulphonyl, trifluoromethylsulphonyl, trifluoromethylsulphanyl, or trifluoromethylsulphinyl,
n represents the values 0 or 1;
Z¹ represents difluoromethyl, trichloromethyl, chlorodifluoromethyl, dichlorofluoromethyl, trifluoromethyl, bromodichloromethyl, 1-fluoroethyl, 1-fluoro-1-methylethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, heptafluoro-n-propyl, heptafluoroisopropyl, nonafluoro-n-butyl, cyclopropyl, 1-chlorocyclopropyl, 1-fluorocyclopropyl, 1-bromocyclopropyl, 1-cyanocyclopropyl, 1-trifluoromethylcyclopropyl, cyclobutyl or 2,2-difluoro-1-methylcyclopropyl,
Z² represents hydrogen, fluorine, chlorine, bromine, iodine, cyano, nitro, amino, methyl, ethyl, 1,1-t-butyl, difluoromethyl, trichloromethyl, chlorodifluoromethyl, dichlorofluoromethyl, trifluoromethyl, bromodichloromethyl, 1-fluoroethyl, 1-fluoro-1-methylethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, heptafluoro-n-propyl, heptafluoroisopropyl, nonafluoro-n-butyl, methylsulphanyl, methylsulphinyl, methylsulphonyl, ethylthio, ethylsulphinyl, ethylsulphonyl, trifluoromethylsulphanyl, trifluoromethylsulphinyl, trifluoromethylsulphonyl, chlorodifluoromethylsulphanyl, chlorodifluoromethylsulphinyl, chlorodifluoromethylsulphonyl, dichlorofluoromethylsulphanyl, dichlorofluoromethylsulphinyl, or dichlorofluoromethylsulphonyl, and
Z³ represents hydrogen, methyl, ethyl, n-propyl, isopropyl, n-butyl, isobutyl, s-butyl, t-butyl, 1-propenyl, 1-propynyl, 1-butynyl, difluoromethyl, trichloromethyl, chlorodifluoromethyl, dichlorofluoromethyl, trifluoromethyl, 1-fluoroethyl, 1-fluoro-1-methylethyl, 2-fluoroethyl, 2,2-difluoroethyl, 2,2,2-trifluoroethyl, phenyl, 2-chlorophenyl, 3-chlorophenyl, 4-chlorophenyl, 2,4-dichlorophenyl, 2,5-dichlorophenyl, 3,4-dichlorophenyl, 2,6-dichlorophenyl, 2,6-dichloro-4-trifluoromethylphenyl, or 3-chloro-5-trifluoromethylpyridin-2-yl.

5. A compound according to claim 1 in which
Z¹ represents trifluoromethyl, 1-chlorocyclopropyl, 1-fluorocyclopropyl or pentafluoroethyl,
Z² represents trifluoromethyl, nitro, methylsulphanyl, methylsulphinyl, methylsulphonyl, fluorine, chlorine, bromine, cyano or iodine,
Z³ represents methyl, ethyl, n-propyl or hydrogen,
R¹ represents hydrogen, methyl, ethyl, n-propyl, isopropyl, n-butyl, isobutyl, s-butyl, t-butyl, methoxymethyl, ethoxymethyl, propoxymethyl, methylcarbonyl, ethylcarbonyl, n-propylcarbonyl, isopropylcarbonyl, n-butylcarbonyl, isobutylcarbonyl, s-butylcarbonyl, t-butylcarbonyl, methoxycarbonyl, ethoxycarbonyl, n-propoxycarbonyl, isopropoxycarbonyl, n-butoxycarbonyl, isobutoxycarbonyl, s-butoxycarbonyl, t-butoxycarbonyl, cyanomethyl, 2-cyanoethyl, benzyl, 4-methoxybenzyl, pyrid-2-ylmethyl, pyrid-3-ylmethyl, pyrid-4-ylmethyl, or 6-chloropyrid-3-ylmethyl;
M¹ represents hydrogen;
M² represents hydrogen or methyl;
M¹ and M² with the carbon atom to which they are attached form a 3-membered carbocycle,
A¹ and A⁴ represent CH,
A² represents CH or N,
A³ represents CR⁴ and
R⁴ represents methyl, ethyl, fluorine, chlorine, bromine or iodine,
T represents one of the 5-membered heteroaromatics T1-T8 listed below, where the bond to the pyrazole head group is marked with an asterisk,

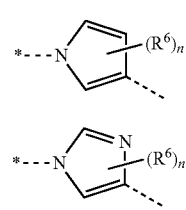

-continued

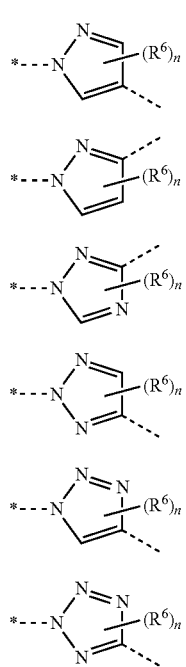

where
R⁶ represents hydrogen, methyl, ethyl, 2-methylethyl, 2,2-dimethylethyl, fluorine, chlorine, bromine, iodine, nitro, trifluoromethyl, or amino,
Q represents hydrogen, methyl, ethyl, n-propyl, 1-methylethyl, 1,1-dimethylethyl, n-butyl, 1-methylpropyl, 2-methylpropyl, 2-methylbutyl, hydroxymethyl, 2-hydroxypropyl, cyanomethyl, 2-cyanoethyl, 2-fluoroethyl, 2,2-difluoroethyl, 2,2,2-trifluoroethyl, 1-trifluoromethylethyl, 2,2-difluoropropyl, 3,3,3-trifluoropropyl, 2,2-dimethyl-3-fluoropropyl, cyclopropyl, cyclopropylmethyl, cyclobutyl, cyclopentyl, cyclohexyl, 1-cyclopropylethyl, bis(cyclopropyl)methyl, 2,2-dimethylcyclopropylmethyl, 2-phenylcyclopropyl, 2,2-dichlorocyclopropyl, trans-2-chlorocyclopropyl, cis-2-chlorocyclopropyl, 2,2-difluorocyclopropyl, trans-2-fluorocyclopropyl, cis-2-fluorocyclopropyl, trans-4-hydroxycyclohexyl, 4-trifluoromethylcyclohexyl, ethenyl, 1-methylethenyl, prop-1-enyl, 2-methylprop-1-enyl, 3-methylbut-1-enyl, 3,3,3-trifluoroprop-1-enyl, 1-ethylethenyl, 1-methylprop-1-enyl, prop-2-ynyl, 3-fluoroprop-2-enyl, oxetan-3-yl, thietan-3-yl, 1-oxidothietan-3-yl, 1,1-dioxidothietan-3-yl, isoxazol-3-ylmethyl, 1,2,4-triazol-3-ylmethyl, 3-methyloxetan-3-ylmethyl, benzyl, 2,6-difluorophenylmethyl, 3-fluorophenylmethyl, 2-fluorophenylmethyl, 2,5-difluorophenylmethyl, 1-phenylethyl, 4-chlorophenylethyl, 2-trifluormethylphenylethyl, 1-pyridin-2-ylethyl, pyridin-2-ylmethyl, (6-chloropyridin-3-yl)methyl, 5-fluoropyridin-2-ylmethyl, pyrimidin-2-ylmethyl, methoxy, 2-ethoxyethyl, 2-(methylsulphanyl)ethyl, 1-methyl-2-(ethylsulphanyl)ethyl, 2-methyl-1-(methylsulphanyl)propan-2-yl, methoxycarbonyl, methoxycarbonylmethyl, $NH_2$, N-ethylamino, N-allylamino, N,N-dimethylamino, N,N-diethylamino, methoxy, ethoxy, propoxy, isopropoxy, or tert-butoxy; or Q represents phenyl, naphthyl, pyridazine, pyrazine, pyrimidine, triazine, pyridine, pyrazole, thiazole, isothiazole, oxazole, isoxazole, triazole, imidazole, furan, thiophene, pyrrole, oxadiazole, or thiadiazole substituted by 0, 1, 2 or 3 substituents V, where
V independently of one another represent fluorine, chlorine, bromine, iodine, cyano, nitro, methyl, ethyl, difluoromethyl, trichloromethyl, chlorodifluoromethyl, dichlorofluoromethyl, trifluoromethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, heptafluoro-n-propyl, heptafluoroisopropyl, nonafluoro-n-butyl, cyclopropyl, cyclobutyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphonyl, methylsulphonyl, methylsulphinyl, trifluoromethylsulphonyl, trifluoromethylsulphinyl, trifluoromethylsulphanyl, or N,N-dimethylamino.

6. A compound according to claim 1, wherein
$Z^1$ represents pentafluoroethyl,
$Z^2$ represents trifluoromethyl,
$Z^3$ represents methyl,
$R^1$ represents hydrogen,
$M^1$ represents hydrogen,
$M^2$ represents hydrogen,
$A^1$ and $A^4$ represent CH,
$A^2$ represents CH,
$A^3$ represents $CR^4$ and
$R^4$ represents fluorine,
T represents T3 listed below, where the bond to the pyrazole head group is marked with an asterisk,

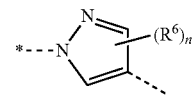

where
$R^6$ represents hydrogen,
n represents the value 2,
Q represents methyl, ethyl, 1-methylethyl, cyclopentyl, or propan-2-yl.

7. A compound according to claim 1 for use as a medicament.

8. A pharmaceutical composition comprising at least one compound according to claim 1.

9. The pharmaceutical composition of claim 8, further comprising a synergist, an insecticidal active compound, a nematicidal active compound, an acaricidal active compound, an antimicrobial active compound, or a microorganism.

10. A process for preparing crop protection composition comprising combining a compound according to claim 1 and customary extenders and/or surfactants.

11. A method for controlling pests, characterized in that a compound according to claim 1 is allowed to act on the pests and/or their habitat.

12. A method for controlling insects, arachnids and nematodes, wherein a compound of the general formula (II) according to claim 1 is allowed to act on the insects, arachnids, or nematodes.

13. A method for controlling a parasite on an animal comprising treating the animal with a compound according to claim 1.

14. The method according to claim 13, wherein the parasite is an ectoparasite.

15. A method for protecting the propagation material of plants comprising treating the propagation material with a compound according to claim 1.

16. A method for protecting a seed comprising treating the seed with a compound according to claim 1.

* * * * *